United States Patent
Kao et al.

(10) Patent No.: US 10,370,445 B2
(45) Date of Patent: *Aug. 6, 2019

(54) METHODS AND AGENTS FOR THE DIAGNOSIS AND TREATMENT OF HEPATOCELLULAR CARCINOMA

(71) Applicant: Circular Commitment Company, Taipei (TW)

(72) Inventors: Kuo-Jang Kao, Gainesville, FL (US); Andrew T. Huang, Durham, NC (US)

(73) Assignee: Circular Commitment Company, Taipei (TW)

( * ) Notice: Subject to any disclaimer, the term of this patent is extended or adjusted under 35 U.S.C. 154(b) by 84 days.

This patent is subject to a terminal disclaimer.

(21) Appl. No.: 15/370,711

(22) Filed: Dec. 6, 2016

(65) Prior Publication Data

US 2017/0145092 A1 May 25, 2017

Related U.S. Application Data

(62) Division of application No. 14/335,129, filed on Jul. 18, 2014, now Pat. No. 9,545,443, which is a division of application No. 12/933,248, filed as application No. PCT/US2009/001689 on Mar. 18, 2009, now Pat. No. 8,815,240.

(60) Provisional application No. 61/069,910, filed on Mar. 19, 2008.

(51) Int. Cl.

| | |
|---|---|
| *G01N 33/53* | (2006.01) |
| *A61K 39/00* | (2006.01) |
| *C07K 16/28* | (2006.01) |
| *A61K 51/10* | (2006.01) |
| *C07K 16/30* | (2006.01) |
| *G01N 33/574* | (2006.01) |
| *A61K 39/395* | (2006.01) |
| *A61K 45/06* | (2006.01) |
| *G01N 33/577* | (2006.01) |
| *C12Q 1/6886* | (2018.01) |

(52) U.S. Cl.
CPC ........ *C07K 16/28* (2013.01); *A61K 39/39558* (2013.01); *A61K 45/06* (2013.01); *A61K 51/1018* (2013.01); *A61K 51/1027* (2013.01); *A61K 51/1057* (2013.01); *C07K 16/303* (2013.01); *G01N 33/577* (2013.01); *G01N 33/57438* (2013.01); *C07K 2317/56* (2013.01); *C07K 2317/565* (2013.01); *C07K 2317/92* (2013.01); *C07K 2319/21* (2013.01); *C12Q 1/6886* (2013.01); *G01N 2333/47* (2013.01)

(58) Field of Classification Search
None
See application file for complete search history.

(56) References Cited

U.S. PATENT DOCUMENTS

| | | | |
|---|---|---|---|
| 6,875,570 B2 | 4/2005 | Gerlach et al. | |
| 8,815,240 B2 | 8/2014 | Kao et al. | |
| 8,821,880 B2 | 9/2014 | Kao et al. | |
| 9,394,359 B2 | 7/2016 | Kao et al. | |
| 9,493,552 B2 | 11/2016 | Kao et al. | |
| 9,545,443 B2 | 1/2017 | Kao et al. | |
| 2008/0233117 A1 | 9/2008 | Roberts et al. | |
| 2011/0085973 A1 | 4/2011 | Kao et al. | |
| 2011/0159498 A1 | 6/2011 | Kao et al. | |
| 2011/0262349 A1 | 10/2011 | Kao et al. | |
| 2014/0322131 A1 | 10/2014 | Kao et al. | |
| 2015/0017171 A1 | 1/2015 | Kao et al. | |
| 2015/0140021 A1 | 5/2015 | Kao et al. | |
| 2017/0000898 A1 | 1/2017 | Kao et al. | |
| 2018/0362614 A1 | 12/2018 | Kao et al. | |

FOREIGN PATENT DOCUMENTS

| | | |
|---|---|---|
| WO | 1996/001653 A1 | 1/1996 |
| WO | WO 1998/031394 A2 | 7/1998 |
| WO | WO 2003/010336 A2 | 2/2003 |
| WO | WO 2003/023008 A2 | 3/2003 |
| WO | WO 2003/024392 A2 | 3/2003 |
| WO | WO 2006/105361 A2 | 10/2006 |
| WO | WO 2006/110593 A2 | 10/2006 |
| WO | WO 2008/091781 A1 | 7/2008 |
| WO | WO 2009/117096 A1 | 9/2009 |
| WO | WO 2009/126271 A1 | 10/2009 |
| WO | WO 2010/051105 A1 | 5/2010 |
| WO | 2011/023785 A1 | 3/2011 |

OTHER PUBLICATIONS

Bergers, G., and Coussens, L. M., "Extrinsic regulators of epithelial tumor progression: metalloproteinases," *Current Opinion in Genetics & Development*, 10: 120-127 (2000).

Bernard, A., et al., "A Unique Epitope on the CD2 Molecule Defined by the Monoclonal Antibody 9-1: Epitope-Specific Modulation of the E-Rosette Receptor and Effects on T-Cell Functions," *Human Immunology*, 17: 388-405 (1986).

Caldas, C., et al., "Humanization of the anti-CD18 antibody 6.7: an unexpected effect of a framework residue in binding to antigen," *Molecular Immunology*, 39: 941-952 (2003).

Carson-Walter, E. B., et al., "Plasmalemmal Vesicle Associated Protein-1 is a Novel Marker Implicated in Brain Tumor Angiogenesis," *Clin. Cancer Res.*, 11(21): 7643-7650 (2005).

Casset, F., et al., "A peptide mimetic of an anti-CD4 monoclonal antibody by rational design," *Biochemical and Biophysical Research Communications*, 307: 198-205 (2003).

(Continued)

*Primary Examiner* — Mark Halvorson
(74) *Attorney, Agent, or Firm* — Hamilton, Brook, Smith & Reynolds, P.C.

(57) ABSTRACT

The present invention relates to methods of diagnosing and methods of treating hepatocellular carcinoma in a subject. The invention also relates to antagonists of PLVAP proteins, such as antibodies that specifically bind PLVAP proteins, as well as compositions and kits comprising antagonists of PLVAP proteins. The invention further relates to humanized antibodies that specifically bind PLVAP protein.

14 Claims, 29 Drawing Sheets

Specification includes a Sequence Listing.

(56) References Cited

OTHER PUBLICATIONS

Chien, N. C., et al., "Significant structural and functional change of an antigen-binding site by a distant amino acid substitution: Proposal of a structural mechanism," Proc. Natl. Acad. Sci. USA, 86: 5532-5536 (1989). Corrected Notice of Allowability for U.S. Appl. No. 13/126,734, entitled: "Methods and Agents for the Diagnosis and Treatment of Hepatocellular Carcinoma", dated Apr. 8, 2014.
Decision of Rejection for Japanese Patent Application No. 2011-500800, entitled: "Methods and Agents for the Diagnosis and Treatment of Hepatocellular Carcinoma," dated Jul. 7, 2014.
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," *J. Immunol.*, 169: 3076-3084 (2002).
Dennis, C., "Off by a whisker," *Nature*, 442: 739-741 (2006).
Final Office Action for U.S. Appl. No. 12/933,248, entitled: "Methods and Agents for the Diagnosis and Treatment of Hepatocellular Carcinoma", dated Nov. 22, 2013.
Giusti, A. M., et al., "Somatic diversification of S107 from an antiphosphocholine to an anti-DNA autoantibody is due to a single base change in its heavy chain variable region," *Proc. Natl. Acad. Sci. USA*, 84: 2926-2930 (1987).
Gotoh, K., et al., "Apg-2 has a chaperone-like activity similar to Hsp110 and is overexpressed in hepatocellular carcinomas," *FEBS Letters*, 560: 19-24 (2004).
Gray, D., et al., "Maternal Embryonic Leucine Zipper Kinase/Murine Protein Serine-Threonine Kinase 38 is a Promising Therapeutic Target for Multiple Cancers," *Cancer Res.*, 65(21): 9751-9761 (2005).
Gura, T., "Systems for Identifying New Drugs Are Often Faulty," *Science*, 278: 1041-1042 (1997).
Güssow, D., and Seemann, G., "Humanization of Monoclonal Antibodies," *Methods in Enzymology*, 203: 99-121 (1991).
Hayward, D. G., et al., "The Centrosomal Kinase Nek2 Displays Elevated Levels of Protein Expression in Human Breast Cancer," *Cancer Research*, 64: 7370-7376 (2004).
Hegmans, J. P. J. J., et al., "Proteomic Analysis of Exosomes Secreted by Human Mesothelioma Cells," *Am. J. Pathol.*, 164(5): 1807-1815 (2004).
Henry, M. D., et al., "A Prostate-Specific Membrane Antigen-Targeted Monoclonal Antibody-Chemotherapeutic Cojugate Designed for the Treatment of Prostate Cancer," *Cancer Research*, 64: 7995-8001 (2004).
Ho, S., et al., "Internal Radiation Therapy for Patients with Primary or Metastatic Hepatic Cancer," *Cancer*, 83: 1894-1907 (1998).
Holm, P., et al., "Functional mapping and single chain construction of the anti-cytokeratin 8 monoclonal antibody TS1," *Molecular Immunology*, 44: 1075-1084 (2007).
"*Homo sapiens* plasmalemma vesicle associated protein (PLVAP), mRNA." GenBank [online] [retreived on Jan. 26, 2011]. Retreived from the Internet URL: http://www.ncbi.nlm.nih.gov/nuccore/13775237?sat=OLD06&satkey=7209055.
International Preliminary Report on Patentability from International Application No. PCT/US2009/001689, entitled: "Methods and Agents for the Diagnosis and Treatment of Hepatocellular Carcinoma," dated Sep. 30, 2010.
International Preliminary Report on Patentability from International Application No. PCT/US2009/002196, entitled: "Methods, Agents and Kits for the Detection of Cancer," dated Oct. 12, 2010.
International Preliminary Report on Patentability from International Application No. PCT/US2009/056382, entitled: "Methods and Agents for the Diagnosis and Treatment of Hepatocellular Carcinoma," dated May 12, 2011.
International Search Report and Written Opinion of the International Searching Authority from International Application No. PCT/US2009/001689, entitled: "Methods and Agents for the Diagnosis and Treatment of Hepatocellular Carcinoma," dated Jul. 23, 2009.
International Search Report and Written Opinion of the International Searching Authority from International Application No. PCT/US2009/002196, entitled: "Methods, Agents and Kits for the Detection of Cancer," dated Jul. 24, 2009.
International Search Report and Written Opinion of the International Searching Authority from International Application No. PCT/US2009/056382, entitled: "Methods and Agents for the Diagnosis and Treatment of Hepatocellular Carcinoma," dated Dec. 21, 2009.
Invitation to Correct Deficiencies for European Patent Application No. 09723224.3, entitled: "Methods and Agents for the Diagnosis and Treatment of Hepatocellular Carcinoma," dated Nov. 3, 2010.
Invitation to Correct Deficiencies for European Patent Application No. 09729296.5, entitled: "Methods, Agents and Kits for the Detection of Cancer," dated Nov. 18, 2010.
Jiang, B., et al., "A Novel Peptide Isolated from a Phage Display Peptide Library with Trastuzumab Can Mimic Antigen Epitope of HER-2," *J. Biol. Chem.*, 280(6): 4656-4662 (2005).
Kelland, L. R., "'Of mice and men': values and liabilities of the athymic nude mouse model in anticancer drug development," *Eur. J. Cancer*, 40: 827-836 (2004).
Keuschnigg, J., et al., "The prototype endothelial marker PAL-E is a leukocyte trafficking molecule," *Blood*, 114: 478-484 (2009).
Lee, J.-S., et al., "Classification and Prediction of Survival in Hepatocellular Carcinoma by Gene Expression Profiling," *Hepatology*, 40: 667-676 (2004).
Lin, M.-L., et al., "Involvement of maternal embryonic leucine zipper kinase (MELK) in mammmary carcinogenesis through interaction with Bcl-G, a pro-apoptotic member of the Bcl-2 family," *Breast Cancer Research*, 9: R17 (2007).
Liu, Z., et al., "Fine mapping of the antigen-antibody interaction of scFv215, a recombinant antibody inhibiting RNA polymerase II from *Drosophila melanogaster*," *J. Mol. Recognit.*, 12: 103-111 (1999).
MacCallum, R. M., et al., "Antibody-antigen Interactions: Contact Analysis and Binding Site Topography," *J. Mol. Biol.*, 262: 732-745 (1996).
Mariuzza, R. A., et al., "The Structural Basis of Antigen-Antibody Recognition," *Ann. Rev. Biophys. Biophys. Chem.*, 16: 139-159 (1987).
McDevitt, M. R., et al., "An α-Particle Emitting Antibody ([$^{213}$Bi]J591) for Radioimmunotherapy of Prostate Cancer," *Cancer Research*, 60: 6095-6100 (2000).
Non-Final Office Action for U.S. Appl. No. 12/933,248, entitled: "Methods and Agents for the Diagnosis and Treatment of Hepatocellular Carcinoma", dated May 21, 2013.
Non-Final Office Action for U.S. Appl. No. 13/126,734, entitled: "Methods and Agents for the Diagnosis and Treatment of Hepatocellular Carcinoma", dated Aug. 28, 2013.
Non-Final Office Action for U.S. Appl. No. 14/335,129, entitled: "Methods and Agents for the Diagnosis and Treatment of Hepatocellular Carcinoma", dated Feb. 19, 2016.
Non-Final Office Action for U.S. Appl. No. 14/336,441, entitled: "Methods and Agents for the Diagnosis and Treatment of Hepatocellular Carcinoma", dated Dec. 30, 2015.
Notice of Abandonment for U.S. Appl. No. 12/937,207, entitled: "Methods, Agents and Kits for the Detection of Cancer", dated Sep. 26, 2013.
Notice of Allowance for U.S. Appl. No. 12/933,248, entitled: "Methods and Agents for the Diagnosis and Treatment of Hepatocellular Carcinoma", dated Feb. 14, 2014.
Notice of Allowance for U.S. Appl. No. 13/126,734, entitled: "Methods and Agents for the Diagnosis and Treatment of Hepatocellular Carcinoma", dated Mar. 12, 2014.
Notice of Allowance for U.S. Appl. No. 14/335,129, entitled: "Methods and Agents for the Diagnosis and Treatment of Hepatocellular Carcinoma", dated Sep. 13, 2016.
Notice of Allowance for U.S. Appl. No. 14/336,441, entitled: "Methods and Agents for the Diagnosis and Treatment of Hepatocellular Carcinoma", dated Apr. 12, 2016.
Notice of Intention to Grant for European Patent Application No. 09723224.3, entitled: "Methods and Agents for the Diagnosis and Treatment of Hepatocellular Carcinoma," dated Apr. 11, 2014.

(56) References Cited

OTHER PUBLICATIONS

Nuyten, D. S. A., et al., "Using Microarray Analysis as a Prognostic and Predictive Tool in Oncology: Focus on Breast Cancer and Normal Tissue Toxicity," *Seminars in Radiation Oncology*, 18: 105-114 (2008).
Office Action for Australian Patent Application No. 2009226152, entitled: "Methods and Agents for the Diagnosis and Treatment of Hepatocellular Carcinoma," dated Dec. 13, 2011.
Office Action for Australian Patent Application No. 2009/234444, entitled: "Methods, Agents and Kits for the Detection of Cancer," dated Jan. 19, 2012.
Office Action for Australian Patent Application No. 2009226152, entitled: "Methods and Agents for the Diagnosis and Treatment of Hepatocellular Carcinoma," dated May 31, 2012.
Office Action for Chinese Patent Application No. 200980118081.2, entitled: "Methods and Agents for the Diagnosis and Treatment of Hepatocellular Carcinoma," dated May 30, 2013.
Office Action for Chinese Patent Application No. 200980118081.2, entitled: "Methods and Agents for the Diagnosis and Treatment of Hepatocellular Carcinoma," dated Aug. 30, 2012.
Office Action for European Patent Application No. 09723224.3, entitled: "Methods and Agents for the Diagnosis and Treatment of Hepatocellular Carcinoma," dated Jan. 7, 2013.
Office Action for European Patent Application No. 09723224.3, entitled: "Methods and Agents for the Diagnosis and Treatment of Hepatocellular Carcinoma," dated May 2, 2011.
Office Action for European Patent Application No. 09723224.3, entitled: "Methods and Agents for the Diagnosis and Treatment of Hepatocellular Carcinoma," dated Dec. 8, 2011.
Office Action for Japanese Patent Application No. 2011-500800, entitled: "Methods and Agents for the Diagnosis and Treatment of Hepatocellular Carcinoma," dated Aug. 21, 2013.
Office Action for New Zealand Patent Application No. 588587, entitled: "Methods and Agents for the Diagnosis and Treatment of Hepatocellular Carcinoma," dated Mar. 8, 2011.
Office Action for New Zealand Patent Application No. 588548, entitled: "Methods, Agents and Kits for the Detection of Cancer," dated Mar. 18, 2011.
Office Action for New Zealand Patent Application No. 588587, entitled: "Methods and Agents for the Diagnosis and Treatment of Hepatocellular Carcinoma," dated Jun. 11, 2012.
Office Action for New Zealand Patent Application No. 588587, entitled: "Methods and Agents for the Diagnosis and Treatment of Hepatocellular Carcinoma," dated Nov. 22, 2012.
Office Action for New Zealand Patent Application No. 588587, entitled: "Methods and Agents for the Diagnosis and Treatment of Hepatocellular Carcinoma," dated Oct. 11, 2012.
Office Action for Taiwanese Patent Application No. 098108921, entitled: "Methods and Agents for the Diagnosis and Treatment of Hepatocellular Carcinoma," dated Jun. 17, 2014.
Office Action for Taiwanese Patent Application No. 098131450, entitled: "Methods and Agents for the Diagnosis and Treatment of Hepatocellular Carcinoma," dated Apr. 28, 2014.
Office Action for Taiwanese Patent Application No. 098108921, entitled: "Methods and Agents for the Diagnosis and Treatment of Hepatocellular Carcinoma," dated Aug. 15, 2013.
Ørntoft, T. F., et al., "Genome-wide Study of Gene Copy Numbers, Transcripts, and Protein Levels in Pairs of Non-invasive and Invasive Human Transitional Cell Carconomas," *Molecular & Cellular Proteomics*, 1: 37-45 (2002).
Pettersen, R. D., et al., "CD47 Signals T Cell Death," *J. Immunol.*, 162: 7031-7040 (1999).
Reply to Office Action issued in Australian Patent Application No. 2009226152, entitled: "Methods and Agents for the Diagnosis and Treatment of Hepatocellular Carcinoma," filed Apr. 26, 2012.
Reply to Office Action issued in Chinese Patent Application No. 200980118081.2, entitled: "Methods and Agents for the Diagnosis and Treatment of Hepatocellular Carcinoma," filed on or before Feb. 12, 2013.
Reply to Office Action issued in European Patent Application No. 09723224.3, entitled: "Methods and Agents for the Diagnosis and Treatment of Hepatocellular Carcinoma," filed Dec. 7, 2010.
Reply to Office Action issued in European Patent Application No. 09723224.3, entitled: "Methods and Agents for the Diagnosis and Treatment of Hepatocellular Carcinoma," filed Aug. 30, 2011.
Reply to Office Action issued in European Patent Application No. 09723224.3, entitled: "Methods and Agents for the Diagnosis and Treatment of Hepatocellular Carcinoma," filed May 24, 2012.
Reply to Office Action issued in European Patent Application No. 09729296.5, entitled: "Methods, Agents and Kits for the Detection of Cancer," filed Dec. 14, 2010.
Reply to Office Action issued in European Patent Application No. 09723224.3, entitled: "Methods and Agents for the Diagnosis and Treatment of Hepatocellular Carcinoma," filed Jul. 12, 2013.
Reply to Office Action issued in New Zealand Patent Application No. 588587, entitled: "Methods and Agents for the Diagnosis and Treatment of Hepatocellular Carcinoma," filed Dec. 14, 2012.
Reply to Office Action issued in New Zealand Patent Application No. 588587, entitled: "Methods and Agents for the Diagnosis and Treatment of Hepatocellular Carcinoma," filed May 18, 2012.
Reply to Office Action issued in New Zealand Patent Application No. 588587, entitled: "Methods and Agents for the Diagnosis and Treatment of Hepatocellular Carcinoma," filed Sep. 27, 2012.
Reply to Office Action issued in New Zealand Patent Application No. 588587, entitled: "Methods and Agents for the Diagnosis and Treatment of Hepatocellular Carcinoma," filed Nov. 9, 2012.
Reply to Office Action issued in U.S. Appl. No. 12/933,248, entitled: "Methods and Agents for the Diagnosis and Treatment of Hepatocellular Carcinoma", filed Jan. 14, 2013.
Response to Rule 312 Communication for U.S. Appl. No. 13/126,734, entitled: "Methods and Agents for the Diagnosis and Treatment of Hepatocellular Carcinoma", dated Aug. 4, 2014.
Response to Rule 312 Communication for U.S. Appl. No. 14/336,441, entitled: "Methods and Agents for the Diagnosis and Treatment of Hepatocellular Carcinoma", dated May 20, 2016.
Restriction Requirement for U.S. Appl. No. 12/933,248, entitled: "Methods and Agents for the Diagnosis and Treatment of Hepatocellular Carcinoma", dated Nov. 5, 2012.
Rhodes, D. R., et al., "Large-scale meta-analysis of cancer microarray data identifies common transcriptional profiles of neoplastic transformation and progression," *PNAS*, 101(25): 9309-9314 (2004).
Rudikoff, S., et al., "Single amino acid substitution altering antigen-binding specificity," *Proc. Natl. Acad. Sci. USA*, 79: 1979-1983 (1982).
Saijo, N., "What are the reasons for negative phase III trials of molecular-target-based drugs?" *Cancer Sci.*, 95: 772-776 (2004).
Schier, R., et al., "Isolation of Picomolar Affinity Anti-c-erbB-2 Single-chain Fv by Molecular Evolution of the Complementarity Determining Regions in the Center of the Antibody Binding Site," *J. Mol. Biol.*, 263: 551-567 (1996).
Stan, R.-V., et al., "Immunoisolation and Partial Characterization of Endothelial Plasmalemmal Vesicles (Caveolae)," *Molecular Biology of the Cell*, 8: 595-605 (1997).
Stan, R. V., et al., "PV1 is a Key Structural Component for the Formation of the Stomatal and Fenestral Diaphragms," *Molecular Biology of the Cell*, 15: 3615-3630 (2004).
Stancovski, I., et al., "Mechanistic aspects of the opposing effects of monoclonal antibodies to the ERBB2 receptor on tumor growth," *Proc. Natl. Acad. Sci. USA*, 88: 8691-8695 (1991).
Strickland, L. A., et al., "Plasmalemmal vesicle-associated protein (PLVAP) is expressed by tumour endothelium and is upregulated by vascular endothelial growth factor-A (VEGF)," *J. Pathol.*, 206: 466-475 (2005).
Thorgeirsson, S. S., et al., "Molecular prognostication of liver cancer: End of the beginning," *Journal of Hepatology*, 44: 798-805 (2006).
Vajdos, F. F., et al., "Comprehensive Functional Maps of the Antigen-binding Site of an Anti-ErbB2 Antibody Obtained with Shotgun Scanning Mutagenesis," *J. Mol. Biol.*, 320: 415-428 (2002).
Van 't Veer, L. J., et al., "Gene expression profiling predicts clinical outcome of breast cancer," *Nature*, 415: 530-536 (2002).

(56) References Cited

OTHER PUBLICATIONS

Winkler, K., et al., "Changing the Antigen Binding Specificity by Single Point Mutations of an Anti-p24 (HIV-1) Antibody," *J. Immunol.*, 165: 4505-4514 (2000).
Wolff, A. C., et al., "American Society of Clinical Oncology/College of American Pathologists Guideline Recommendations for Human Epidermal Growth Factor Receptor 2 Testing in Breast Cancer," *Arch. Pathol. Lab. Med.*, 131: 18-43 (2007).
Wu, H., et al., "Humanization of a Murine Monoclonal Antibody by Simultaneous Optimization of Framework and CDR Residues," *J. Mol. Biol.*, 294(1): 151-162 (1999).
Developmental Studies Hybridoma Bank (search for MECA-32 antibody; pp. 1-12; Jul. 31, 2018).
Din, H. et al., "Relationship between Tissue Factor Expression and Angiogenesis of Hepatocellular Carcinoma and its Clinical Significance," J. Hepatopancreatobiliary Surgery, vol. 20, No. 5, pp. 331-335 (2008).
Final Office Action from U.S. Appl. No. 15/270,430, dated Aug. 6, 2018.
Frankel, A.E. et al., "Characterization of diphtheria fusion proteins targeted to the human interleukin-3 receptor," Protein Engineering, vol. 13; No. 8; 575-581 (2000).
Herrnberger, L. et al., "The role of plasmalemma vesicle-associated protein (PLVAP) in endothelial cells of Schlemm's canal and ocular capillaries," Experimental Eye Research, vol. 105; 27-33 (2012).
Hu P. et al., "Comparison of the Three Different Targeted Tissue Factor Fusion Proteins for Inducing a Tumor Vessel Thrombosis," Cancer Research, vol. 63; No. 16; 5046-5053 (2003).
Huang, X., et al., "Tumor Infarction in Mice by Antibody-Directed Targeting of Tissue Factor to Tumor Vasculature", Science, 275: 547-550 (1997).
Huang, Z. et al., "Humanised monoclonal antibody TNT-3 mediated truncated tissue factor for the treatment of H22 hepatoma-bearing mice," Chin J Oncol., vol. 34; No. 4; 249-253 (2012).
Nishi, Y., et al., "Histopathological manifestations of membranoproliferative glomerulonephritis and glomerular expression of plasmalemmal vesicle-associated protein-1 in a patient with polycythemia vera," Clinical Nephrology, vol. 74; 393-398 (2010).
Office Action from U.S. Appl. No. 15/270,430, dated Mar. 2, 2018.
Pakula, A.A., "Genetic Analysis of Protein Stability and Function," Annu. Rev. Genet., vol. 23; 289-310 (1989).
Rantakari, P. et al., "The endothelial protein PLVAP in lymphatics controls the entry of lymphocytes and antigens into lymph nodes," Nature immunology, vol. 16; No. 4; 386-401 (2015).
Shchegolev A.A. et al., Vascularization of the tissue of hepatocellular carcinoma depends on the degree of its differentiation, Bulletin of Experimental Biology and Medicine, 2012, p. 153, N. 4, p. 480-484, Full Text.
Singapore International Search Report for Application No. 10201407557V, entitled: "Therapeutic Biologic for Treatment of Hepatocellular Carcinoma ," dated Aug. 8, 2017.
Skerra, A. et al., "Assembly of a Functional Immunoglobulin Fv Fragment in *Escherichia coli*," Science, vol. 240; 1038-1041 (1988).
Sotiriou, C. et al., "Gene Expression Profiling in Breast Cancer: Understanding the Molecular Basis of Histologic Grade to Improve Prognosis," Journal of the National Cancer Institute, vol. 98; No. 4; 262-272 (2006).
"Survival Rates for Liver Cancer", 2 pages. URL: http://www/cancer.org/camcer/livercancer/detailedguide/liver-cancer-survival-rates, downloaded from American Cancer Society website on Aug. 25, 2015. "Survival Rates for Liver Cancer", 2 pages. URL: http://www/cancer.org/camcer/livercancer/detailedguide/liver-cancer-survival-rates, downloaded from American Cancer Society website on Aug. 25, 2015. "Survival Rates for Liver Cancer", 2 pages. URL: http://www/cancer.org/camcer/livercancer/detailedguide/liver-cancer-survival-rates, downloaded from American Cancer Society website on Aug. 25, 2015.
Brorson K., et al., "Mutational Analysis of Avidity and Fine Specificity of Anti-Levan Antibodies", J. Immunol. 163; 6694-6701 (1999).

Bruix, J. and Sherman, M., "Management of Hepatocellular Carcinoma: An Update", Hepatology, 53(3): 1020-1022 (2011).
Brummell et al., "Probing the combining site of an anti-carbohydrate antibody by saturation-mutagensis: role of the heavy chain DCR3 residues", Biochemistry 32; 1180-1187 (1993).
Burks et al., "In vitro scanning saturation mutagenesis of an antibody binding pocket", PNAS 94; 412-417 (1997).
Burrows, F.J., et al., "A Murine Model for Antibody-Directed Targeting of Vascular Endothelial Cells in Solid Tumors", Cancer Research, 52: 5954-5962 (1992).Huang, X., et al., "Tumor Infarction in Mice by Antibody-Directed Targeting of Tissue Factor to Tumor Vasculature", Science, 275: 547-550 (1997).
Colman, "A Structural View of Immune Recognition by antibodies", Research in Immunol. 145; 33-36 (1994).
Final Office Action from U.S. Appl. No. 14/539,577, entitled: "Therapeutic Biologic for Treatment of Hepatocellular Carcinoma", dated Apr. 18, 2016.
Interview Summary for U.S. Appl. No. 12/933,248, entitled: "Methods and Agents for the Diagnosis and Treatment of Hepatocellular Carcinoma", dated May 29, 2014.
Interview Summary for U.S. Appl. No. 13/126,734, Entitled: "Methods and Agents for the Diagnosis and Treatment of Hepatocellular Carcinoma", dated Feb. 6, 2014.
Jang et al., "The structural basis for DNA binding by an anti-DNA autoantibody", Molec. Immunol. 35; 1207-1217 (1998).
Jemal, A., et al., "Global Cancer Statistics", CA Cancer J Clin, 51: 69-90 (2011).
Kobayashi et al., "Tryptophan H33 plays an important role in pyrimidine (6-4) pyrimidone photoproduct binding by a high-affinity antibody", Protein Engineering 12; 879-844 (1999).
Llovet, J.M., et al., "Systematic Review of Randomized Trials for Unresectable Hepatocellular Carcinoma: Chemoembolization Improves Survival", Hepatology, 37: 429-442 (2003).
Llovet, J.M., et al., "Sorafenib in Advanced Hepatocellular Carcinoma", The New England Journal of Medicine, 359: 378-390 (2008).
Mackman, Nigel, "Role of Tissue Factor in Hemostasis, Thrombosis, and Vascular Development", Arterioscler Thromb Vasc Biol, 24: 1015-1022 (2004).
Madden, S.L., et al., "Vascular Gene Expression in Nonneoplastic and Malignant Brain", American Journal of Pathology, 165(2): 601-608 (2004).
Murata, S., et al., "Transcatheter Arterial Chemoembolization Based on Hepatic Hemodynamics for Hepatocellular Carcinoma", The Scientific World Journal, Article ID 479805; 8 pages (2013).
Notice of Allowance for U.S. Appl. No. 14/539,577, entitled: "Therapeutic Biologic for Treatment of Hepatocellular Carcinoma", dated Jun. 30, 2016.
Office Action from U.S. Appl. No. 14/539,577, entitled: "Therapeutic Biologic for Treatment of Hepatocellular Carcinoma", dated Jan. 8, 2016.
Perz, J.F., et al., "The Contributions of Hepatitis B Virus and Hepatitis C virus Infections to Cirrhosis and Primary Liver Cancer Worldwide", Journal of Hepatology, 45: 529-538 (2006).
Petersen, L.C., et al., "Characterization of Recombinant Murine Factor IIa and Recombinant Murine Tissue Factor: A Human-Murine Compatibility Study", Thrombosis Res, 116: 75-85 (2005).
Philipp, J., et al., "Soluble Tissue Factor Induces Coagulation on Tumor Endothelial Cells In Vivo if Coadministered With Low-Dose Lipopolysaccharides", Arterioscler Thromb Vasc Biol, 23: 905-910 (2003).
Siegel, R., et al., "Cancer Statistics, 2012", CA Cancer J Clin, 62: 10-29 (2012).
Simard, E.P., et al., "Cancers With Increasing Incidence Trends in the United States: 1999 Through 2008", CA Cancer J Clin, 62: 118-128 (2012).
Simonetti, R.G., et al., "Hepatocellular Carcinoma. A Worldwide Problem and the Major Risk Factors", Dig Dis Sci, 36: 962-972 (1991).
Snyder, L.A., et al., "Expression of Human Tissue Factor Under the Control of the Mouse Tissue Factor Promoter Mediates Normal Hemostasis in Knock-In Mice", Journal of Thrombosis and Haemostasis, 6: 306-314 (2007).

(56) References Cited

OTHER PUBLICATIONS

Stan, R.-V., et al., "PV-1 is a Component of the Fenestral and Stomatal Diaphragms in Fenestrated Endothelia", PNAS, 96(23): 13202-13207 (1999).

Wang et al., "Plasmalemmal Vesicle Associated Protein (PLVAP) as a therapeutic target for treatment of hepatocellular carcinoma", BMC Cancer 14: 815-826 (2014).

Office Action from U.S. Appl. No. 15/270,430, dated Nov. 13, 2018.

Ran, S. et al., "Infraction of Solid Hodgkin's Tumors in Mice by Antibody-directed Targeting of Tissue Factor to Tumor Vasculature," Cancer Research, vol. 58; 4646-4653 (1998).

```
  1 atgggcagcagccatcatcatcatcatcacagcagcggcctggtg
    M  G  S  S  H  H  H  H  H  H  S  S  G  L  V
 46 ccgcgcggcagccatatgaacgtgcacgtgagcacagagtccaac
    P  R  G  S  H  M  N  V  H  V  S  T  E  S  N
 91 ctgcaggccaccgagcgccgagccgagggcctatacagtcagctc
    L  Q  A  T  E  R  R  A  E  G  L  Y  S  Q  L
136 ctagggctcacggcctccagtccaacttgaccaaggagctcaac
    L  G  L  T  A  S  Q  S  N  L  T  K  E  L  N
181 ttcaccacccgcgccaaggatgccatcatgcagatgtggctgaat
    F  T  T  R  A  K  D  A  I  M  Q  M  W  L  N
226 gctcgccgcgacctggaccgcatcaatgccagcttccgccagtgc
    A  R  R  D  L  D  R  I  N  A  S  F  R  Q  C
271 cagggtgaccgggtcatctacacgaacaatcagaggtacatggct
    Q  G  D  R  V  I  Y  T  N  N  Q  R  Y  M  A
316 gccatcatcttgagtgagaagcaatgcagagatcaattcaaggac
    A  I  I  L  S  E  K  Q  C  R  D  Q  F  K  D
361 atgaacaagagctgcgatgccttgctcttcatgctgaatcagaag
    M  N  K  S  C  D  A  L  L  F  M  L  N  Q  K
406 gtgaagacgctggaggtggagatagccaaggagaagaccatttgc
    V  K  T  L  E  V  E  I  A  K  E  K  T  I  C
451 actaaggataaggaaagcgtgctgctgaacaaacgcgtggcggag
    T  K  D  K  E  S  V  L  L  N  K  R  V  A  E
496 gaacagctggttgaatgcgtgaaaacccgggagctgcagcaccaa
    E  Q  L  V  E  C  V  K  T  R  E  L  Q  H  Q
541 gagcgccagctggccaaggagcaactgcaaaaggtgcaagccctc
    E  R  Q  L  A  K  E  Q  L  Q  K  V  Q  A  L
586 tgcctgcccctggacaaggacaagtttgagatggaccttcgtaac
    C  L  P  L  D  K  D  K  F  E  M  D  L  R  N
631 ctgtggagggactccattatcccacgcagcctggacaacctgggt
    L  W  R  D  S  I  I  P  R  S  L  D  N  L  G
676 tacaacctctaccatcccctgggctcggaattggcctccatccgc
    Y  N  L  Y  H  P  L  G  S  E  L  A  S  I  R
721 agagcctgcgaccacatgcccagcctcatgagctccaaggtggag
    R  A  C  D  H  M  P  S  L  M  S  S  K  V  E
766 gagctggcccggagcctccgggcggatatcgaacgcgtggcccgc
    E  L  A  R  S  L  R  A  D  I  E  R  V  A  R
811 gagaactcagacctccaacgccagaagctggaagcccagcagggc
    E  N  S  D  L  Q  R  Q  K  L  E  A  Q  Q  G
856 ctgcgggccagtcaggaggcgaaacagaaggtggagaaggaggct
    L  R  A  S  Q  E  A  K  Q  K  V  E  K  E  A
901 caggcccgggaggccaagctccaagctgaatgctcccggcagacc
    Q  A  R  E  A  K  L  Q  A  E  C  S  R  Q  T
946 cagctagcgctggaggagaaggcggtgctgcggaaggaacgagac
    Q  L  A  L  E  E  K  A  V  L  R  K  E  R  D
991 aacctggccaaggagctggaagagaagaagagggaggcggagcag
```

FIG. 4A

```
          N   L   A   K   E   L   E   E   K   K   R   E   A   E   Q
1036  ctcaggatggagctggccatcagaaactcagccctggacacctgc
          L   R   M   E   L   A   I   R   N   S   A   L   D   T   C
1081  atcaagaccaagtcgcagccgatgatgccagtgtcaaggcccatg
          I   K   T   K   S   Q   P   M   M   P   V   S   R   P   M
1126  ggccctgtccccaaccccagcccatcgacccagctagcctggag
          G   P   V   P   N   P   Q   P   I   D   P   A   S   L   E
1171  gagttcaagaggaagatcctggagtcccagaggccccctgcaggc
          E   F   K   R   K   I   L   E   S   Q   R   P   P   A   G
1216  atccctgtagccccatccagtggctga
          I   P   V   A   P   S   S   G   *   (SEQ ID NO:2)
      ggaggctccaggcctgaggaccaagggatggcccgactcggcggt ttgcggaggatgcagggatatgctcacag ggattc (SEQ ID NO:1)
```

FIG. 4B

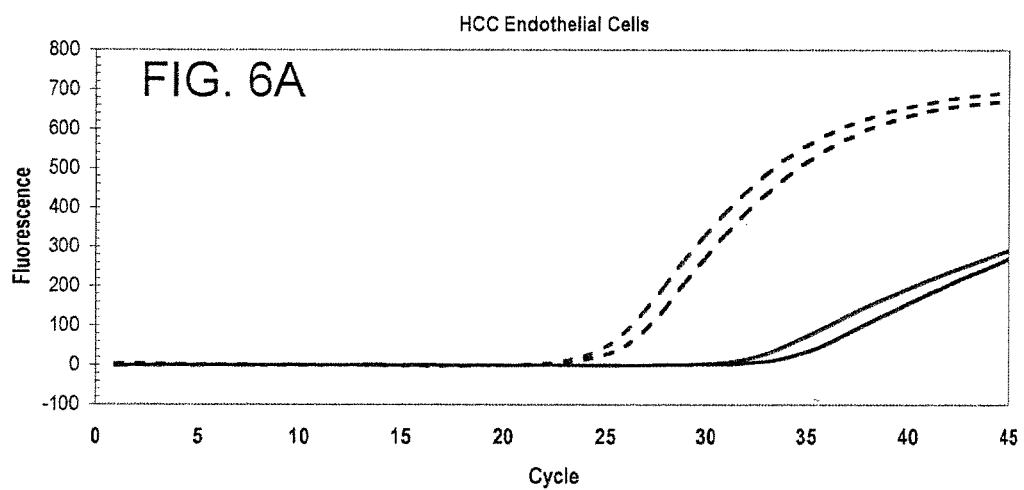
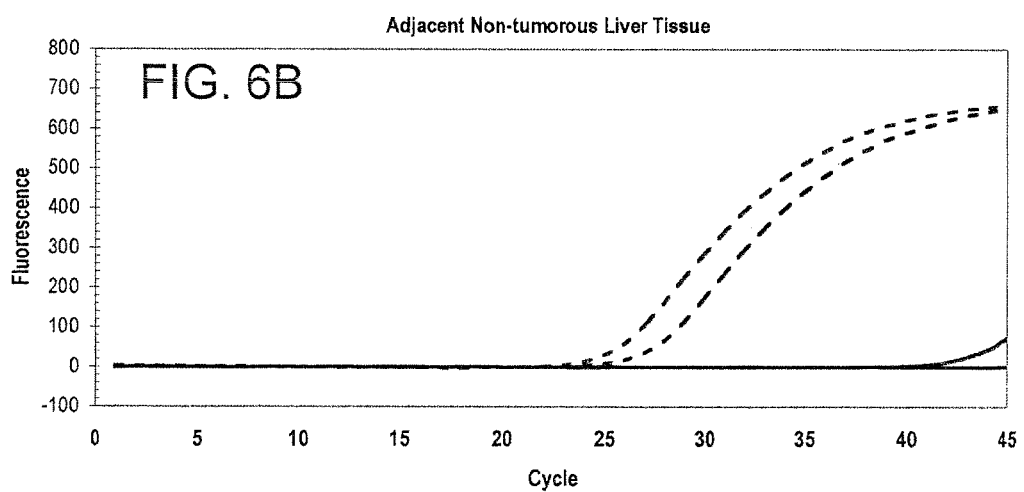
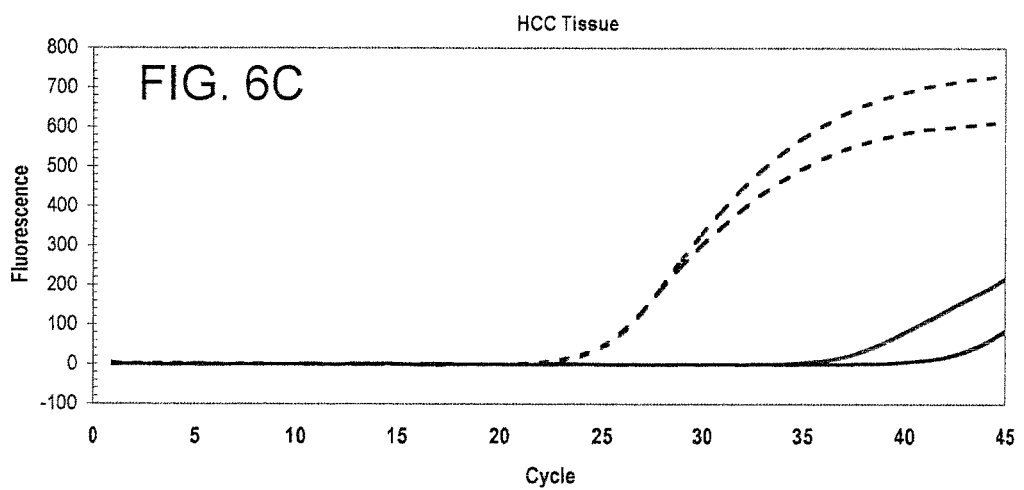

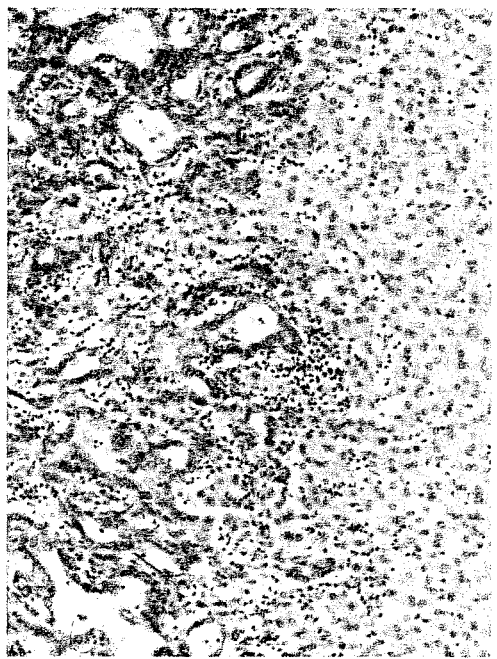
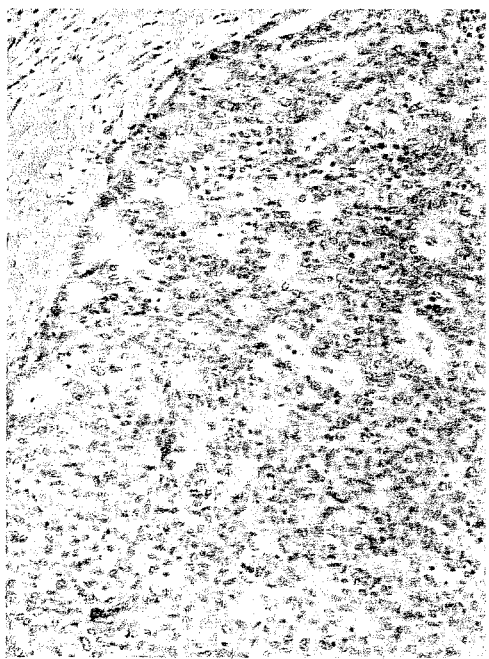
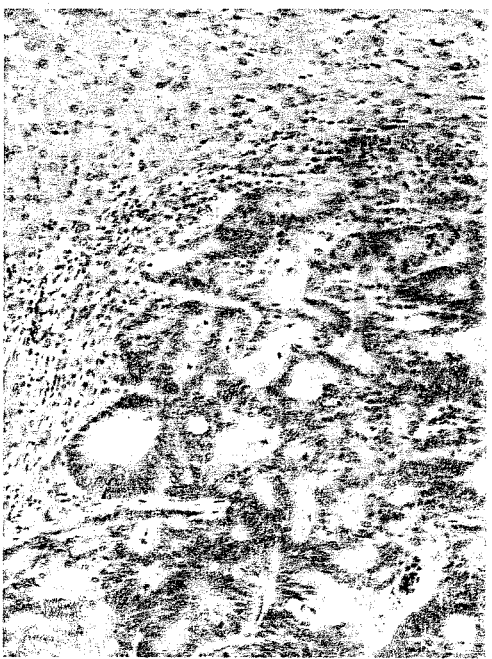
FIG. 14A
FIG. 14B
FIG. 14C
FIG. 14D

GAGGTTCAGCTGCAGCAGTCTGGGGCAGAGCTTGTGAGGTCAGGGGCCTCAGTCAAGTTGTCCTGCACAGCTTCTGGCTTCAACATTAA 90
GACTACTATATACACTGGGTGAAGCAGAGGCCTGAACAGGGCCTGGAGTGGATTGGATGGATTGATCCTGAGAATGGTGATATTGAATA T 180
GCCCCGAAGTTCCAGGGCAAGGCCACTATGACTGCAGACACATCCTCCAATACAGCCTACCTGCAGTTCAGCAGCCTGACATCTGAGGA C 270
ACTGCCGTCTATTACTGTCTCTACCAAGAAGGCTCCTGGGGCCAAGGCACCACTCTCACAGTCTCCTCAGCC 342 (SEQ ID NO:3)

E V Q L Q Q S G A E F V R S G A S V K L S C T A S G F N I K
D Y Y I H W V K Q R P E Q G L E W I G W I D P E N G D I E Y
     CDR1                                    CDR2
A P K F Q G K A T M T A D T S S N T A Y L Q F S S L T S E D
T A V Y Y C L Y Q E G S W G Q G T T L T V S S A (SEQ ID NO:4)
              CDR3

CDR1: D Y Y I H (SEQ ID NO:5)
CDR2: W I D P E N G D I E Y A P K F Q G (SEQ ID NO:6)
CDR3: Q E G S (SEQ ID NO:7)

FIG. 15A

```
GATGTTGTGATGACCCAGACTCCACTCACTTTGTCGGTTACCATTGGACAACCAGCCTCCATCTCTTGCAAGTCAAGTCAGAGCCTCTT
A 90
AATAGTGATGGAAAGACATATTTGAATTGGTTGTTACAGAGGCCAGGCCAGTCTCCAAAGCGCCTAATCTATCTGGTGTCTAAATTGGA
C 180
TCTGGAGTCCCTGACAGGTTCACTGGCAGTGGATCAGGGACAGATTTCACACTGAAAATCAGCAGAGTGGAGGCTGAGGATTTGGGAGT
T 270
TATTATTGCTGGCAAGGTACACATTTTCCGTTCACGTTCGGAGGGGGACCAAGCTGAAATAAAA   336   (SEQ ID NO:8)
```

```
D  V  V  M  T  Q  T  P  L  T  L  S  V  T  I  G  Q  P  A  S  I  S  C  K  S  S  Q  S  L  L
N  S  D  G  K  T  Y  L  N  W  L  Q  R  P  G  Q  S  P  K  R  L  I  Y  L  V  S  K  L  D
                        CDR1                                              CDR2

S  G  V  P  D  R  F  T  G  S  G  S  G  T  D  F  T  L  K  I  S  R  V  E  A  E  D  L  G  V
_

Y  Y  C  W  Q  G  T  H  F  P  F  T  F  G  G  G  T  K  L  E  I  K   (SEQ ID NO:9)
              CDR3
```

CDR1: K S S Q S L L N S D G K T Y L N (SEQ ID NO:10)
CDR2: L V S K L D S (SEQ ID NO:11)
CDR3: W Q G T H F P F T (SEQ ID NO:12)

FIG. 15B

CAGGTCCAACTGCAGCAGCCTGGGGCTGAGCTGGTGAGGCCTGGGGCTTCAGTGAAGCTGTCCTGCAAGGCTTCTGGCTACACCTTCAC
C  90
AGCAACTACATAAACTGGGTGAAACAGAGGCCTGACAGGGCCTTGAGTGGATGGAAATATTTATCCTTCTGATGGTTTTACTAACTA
C  180
AATCAAAAGTTCAAGGACAGGGCCACATTGACTGTAGACAAATCCTCCAGCACCTACATGCAGCTCAGCAGCCCGACATCTGAGGA
C  270
TCTGCGGTCTATTACTGTACAAGAAACTTCGATGTCTGGGGCGCAGGGACCACGGTCACCGTCTCCTCAGCC 342 (SEQ ID NO:13)

Q V Q L Q Q P G A E L V R P G A S V K L S C K A S G Y T F T
S N Y I N W V K Q R P G Q G L E W I G N I Y P S D G F T N Y
    CDR1                                                    CDR2
N Q K F K D R A T L T V D K S S S T A Y M Q L S S P T S E D
S A V Y Y C T R N F D V W G A G T T V T V S S A (SEQ ID NO:14)
               CDR3

CDR1: S N Y I N (SEQ ID NO:15)
CDR2: N I Y P S D G F T N Y N Q K F K D (SEQ ID NO:16)
CDR3: N F D V (SEQ ID NO:17)

FIG. 16A

```
GATGTTGTGATGACCCAAACTCCACTCTCCCTGCCTGTCAGTCTTGGAGATCAAGCCTCCATCTCTTGCAGATCTAGTCAGAGCCTTGT
C    90
CACAGTAATGGAAACACCTATTTACAGTGGTACCTGCAGAAGCCAGGCCAGTCTCCAAAGCTCCTGATCTACACAGTTTCCAACCGATT
T   180
TCTGGGGTCCCAGACAGGTTCAGTGGCAGTGGATCAGGGACAGATTTCACACTCAAGATCAGCAGAGTGGAGGCTGAGGATCTGGGAGT
T   270
TATTTCTGCTCTCAAAGTACACATGTTCCTTTCACGTTCCGGCTCGGGGACAAAGTTGGAAATAAAA   336  (SEQ ID NO:18)
```

```
D  V  V  M  T  Q  T  P  L  S  L  P  V  S  L  G  D  Q  A  S  I  S  C  R  S  S  Q  S  L  V
                                                                     ‾‾‾‾‾‾‾‾‾‾‾‾‾‾‾‾‾‾‾‾
                                                                              CDR1
H  S  N  G  N  T  Y  L  Q  W  Y  L  Q  K  P  G  Q  S  P  K  L  L  I  Y  T  V  S  N  R  F
‾‾‾‾‾‾‾‾‾‾‾‾‾‾‾‾‾‾‾‾                                                 ‾‾‾‾‾‾‾‾‾‾‾‾‾‾‾‾‾‾‾‾
                                                                              CDR2
S  G  V  P  D  R  F  S  G  S  G  S  G  P  D  F  T  L  K  I  S  R  V  E  A  E  D  L  G  V
‾
Y  F  C  S  Q  S  T  H  V  P  F  T  F  G  S  G  T  K  L  E  I  K   (SEQ ID NO:19)
   ‾‾‾‾‾‾‾‾‾‾‾‾‾‾‾‾‾‾‾‾‾‾‾‾‾‾‾
               CDR3
```

CDR1: R S S Q S L V H S N G N T Y L Q  (SEQ ID NO:20)
CDR2: T V S N R F S  (SEQ ID NO:21)
CDR3: S Q S T H V P F T  (SEQ ID NO:22)

FIG. 16B

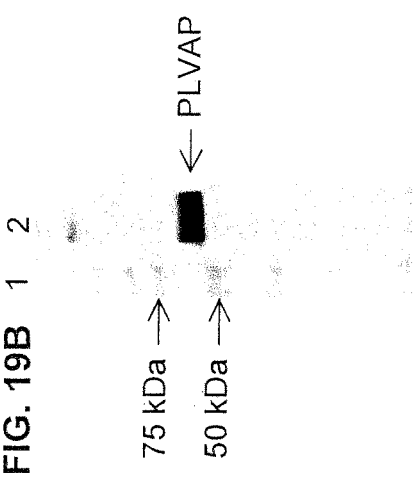
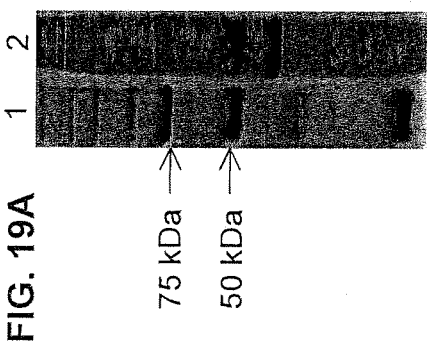
FIG. 19A
FIG. 19B
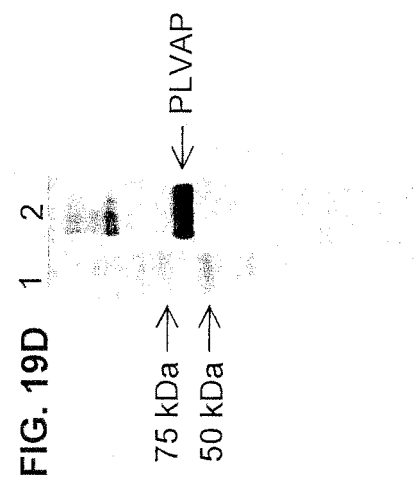
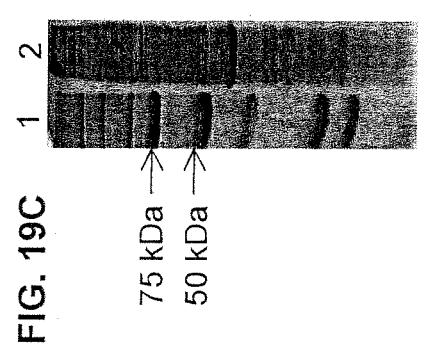
FIG. 19C
FIG. 19D

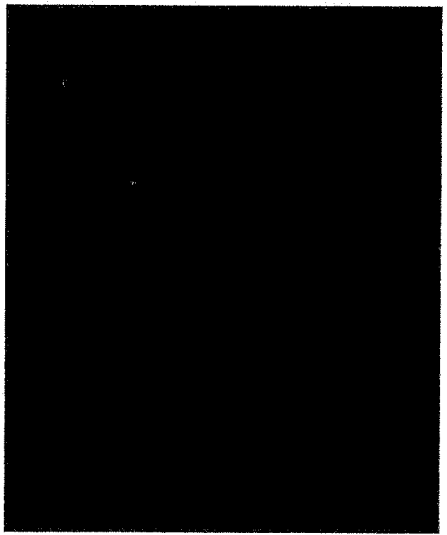
FIG. 20A Mouse IgG
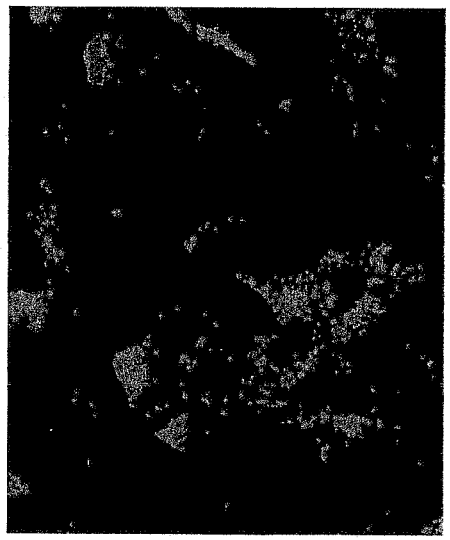
FIG. 20B Mouse vWF
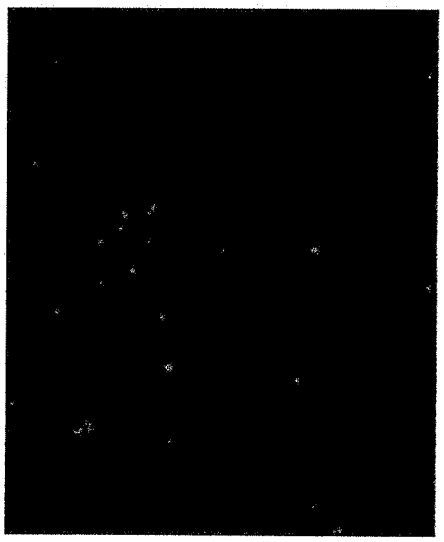
FIG. 20C KFCC-GY4
FIG. 20D KFCC-GY5

```
  1  mglamehggs yaraggssrg cwyylryffl fvsliqflii lglvlfmvyg nvhvstesnl
 61  qaterraegl ysqllgltas qsnltkelnf ttrakdaimq mwlnarrdld rinasfrqcq
121  gdrviytnnq rymaaiilse kqcrdqfkdm nkscdallfm lnqkvktlev eiakektict
181  kdkesvllnk rvaeeqlvec vktrelqhqe rqlakeqlqk vqalclpldk dkfemdlrnl
241  wrdsiiprsl dnlgynlyhp lgselasirr acdhmpslms skveelarsl radiervare
301  nsdlqrqkle aqqglrasqe akqkvekeaq areaklqaec srqtqlalee kavlrkerdn
361  lakeleekkr eaeqlrmela irnsaldtci ktksqpmmpv srpmgpvpnp qpidpaslee
421  fkrkilesqr ppagipvaps sg   (SEQ ID NO:23)
```

FIG. 24

```
1    cggacgcgtg ggtgagcagg gacggtgcac cggacggcgg gatcgagcaa atgggtctgg
61   ccatggagca cggagggtcc tacgctcggg cgggggggcag ctctcggggc tgctggtatt
121  acctgcgcta cttcttcctc ttcgtctccc tcatccaatt cctcatcatc ctggggctcg
181  tgctcttcat ggtctatggc aacgtgcacg tgagcacaga gtccaacctg caggccaccg
241  agcgccgagc cgagggccta tacagtcagc tcctagggct cacggcctcc cagtccaact
301  tgaccaagga gctcaacttc accacccgcg ccaaggatgc catcatgcag atgtggctga
361  atgctcgccg cgacctggac cgcatcaatg ccagcttccg ccagtgccag ggtgaccggg
421  tcatctacac gaacaatcag aggtacatgg ctgccatcat cttgagtgag aagcaatgca
481  gagatcaatt caaggacatg aacaagagct gcgatgcctt gctcttcatg ctgaatcaga
541  aggtgaagac gctggaggtg agatagcca aggagaagac catttgcact aaggataagg
601  aaagcgtgct gctgaacaaa cgcgtggcgg aggaacagct ggttgaatgc gtgaaaaccc
661  gggagctgca gcaccaagag cgccagctgg ccaaggagca actgcaaaag gtgcaagccc
721  tctgcctgcc cctggacaag gacaagtttg agatggacct tcgtaacctg tggagggact
781  ccattatccc acgcagcctg gacaacctgg gttacaacct ctaccatccc ctgggctcgg
841  aattggcctc catccgcaga gcctgcgacc acatgcccag cctcatgagc tccaaggtgg
901  aggagctggc ccggagcctc cgggcggata tcgaacgcgt ggcccgcgag aactcagacc
961  tccaacgcca gaagctggaa gcccagcagg cctgcgggc cagtcaggag gcgaaacaga
1021 aggtggagaa ggaggctcag gcccgggagg ccaagctcca agctgaatgc tcccggcaga
1081 cccagctagc gctggaggag aaggcggtgc tgcggaagga acgagacaac ctggccaagg
1141 agctggaaga gaagaagagg gaggcggagc agctcaggat ggagctggcc atcagaaact
1201 cagccctgga cacctgcatc aagaccaagt cgcagccgat gatgccagtg tcaaggccca
1261 tgggccctgt ccccaacccc cagcccatcg acccagctag cctggaggag ttcaagagga
1321 agatcctgga gtcccagagg ccccctgcag gcatccctgt agccccatcc agtggctgag
1381 gaggctccag gcctgaggac caagggatgg cccgactcgg cggtttgcgg aggatgcagg
1441 gatatgctca cagcgcccga cacaaccccc tcccgccgcc cccaaccacc cagggccacc
1501 atcagacaac tccctgcatg caaaccccta gtaccctctc acaccccgcac ccgcgcctca
1561 cgatccctca cccagagcac acggccgcgg agatgacgtc acgcaagcaa cggcgctgac
1621 gtcacatatc accgtggtga tggcgtcacg tggccatgta gacgtcacga agagatatag
1681 cgatggcgtc gtgcagatgc agcacgtcgc acacagacat ggggaacttg gcatgacgtc
```

FIG. 25A

```
1741 acaccgagat gcagcaacga cgtcacgggc catgtcgacg tcacacatat taatgtcaca
1801 cagacgcggc gatggcatca cacagacggt gatgatgtca cacacagaca cagtgacaac
1861 acacaccatg acaacgacac ctatagatat ggcaccaaca tcacatgcac gcatgccctt
1921 tcacacacac tttctaccca attctcacct agtgtcacgt tcccccgacc ctggcacacg
1981 ggccaaggta cccacaggat cccatccct cccgcacagc cctgggcccc agcacctccc
2041 ctcctccagc ttcctggcct cccagccact tcctcacccc cagtgcctgg acccggaggt
2101 gagaacagga agccattcac ctccgctcct tgagcgtgag tgtttccagg acccctcgg
2161 ggccctgagc cgggggtgag ggtcacctgt tgtcgggagg ggagccactc cttctccccc
2221 aactcccagc cctgcctgtg gcccgttgaa atgttggtgg cacttaataa atattagtaa
2281 atccttaaaa aaaaaaaaaa aaaaaaaaaa aaaaaaa (SEQ ID NO:24)
```

FIG. 25B

METHODS AND AGENTS FOR THE DIAGNOSIS AND TREATMENT OF HEPATOCELLULAR CARCINOMA

RELATED APPLICATIONS

This application is a divisional of U.S. application Ser. No. 14/335,129, filed Jul. 18, 2014, which is a divisional of U.S. application Ser. No. 12/933,248, now U.S. Pat. No. 8,815,240, filed on Dec. 15, 2010, which is the U.S. National Stage of International Application No. PCT/US2009/001689, filed on Mar. 18, 2009, which designates the U.S., published in English, and claims the benefit of U.S. Provisional Application No. 61/069,910, filed on Mar. 19, 2008.

The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

File name: 42611001038SEQLISTING.txt; created Oct. 6, 2016; 23 KB in size.

BACKGROUND OF THE INVENTION

Hepatocellular carcinoma (HCC) is the most frequent primary malignancy of the liver and is the fifth most common cancer in humans worldwide. HCC also is the fourth leading cause of cancer-related death (Parkin D M, Bray F, Ferlay J, Pisani P. Estimating the world cancer burden: Globocan 2000. Int J Cancer 2001; 94:153-156). In 1990, the World Health Organization estimated that there were about 430,000 new cases of liver cancer worldwide, and that a similar number of patients died that year as a result of this disease.

The pathogenesis of HCC has been associated with chronic hepatitis B virus (HBV) and hepatitis C virus (HCV) infections, as well as cirrhosis-inducing conditions of liver (Bruix J, et al. J Hepatol 35:421-430, 2001; Bruix J, et al. Cancer Cell 5:215-219, 2004). Accordingly, the incidence of HCC is highest in East Asian countries, such as China, Hong Kong, Taiwan, Korea, and Japan, where HBV and HCV infections are most prevalent (Bruix J, et al. Cancer Cell 5:215-219, 2004; Haskell C M. Chapter 46 Liver: Natural History, Diagnosis and Staging in "Cancer Treatment" 5$^{th}$ edition, W. B, Saunders Company, Philadelphia, editors: Haskell C M & Berek J S). However, the incidence of HCC in western countries is steadily increasing (Parkin D M, et al. Int J Cancer 94; 153-156, 2001). Over the past decade in the United States, HCC displayed the second highest increase in incidence, and the highest increase in death rate, of all cancers (Ann Int Med 139:817-823, 2003). Thus, in the United States and throughout the world, HCC is a major cause of mortality and morbidity, and a significant economic burden due to hospital costs and loss of work by people with HCC.

Successful control of HCC requires correct diagnosis of the disease at an early stage of disease progression. However, distinguishing small HCC tumors from other malignant or non-malignant liver diseases, including metastatic tumors, cholangiocarcinoma, focal nodular hyperplasia, dysplastic and regenerating liver nodules, using current techniques, such as imaging studies, needle core biopsy and/or fine needle aspiration, has proven to be challenging (Ferrell L D, et al. Am J Surg Pathol 17:1113-1123, 1993; Horigome H, et al. Hepato-Gatroenterology 47:1659-1662, 2000; Kalar S, et al. Arch Pathol Lab Med 131:1648-1654, 2007; Seki S, et al. Clin Cancer Res 6:3460-3473, 2000). Moreover, attempts to treat HCC therapeutically have been largely unsuccessful (Bruix J, et al. J Hepatol 35:421-430, 2001; Bruix J, et al. Cancer Cell 5:215-219, 2004; Haskell C M. Chapter 46 Liver: Natural History, Diagnosis and Staging in "Cancer Treatment" 5$^{th}$ edition, W. B, Saunders Company, Philadelphia, editors: Haskell C M & Berek J S; Szklaruk J, et al. AJR 180:441-453, 2003). As a result, despite active therapy, the 5-year survival rate of patients with HCC in the U.S. is only 10.5%, which is second in magnitude only to pancreatic cancer (ACS Cancer Facts & Figures (2007)). Thus, there is an urgent need to identify a more reliable marker to differentiate HCC from other liver pathologies and facilitate early detection of this disease. In addition, there is an urgent need to develop new and more-effective therapeutic agents for the treatment of HCC.

SUMMARY OF THE INVENTION

The present invention encompasses, in one embodiment, a method of treating hepatocellular carcinoma (HCC) in a subject (e.g., a human) in need thereof, comprising administering to the subject a therapeutically effective amount of at least one Plasmalemma Vesicle-Associated Protein (PLVAP) antagonist that inhibits the formation, growth and/or progression of one or more HCC tumors in the liver of the subject. In one embodiment, the PLVAP antagonist is an antibody that specifically binds a PLVAP protein (e.g., a human PLVAP protein). In a particular embodiment, the PLVAP antagonist is administered in combination with a second therapeutic agent, such as a chemotherapeutic agent.

In another embodiment, the invention relates to a method of treating hepatocellular carcinoma (HCC) in a subject in need thereof, comprising administering to the subject a therapeutically effective amount of an antibody that specifically binds a PLVAP protein and at least one chemotherapeutic agent. The antibody that specifically binds a PLVAP protein is administered to the subject by intra-arterial infusion (e.g., hepatic arterial infusion, transarterial chemoembolization) and can inhibit tumor formation, tumor growth, tumor vascularization or tumor progression in the liver of the subject. In a particular embodiment, the antibody is delivered to endothelial cells of blood vessels within or surrounding an HCC tumor in the liver of the subject.

In another embodiment, the invention relates to a method of diagnosing a hepatocellular carcinoma (HCC) in a subject (e.g., a human), comprising detecting the level of a PLVAP gene product (e.g., PLVAP RNA, PLVAP protein) in a sample from the subject and determining that the level of the PLVAP gene product in the sample is increased relative to a control. According to the invention, an increased level of the PLVAP gene product in the sample relative to the control is indicative of the presence of HCC in the subject. In a particular embodiment, an antibody that specifically binds PLVAP is used to detect the level of a PLVAP protein in a sample from the subject.

In an additional embodiment, the invention provides a method of diagnosing a hepatocellular carcinoma (HCC) in a subject, comprising detecting expression of a PLVAP gene product in a liver tissue sample from the subject. According to the invention, expression of the PLVAP gene product in the liver tissue sample is indicative of HCC. In a particular embodiment, expression of a PLVAP gene product is detected in vascular endothelial cells in the liver tissue sample.

In yet another embodiment, the invention relates to an in vivo method of detecting HCC in a subject (e.g., a human), comprising administering a radioisotope-labeled antibody that specifically binds PLVAP by intra-arterial injection or intravenous injection, obtaining an image of the liver of the subject and detecting accumulation of the antibody in the liver of the subject. According to the invention, detection of accumulation of the antibody in the liver is indicative of HCC in the subject.

In a further embodiment, the invention provides an isolated polypeptide that specifically binds a mammalian (e.g., human) PLVAP protein. In a particular embodiment, the polypeptide is an antibody. In a further embodiment, the antibody is an antibody that competes with monoclonal antibody KFCC-GY4 or KFCC-GY5 for binding to a human PLVAP protein.

In another embodiment, the invention encompasses a pharmaceutical composition comprising at least one PLVAP antagonist and a pharmaceutically-acceptable carrier. In one embodiment, the PLVAP antagonist is an antibody that specifically binds a PLVAP protein (e.g., a human PLVAP protein). In another embodiment, the pharmaceutical composition further comprises a second therapeutic agent, such as such as a chemotherapeutic agent.

In an additional embodiment, the invention relates to a kit for diagnosing HCC in a subject. In one embodiment, the kit includes at least one nucleic acid probe that specifically hybridizes to a PLVAP RNA transcript (e.g., under conditions of high stringency). In another embodiment, the kit comprises a polypeptide (e.g., an antibody) that specifically binds a PLVAP protein (e.g., a human PLVAP protein).

In yet another embodiment, the invention relates to a method of treating hepatocellular carcinoma (HCC) in a subject in need thereof, comprising administering to the subject a therapeutically effective amount of a humanized antibody that specifically binds PLVAP. In a particular embodiment, the antibody is administered to the subject by intra-arterial infusion (e.g., hepatic arterial infusion, transarterial chemoembolization) and can inhibit tumor formation, tumor growth, tumor vascularization or tumor progression in the liver of the subject.

In a further embodiment, the invention provides a humanized antibody that specifically competes with monoclonal antibody KFCC-GY4 or monoclonal antibody KFCC-GY5 for binding to SEQ ID NO:23.

BRIEF DESCRIPTION OF THE DRAWINGS

FIGS. 4A and 4B show the nucleotide sequence (SEQ ID NO:1) and the deduced amino acid sequence (SEQ ID NO:2) of the His-tagged human PLVAP$_{51-442}$ protein recombinant fusion protein used to generate mouse anti-PLVAP polyclonal antisera.

FIG. 6A is a graph depicting the presence of significant relative quantities of PLVAP mRNA in HCC endothelial cells obtained by laser-capturing microdissection from two HCC tissue samples (Sample A (black) and Sample B (gray)) as determined by two-step real-time quantitative RT-PCR. Dashed lines represent Taqman quantitative RT-PCR signals from beta-actin mRNA in the same samples used for quantitative RT-PCR of PLVAP mRNA. The results indicate presence of readily measurable PLVAP mRNA in the dissected endothelial cells (solid lines).

FIG. 6B is a graph depicting the absence of significant relative quantities of PLVAP mRNA in cells obtained by laser-capturing microdissection from non-tumorous liver tissue adjacent to HCC tissue in two HCC samples (Sample A (black) and Sample B (gray)) as determined by two-step Taqman real-time quantitative RT-PCR. The results indicate no detectible (solid black line) and barely detectible (solid gray line) PLVAP mRNA in the dissected cells.

FIG. 6C is a graph depicting the relative quantities of PLVAP mRNA in HCC tumor cells obtained by laser-capturing microdissection from two HCC tissue samples (Sample A (black) and Sample B (gray)) as determined by two-step Taqman real-time quantitative RT-PCR. The results indicate presence of very small amounts of PLVAP mRNA (solid lines) in the dissected HCC cells due to unavoidable minor contamination from portion of vascular endothelial cells attached to the dissected HCC cells.

FIGS. 8C, 8D; and FIGS. 8E, 8F. PLVAP protein, which appears as a brown stain (arrows) in the HCC images, was detected only in capillary endothelial cells of hepatocellular carcinomas (FIGS. 8A, 8C, 8E). No detectable HCC was present in non-tumorous liver tissue (FIGS. 8B, 8D, 8F).

FIGS. 9A, 9B and FIGS. 9C, 9D show paired tissue samples of HCC and adjacent non-tumorous liver tissue. PLVAP protein, which appears as a brown stain (arrows) in the HCC images, was detected only in capillary endothelial cells of hepatocellular carcinomas (FIGS. 9A, 9C, 9E, 9F). No detectable HCC was present in non-tumorous liver tissue (FIGS. 9B, 9D).

FIGS. 14A-14D are images showing sections of formalin-fixed tissue from three different patients with metastatic liver cancers that were stained immunohistochemically with anti-PLVAP polyclonal antiserum. The tissue sections are from patients with metastatic colorectal adenocarcinoma (FIG. 14A), intrahepatic cholangiocarcinoma (FIGS. 14B and 14C) or metastatic ovarian carcinoma (FIG. 14D). The tissue sections shown in FIGS. 14B and 14C are from the same patient. PLVAP protein was not detected in endothelial cells lining the vascular sinusoids/capillary of metastatic cancer tissues.

FIG. 15A shows the nucleotide gene (top) (SEQ ID NO:3) and deduced amino acid (middle) (SEQ ID NO:4) sequences of the $V_H$ domain of monoclonal antibody KFCC-GY4. The sequences of amino acid residues in CDRs 1 (SEQ ID NO:5), 2 (SEQ ID NO:6) and 3 (SEQ ID NO:7) also are indicated (bottom).

FIG. 15B shows the nucleotide gene (top) (SEQ ID NO:8) and deduced amino acid (middle) (SEQ ID NO:9) sequences of the $V_L$ domain of monoclonal antibody KFCC-GY4. The sequences of amino acid residues in CDRs 1 (SEQ ID NO:10), 2 (SEQ ID NO:11) and 3 (SEQ ID NO:12) also are indicated (bottom).

FIG. 16A shows the nucleotide gene (top) (SEQ ID NO:13) and deduced amino acid (middle) (SEQ ID NO:14) sequences of the $V_H$ domain of monoclonal antibody KFCC-GY5. The sequences of amino acid residues in CDRs 1 (SEQ ID NO:15), 2 (SEQ ID NO:16) and 3 (SEQ ID NO:17) also are indicated (bottom).

FIG. 16B shows the nucleotide gene (top) (SEQ ID NO:18) and deduced amino acid (middle) (SEQ ID NO:19) sequences of the $V_L$ domain of monoclonal antibody KFCC-GY5. The sequences of amino acid residues in CDRs 1 (SEQ ID NO:20), 2 (SEQ ID NO:21) and 3 (SEQ ID NO:22) also are indicated (bottom).

FIGS. 19A and 19C are Coomassie blue-stained SDS acrylamide gels. Lane 1: molecular weight standard; Lane 2: hydrophobic membrane proteins extracted with TX-114 from human umbilical cord vascular endothelial cells that had been stimulated with VEGF (40 ng/ml) for 72 hours before extraction.

FIG. 19B is an immunoblot wherein the extract shown in Lane 2 of FIG. 19A was probed with KFCC-GY4 monoclonal antibodies. Lane 1: molecular weight standard; Lane 2: hydrophobic membrane proteins extracted with TX-114 from human umbilical cord vascular endothelial cells that had been stimulated with VEGF (40 ng/ml) for 72 hours before extraction.

FIG. 19D is an immunoblot wherein the extract shown in Lane 2 of FIG. 19C was probed with KFCC-GY-5 monoclonal antibodies. Lane 1: molecular weight standard; Lane 2: hydrophobic membrane proteins extracted with TX-114 from human umbilical cord vascular endothelial cells that had been stimulated with VEGF (40 ng/ml) for 72 hours before extraction.

FIG. 20A is a fluorescence micrograph depicting immunofluorescence staining of human vascular endothelial cells (HUVEC) with control normal mouse IgG. Nuclei were stained with 4',6-diamidino-2-phenylindole (DAPI). Magnification=600×.

FIG. 20B is a fluorescence micrograph depicting immunofluorescence staining of human vascular endothelial cells (HUVEC) with monoclonal antibody to von Willebrand factor (VWF). VWF is a positive marker for human vascular endothelial cells. Nuclei were stained with 4',6-diamidino-2-phenylindole (DAPI). Magnification=600×.

FIG. 20C is a fluorescence micrograph depicting immunofluorescence staining of human vascular endothelial cells (HUVEC) with KFCC-GY4 monoclonal antibody to PLVAP. KFCC-GY4 monoclonal anti-PLVAP antibodies reacted positively with human vascular endothelial cells. Nuclei were stained with 4',6-diamidino-2-phenylindole (DAPI). Magnification=600×.

FIG. 20D is a fluorescence micrograph depicting immunofluorescence staining of human vascular endothelial cells (HUVEC) with KFCC-GY5 monoclonal antibody to PLVAP. KFCC-GY5 monoclonal anti-PLVAP antibodies reacted positively with human vascular endothelial cells. Nuclei were stained with 4',6-diamidino-2-phenylindole (DAPI). Magnification=600×.

FIGS. 22A and 22B, 22C and 22D, 22E and 22F, and 22G and 22H represent the four sets of paired hepatoma and non-tumorous liver tissues.

FIG. 24 shows the amino acid sequence of human PLVAP protein (Genbank Accession No. NP_112600; SEQ ID NO:23).

FIGS. 25A and 25B show the nucleotide sequence of full-length human PLVAP cDNA (Genbank Accession No. NM_031310; SEQ ID NO:24).

DETAILED DESCRIPTION OF THE INVENTION

Definitions

Figure 1:
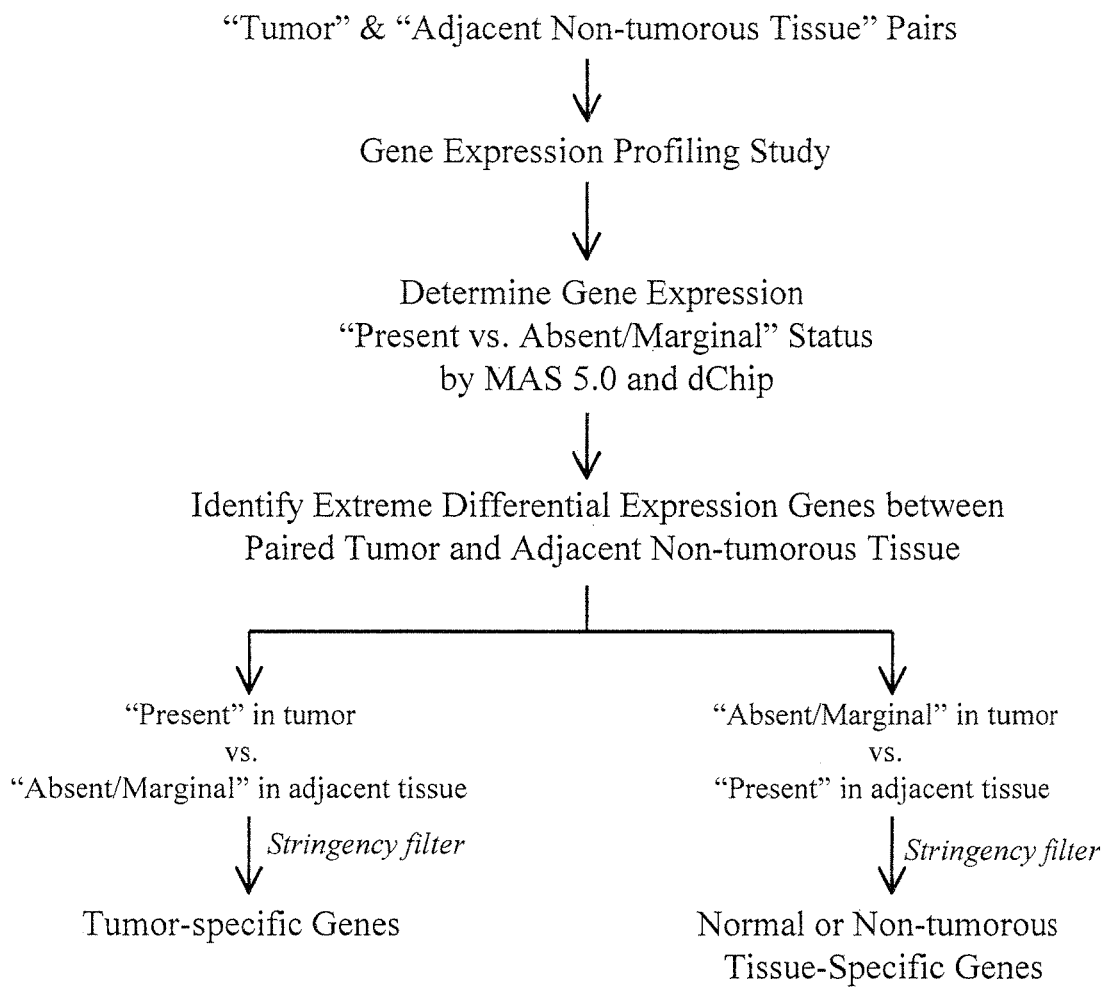
FIG. 1 is a flow chart diagram depicting an algorithm for the identification of genes that show extreme differential expression between tumor and adjacent non-tumorous tissues.

As used herein, the terms "Plasmalemma Vesicle-Associated Protein," "PLVAP," and "PV-1" refer to a naturally occurring or endogenous PLVAP (e.g., mammalian, human) protein, and to proteins having an amino acid sequence that is the same or substantially the same as that of naturally occurring or endogenous PLVAP protein (e.g., recombinant proteins, synthetic proteins). Accordingly, the terms "Plasmalemma Vesicle-Associated Protein," "PLVAP," and "PV-1," which are used interchangeably herein, include polymorphic or allelic variants and other isoforms of a PLVAP protein produced by, e.g., alternative splicing or other cellular processes that occur naturally in mammals (e.g., humans). Preferably, the PLVAP protein is a human protein that has the amino acid sequence of SEQ ID NO:23 (see Genbank Accession No. NP_112600 and FIG. 24).

As defined herein, a "PLVAP antagonist" is an agent (e.g., antibody, small molecule, peptide, peptidomimetic, nucleic acid) that, in one embodiment, inhibits (e.g., reduces, prevents) an activity of a PLVAP protein, or, in another embodiment, inhibits (e.g., reduces, prevents) the expression of a PLVAP gene and/or gene product. Activities of a PLVAP protein that can be inhibited by an antagonist of the invention include, but are not limited to, formation, growth, vascularization and/or progression of a hepatocellular carcinoma tumor. In a particular embodiment, the PLVAP antagonist specifically binds a mammalian (e.g., human) PLVAP protein and inhibits an activity of the PLVAP protein.

As used herein, "specifically binds" refers to binding of an agent (e.g., an antibody) to a PLVAP gene product (e.g., RNA, protein) with an affinity (e.g., a binding affinity) that is at least about 5 fold, preferably at least about 10 fold, greater than the affinity with which the PLVAP antagonist binds a non-PLVAP protein.

As used herein, the term "polypeptide" refers to a polymer of amino acids, and not to a specific length. Thus, "polypeptide" encompasses proteins, peptides, and oligopeptides.

As used herein, the term "antibody" refers to a polypeptide having affinity for a target, antigen, or epitope, and includes both naturally-occurring and engineered antibodies. The term "antibody" encompasses polyclonal, monoclonal, human, chimeric, humanized, primatized, veneered, and single chain antibodies, as well as fragments of antibodies (e.g., Fv, Fc, Fd, Fab, Fab', F(ab'), scFv, scFab, dAb). (See, e.g., Harlow et al., *Antibodies A Laboratory Manual*, Cold Spring Harbor Laboratory, 1988).

The term "antibody variable region" refers to the region of an antibody that specifically binds an epitope (e.g., $V_H$, $V_{HH}$, $V_L$), either independently or when combined with other antibody variable regions (e.g., a $V_H/V_L$ pair).

The term "epitope" refers to a unit of structure conventionally bound by an antibody $V_H/V_L$ pair. An epitope defines the minimum binding site for an antibody and, thus, represents the target of specificity of an antibody.

The term "complementarity determining region," or "CDR," refers to a hypervariable region of an antibody variable region from a heavy chain or light chain that contains amino acid sequences capable of specifically binding to an antigenic target (e.g., epitope). A typical heavy or light chain will have three CDRs (CDR1, CDR2, CDR3), which account for the specificity of the antibody for a particular epitope.

As defined herein, the term "antigen binding fragment" refers to a portion of an antibody that contains one or more CDRs and has affinity for an antigenic determinant by itself. Non-limiting examples include Fab fragments, F(ab)'$_2$ fragments, heavy-light chain dimers, and single chain structures, such as a complete light chain or a complete heavy chain.

As used herein, the term "specificity" refers to the ability of an antibody to bind preferentially to an epitope, and does not necessarily imply high affinity.

The term "affinity" refers to a measure of the binding strength between an antibody and an antigenic determinant. Affinity depends on a number of factors, including the closeness of stereochemical fit between the antibody and antigenic determinant, the size of the area of contact between them, and the distribution of charged and hydrophobic groups.

As used herein, the term "affinity constant," or "$K_d$," refers to a dissociation constant used to measure the affinity of an antibody for an antigen. The lower the affinity constant, the higher the affinity of the immunoglobulin for the antigen or antigenic determinant, and vice versa. Such a constant is readily calculated from the rate constants for the association-dissociation reactions as measured by standard kinetic methodology for antibody reactions.

As referred to herein, the term "competes" means that the binding of a first polypeptide (e.g., antibody) to a target antigen is inhibited by the binding of a second polypeptide (e.g., antibody). For example, binding may be inhibited sterically, for example, by physical blocking of a binding domain or by alteration of the structure or environment of a binding domain such that its affinity or avidity for a target is reduced.

As used herein, the term "peptide" refers to a compound consisting of from about 2 to about 100 amino acid residues wherein the amino group of one amino acid is linked to the carboxyl group of another amino acid by a peptide bond. Such peptides are typically less than about 100 amino acid residues in length and preferably are about 10, about 20, about 30, about 40 or about 50 residues.

As used herein, the term "peptidomimetic" refers to molecules which are not peptides or proteins, but which mimic aspects of their structures. Peptidomimetic antagonists can be prepared by conventional chemical methods (see, e.g., Damewood J. R. "Peptide Mimetic Design with the Aid of Computational Chemistry" in *Reviews in Computational Biology*, 2007, Vol. 9, pp. 1-80, John Wiley and Sons, Inc., New York, 1996; Kazmierski W. K., "*Methods of Molecular Medicine: Peptidomimetic Protocols*," Humana Press, New Jersey, 1999).

The terms "hepatocellular carcinoma," "HCC," and "hepatoma" are used interchangeably herein to refer to cancer that arises from hepatocytes, the major cell type of the liver.

As defined herein, "therapy" is the administration of a particular therapeutic or prophylactic agent to a subject (e.g., a mammal, a human) that results in a desired therapeutic or prophylactic benefit to the subject.

As defined herein, a "therapeutically effective amount" is an amount sufficient to achieve the desired therapeutic or prophylactic effect under the conditions of administration, such as an amount sufficient to inhibit (i.e., reduce, prevent) tumor formation, tumor growth (proliferation, size), tumor vascularization and/or tumor progression (invasion, metastasis) in the liver of a patient with HCC. The effectiveness of a therapy (e.g., the reduction/elimination of a tumor and/or prevention of tumor growth) can be determined by any suitable method (e.g., in situ immunohistochemistry, imaging (ultrasound, CT scan, MRI, NMR), $^3$H-thymidine incorporation).

As defined herein, a "treatment regimen" is a regimen in which one or more therapeutic or prophylactic agents are administered to a mammalian subject at a particular dose (e.g., level, amount, quantity) and on a particular schedule or at particular intervals (e.g., minutes, days, weeks, months).

As used herein, a "subject" refers to a mammalian subject. The term "mammalian subject" is defined herein to include mammals such as primates (e.g., humans), cows, sheep, goats, horses, dogs cats, rabbits, guinea pigs, rats, mice or other bovine, ovine, equine, canine feline, rodent or murine species. Examples of suitable subjects include, but are not limited to, human patients who have, or are at risk for developing, HCC. Examples of high-risk groups for the development of HCC include individuals with chronic hepatitis infection (hepatitis B, hepatitis C) and individuals who have cirrhosis of the liver or related hepatic conditions.

The terms "prevent," "preventing," or "prevention," as used herein, mean reducing the probability/likelihood or risk of HCC tumor formation or progression by a subject, delaying the onset of a condition related to HCC in the subject, lessening the severity of one or more symptoms of an HCC-related condition in the subject, or any combination thereof. In general, the subject of a preventative regimen most likely will be categorized as being "at-risk", i.e., the risk for the subject developing HCC is higher than the risk for an individual represented by the relevant baseline population.

As used herein, the terms "treat," "treating," or "treatment" mean to counteract a medical condition (e.g., a condition related to HCC) to the extent that the medical condition is improved according to a clinically-acceptable standard (e.g., reduced number and/or size of HCC tumors in a subject's liver).

As used herein, the terms "low stringency," "medium stringency," "high stringency," or "very high stringency conditions" describe conditions for nucleic acid hybridization and washing. Guidance for performing hybridization reactions can be found in Current Protocols in Molecular Biology, John Wiley & Sons, N.Y. (1989), 6.3.1-6.3.6, which is incorporated herein by reference in its entirety. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and, preferably, (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc., which are incorporated herein by reference) and chemical methods.

PLVAP

Plasmalemma vesicle-associated protein (PLVAP), also known as PV1, is a type II integral membrane glycoprotein whose expression is restricted to certain vascular endothelial cells (*Mol Biol Cell* 15:3615-3630 (2004)). PLVAP has been shown to be a key structural component of fenestral and stomatal diaphragms of fenestrated endothelia See id. In addition, PLVAP expression is necessary for the formation of endothelial fenestral diaphragms and may be involved in modulating endothelial permeability and transport (Am J Physiol Heart Circ Physiol 286:H1347-1353, 2004). The genomic organization of human PLVAP gene has been reported (Stan R V, Arden K C, Palade G E. cDNA and protein sequence, genomic organization, and analysis of cis regulatory elements of mouse and human PLVAP genes. Genomics 72; 304-313, 2001).

As described herein, the inventors have demonstrated that PLVAP gene expression is significantly elevated in hepatocellular carcinoma tissues relative to adjacent non-tumorous tissues in the liver of human HCC patients. In addition, the present inventors have determined that PLVAP protein is mainly expressed in, and localizes to, vascular endothelial cells surrounding or within HCC tumors, but is not expressed in, or localized to, cells associated with other liver pathologies. Accordingly, PLVAP represents a novel target for the diagnosis and treatment of HCC.

Methods of Therapy

In one aspect, the invention relates to a method of treating hepatocellular carcinoma (HCC) in a subject in need thereof, comprising administering to the subject a therapeutically effective amount of at least one PLVAP antagonist, wherein the PLVAP antagonist inhibits formation, growth, vascularization and/or progression of one or more HCC tumors in the liver of the subject. In a particular aspect, a PLVAP antagonist of the invention inhibits the expression or activity of PLVAP protein in vascular endothelial cells surrounding hepatocytes in the liver of HCC patients.

In one aspect, a therapeutically-effective amount of a PLVAP antagonist is administered to a subject in need thereof to inhibit tumor growth or kill tumor cells. For example, agents which directly inhibit tumor growth (e.g., chemotherapeutic agents) are conventionally administered at a particular dosing schedule and level to achieve the most effective therapy (e.g., to best kill tumor cells). Generally, about the maximum tolerated dose is administered during a relatively short treatment period (e.g., one to several days), which is followed by an off-therapy period. In a particular example, the chemotherapeutic cyclophosphamide is administered at a maximum tolerated dose of 150 mg/kg every other day for three doses, with a second cycle given 21 days after the first cycle. (Browder et al. *Can Res* 60:1878-1886, 2000).

A therapeutically-effective amount of PLVAP antagonist (e.g., inhibitory small molecules, neutralizing antibodies, inhibitory nucleic acids (e.g., siRNA, antisense nucleotides)) can be administered, for example, in a first cycle in which about the maximum tolerated dose of the antagonist is administered in one interval/dose, or in several closely spaced intervals (minutes, hours, days) with another/second cycle administered after a suitable off-therapy period (e.g., one or more weeks). Suitable dosing schedules and amounts for a PLVAP antagonist can be readily determined by a clinician of ordinary skill. Decreased toxicity of a particular PLVAP antagonist as compared to chemotherapeutic agents can allow for the time between administration cycles to be shorter. When used as an adjuvant therapy (to, e.g., surgery, radiation therapy, other primary therapies), a therapeutically-effective amount of a PLVAP antagonist is preferably administered on a dosing schedule that is similar to that of the other cancer therapy (e.g., chemotherapeutics), or on a dosing schedule determined by the skilled clinician to be more/most effective at inhibiting (reducing, preventing) tumor growth. A treatment regimen for a therapeutically-effective amount of an antibody PLVAP antagonist can be, for example, from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg every 1 to 7 days over a period of about 4 to about 6 months. A treatment regimen for an anti-tumor effective amount of a small molecule PLVAP antagonist can be, for example, from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg, every 1 to 7 days over a period of about 4 to about 6 months.

In another aspect, a PLVAP antagonist can be administered in a metronomic dosing regime, whereby a lower dose is administered more frequently relative to maximum tolerated dosing. A number of preclinical studies have demonstrated superior anti-tumor efficacy, potent antiangiogenic effects, and reduced toxicity and side effects (e.g., myelosuppression) of metronomic regimes compared to maximum tolerated dose (MTD) counterparts (Bocci, et al., *Cancer Res*, 62:6938-6943, (2002); Bocci, et al., *Proc. Natl. Acad. Sci.*, 100(22):12917-12922, (2003); and Bertolini, et al., *Cancer Res*, 63(15):4342-4346, (2003)). Metronomic chemotherapy appears to be effective in overcoming some of the shortcomings associated with chemotherapy.

A PLVAP antagonist can be administered in a metronomic dosing regime to inhibit (reduce, prevent) angiogenesis in a patient in need thereof as part of an anti-angiogenic therapy. Such anti-angiogenic therapy may indirectly affect (inhibit, reduce) tumor growth by blocking the formation of new blood vessels that supply tumors with nutrients needed to sustain tumor growth and enable tumors to metastasize. Starving the tumor of nutrients and blood supply in this manner can eventually cause the cells of the tumor to die by necrosis and/or apoptosis. Previous work has indicated that the clinical outcomes (inhibition of endothelial cell-mediated tumor angiogenesis and tumor growth) of cancer therapies that involve the blocking of angiogenic factors (e.g., VEGF, bFGF, TGF-α, IL-8, PDGF) or their signaling have been more efficacious when lower dosage levels are administered more frequently, providing a continuous blood level of the antiangiogenic agent. (See Browder et al. *Can. Res.* 60:1878-1886, 2000; Folkman J., *Sem. Can. Biol.* 13:159-167, 2003). An anti-angiogenic treatment regimen has been used with a targeted inhibitor of angiogenesis (thrombospondin 1 and platelet growth factor-4 (TNP-470)) and the chemotherapeutic agent cyclophosphamide. Every 6 days, TNP-470 was administered at a dose lower than the maximum tolerated dose and cyclophosphamide was administered at a dose of 170 mg/kg. See id. This treatment regimen resulted in complete regression of the tumors. See id. In fact, anti-angiogenic treatments are most effective when administered in concert with other anti-cancer therapeutic agents, for example, those agents that directly inhibit tumor growth (e.g., chemotherapeutic agents). See id.

The therapeutic methods described herein comprise administering a PLVAP antagonist to a subject. The PLVAP antagonist may be administered to the individual in need thereof as a primary therapy (e.g., as the principal therapeutic agent in a therapy or treatment regimen); as an adjunct therapy (e.g., as a therapeutic agent used together with another therapeutic agent in a therapy or treatment regime, wherein the combination of therapeutic agents provides the desired treatment; "adjunct therapy" is also referred to as "adjunctive therapy"); in combination with an adjunct therapy; as an adjuvant therapy (e.g., as a therapeutic agent that is given to the subject in need thereof after the principal therapeutic agent in a therapy or treatment regimen has been given); or in combination with an adjuvant therapy (e.g., chemotherapy (e.g., tamoxifen, cisplatin, mitomycin, 5-fluorouracil, doxorubicin, sorafenib, octreotide, dacarbazine (DTIC), Cis-platinum, cimetidine, cyclophophamide), radiation therapy (e.g., proton beam therapy), hormone therapy (e.g., anti-estrogen therapy, androgen deprivation therapy (ADT), luteinizing hormone-releasing hormone (LH-RH) agonists, aromatase inhibitors (AIs, such as anastrozole, exemestane, letrozole), estrogen receptor modulators (e.g., tamoxifen, raloxifene, toremifene)), or biological therapy). Numerous other therapies can also be administered during a cancer treatment regime to mitigate the effects of the disease and/or side effects of the cancer treatment, including therapies to manage pain (narcotics, acupuncture), gastric discomfort (antacids), dizziness (anti-vertigo medications), nausea (anti-nausea medications), infection (e.g., medications to increase red/white blood cell counts) and the like, all of which are readily appreciated by the person skilled in the art.

Thus, a PLVAP antagonist can be administered as an adjuvant therapy (e.g., with another primary cancer therapy or treatment). As an adjuvant therapy, the PLVAP antagonist can be administered before, after or concurrently with a primary therapy like radiation and/or the surgical removal of a tumor(s). In some embodiments, the method comprises administering a therapeutically effective amount of a PLVAP antagonist and one or more other therapies (e.g., adjuvant therapies, other targeted therapies). An adjuvant therapy (e.g., a chemotherapeutic agent) and/or the one or more other targeted HCC therapies and the PLVAP antagonist can be co-administered simultaneously (e.g., concurrently) either as separate formulations or as a joint formulation. Alternatively, the therapies can be administered sequentially, as separate compositions, within an appropriate time frame (e.g., a cancer treatment session/interval such as 1.5 to 5 hours) as determined by the skilled clinician (e.g., a time sufficient to allow an overlap of the pharmaceutical effects of the therapies). The adjuvant therapy and/or one or more other targeted HCC therapies and the PLVAP antagonist can be administered in a single dose or multiple doses in an order and on a schedule suitable to achieve a desired therapeutic effect (e.g., inhibition of tumor growth, inhibition of angiogenesis, and/or inhibition of cancer metastasis).

One or more agents that are PLVAP antagonists can be administered in single or multiple doses. Suitable dosing and regimens of administration can be determined by a clinician and are dependent on the agent(s) chosen, pharmaceutical formulation and route of administration, various patient factors and other considerations. With respect to the administration of a PLVAP antagonist with one or more other therapies or treatments (adjuvant, targeted, cancer treatment-associated, and the like) the PLVAP antagonist is typically administered as a single dose (e.g., by injection, by infusion, orally), followed by repeated doses at particular intervals (e.g., one or more hours) if desired or indicated.

The amount of the PLVAP antagonist to be administered (e.g., a therapeutically effective amount) can be determined by a clinician using the guidance provided herein and other methods known in the art and is dependent on several factors, including, for example, the particular agent chosen, and the subject's age, sensitivity, tolerance to drugs and overall well-being. For example, suitable dosages for a small molecule can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Suitable dosages for antibodies can be from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg body weight per treatment. Where the PLVAP antagonist is a polypeptide (linear, cyclic, mimetic), the preferred dosage will result in a plasma concentration of the peptide from about 0.1 µg/mL to about 200 µg/mL. Determining the dosage for a particular agent, patient and cancer is well within the abilities of one of skill in the art. Preferably, the dosage does not cause or produces minimal adverse side effects (e.g., immunogenic response, nausea, dizziness, gastric upset, hyperviscosity syndromes, congestive heart failure, stroke, pulmonary edema).

Methods for Administration

According to the methods of the invention, a therapeutically effective amount of a PLVAP antagonist (e.g., antibody, such as an antibody labeled with a radioactive isotope) is administered to a mammalian subject to treat HCC.

A variety of routes of administration can be used, including, for example, oral, dietary, topical, transdermal, rectal, parenteral (e.g., intraarterial, intravenous, intramuscular, subcutaneous injection, intradermal injection), intravenous infusion and inhalation (e.g., intrabronchial, intranasal or oral inhalation, intranasal drops) routes of administration, depending on the agent and the particular cancer to be treated. Administration can be local or systemic as indicated. The preferred mode of administration can vary depending on the particular agent chosen; however, intraarterial administration (e.g., hepatic arterial infusion, trans-arterial chemoembolization (TACE)) is generally preferred to administer therapeutic agents (e.g., antibodies, such as antibodies labeled with a radioactive isotope) of the invention to treat hepatocellular carcinoma.

For example, using hepatic arterial infusion, chemotherapeutic agents (e.g., PLVAP antibodies, such as PLVAP antibodies labeled with a radioactive isotope) can be delivered directly to an HCC tumor through the hepatic artery, for example, during routine TACE treatment of HCC (Camma, et al. *Radiology* 224:47-54, 2002; Befeler, et al. *Clinics in Liver Disease* 9:287-300, 2005; Abou-Alfa *JAMA* 299:1716-1718, 2008). This procedure is done with the help of fluoroscopy (type of x-ray) imaging. Briefly, a catheter is inserted into the femoral artery in the groin and is threaded into the aorta. From the aorta, the catheter is advanced into the hepatic artery or its branches. Once the branches of the hepatic artery that feed the liver cancer are identified, the chemotherapy is infused. An interventional radiologist, who usually carries out this procedure, can determine the amount of chemotherapy that a patient receives at each session. Some patients may undergo repeat sessions at 6 to 12 week intervals. Imaging studies of the liver are repeated in six to 12 weeks to assess the size of the tumor in response to the treatment.

Alternatively, trans-arterial chemoembolization (TACE), a procedure that is similar to intraarterial infusion, can be used to administer PLVAP antagonists (e.g., antibodies) to a subject in need thereof. In TACE, intraarterial infusion of a therapeutic agent is combined with the additional step of blocking (i.e., embolizing) the small blood vessels with particular blocking compounds, such as gelfoam, oil emulsion, or even small metal coils. Thus, TACE has the potential advantages of exposing the tumor to high concentrations of chemotherapy and confining the agents locally in order to prevent or reduce their being carried away by the blood stream. At the same time, TACE deprives the tumor of its needed blood supply, which can result in the damage or death of the tumor cells.

For intraarterial administration of PLVAP antibodies, it is preferred to use antibodies having high affinities to PLVAP (e.g., a $K_d$ less than $10^{-7}$M) so that the infused antibodies will be concentrated in blood vessels of HCC. Chimeric and humanized antibodies are expected to have circulatory half-lives of up to four and up to 14-21 days, respectively. In a particular embodiment, high affinity PLVAP antibodies (e.g., antigen binding fragments, single chain antibodies) with short circulatory half-lives (e.g., about 1 day to about 5 days, for example, about 1, 2, 3, 4 or 5 days) are administered to a patient in order to reduce any toxicity and other adverse side-effects resulting from their administration. In another embodiment, high affinity PLVAP antibodies with long circulatory half-lives (e.g., about 5 days to about 24 days) are administered to a patient to treat HCC.

In many cases it will be preferable to administer a large loading dose followed by periodic (e.g., weekly) maintenance doses over the treatment period. Antibodies can also be delivered by slow-release delivery systems, pumps, and other known delivery systems for continuous infusion into HCC. Dosing regimens may be varied to provide the desired circulating levels of a particular antibody based on its pharmacokinetics. Thus, doses will be calculated so that the desired therapeutic level is maintained.

The actual dose and treatment regimen will be determined by the physician, taking into account the nature of the cancer (primary or metastatic), number and size of tumors, other therapies, and patient characteristics. In view of the life-threatening nature of hepatocellular carcinoma, large doses with significant side effects may be employed.

Nucleic acid-based PLVAP antagonists (e.g., siRNAs, antisense oligonucleotides, natural or synthetic nucleic acids, nucleic acid analogs) can be introduced into a mammalian subject of interest in a number of ways. For instance, nucleic acids may be expressed endogenously from expression vectors or PCR products in host cells or packaged into synthetic or engineered compositions (e.g., liposomes, polymers, nanoparticles) that can then be introduced directly into the bloodstream of a mammalian subject (by, e.g., injection, infusion). Anti-PLVAP nucleic acids or nucleic acid expression vectors (e.g., retroviral, adenoviral, adeno-associated and herpes simplex viral vectors, engineered vectors, non-viral-mediated vectors) can also be introduced into a mammalian subject directly using established gene therapy strategies and protocols (see, e.g., Tochilin V. P. *Annu Rev Biomed Eng* 8:343-375, 2006; Recombinant DNA and Gene Transfer, Office of Biotechnology Activities, National Institutes of Health Guidelines).

Similarly, where the agent is a protein or polypeptide, the agent can be administered via in vivo expression of recombinant protein. In vivo expression can be accomplished by somatic cell expression according to suitable methods (see, e.g., U.S. Pat. No. 5,399,346). Further, a nucleic acid encoding the polypeptide can also be incorporated into retroviral, adenoviral or other suitable vectors (preferably, a replication deficient infectious vector) for delivery, or can be introduced into a transfected or transformed host cell capable of expressing the polypeptide for delivery. In the latter embodiment, the cells can be implanted (alone or in a barrier device), injected or otherwise introduced in an amount effective to express the polypeptide in a therapeutically effective amount.

Diagnostic and Prognostic Methods

The present invention encompasses diagnostic and prognostic methods that comprise assessing expression of PLVAP in a sample (e.g., liver biopsy, fine needle aspiration sample) from a mammalian subject (e.g., a mammalian subject who has a liver tumor). For diagnostic methods of the invention, expression of PLVAP in the sample, or increased expression of PLVAP in the sample relative to a suitable control, indicates that the subject has HCC and/or that the subject is a candidate for an anti-cancer therapy using a PLVAP antagonist.

For prognostic methods of the invention, expression of PLVAP in a sample from a subject, or increased expression PLVAP in the sample relative to a suitable control, indicates a poor prognosis. The prognosis can be a prognosis for patient survival, a prognosis for risk of metastases and/or a prognosis for risk of relapse.

Suitable samples for these methods include a tissue sample, a biological fluid sample, a cell(s) (e.g., a tumor cell) sample, and the like. Any means of sampling from a subject, for example, by blood draw, spinal tap, tissue smear or scrape, or tissue biopsy, can be used to obtain a sample. Thus, the sample can be a biopsy specimen (e.g., tumor, polyp, mass (solid, cell)), aspirate, smear or blood sample. The sample can be a tissue from a liver that has a tumor (e.g., cancerous growth) and/or tumor cells or is suspected of having a tumor and/or tumor cells. For example, a tumor biopsy can be obtained in an open biopsy, a procedure in which an entire (excisional biopsy) or partial (incisional biopsy) mass is removed from a target area. Alternatively, a tumor sample can be obtained through a percutaneous biopsy, a procedure performed with a needle-like instrument through a small incision or puncture (with or without the aid of a imaging device) to obtain individual cells or clusters of cells (e.g., a fine needle aspiration (FNA)) or a core or fragment of tissues (core biopsy). The biopsy samples can be examined cytologically (e.g., smear), histologically (e.g., frozen or paraffin section) or using any other suitable method (e.g., molecular diagnostic methods). A tumor sample can also be obtained by in vitro harvest of cultured human cells derived from an individual's tissue. Tumor samples can, if desired, be stored before analysis by suitable storage means that preserve a sample's protein and/or nucleic acid in an analyzable condition, such as quick freezing, or a controlled freezing regime. If desired, freezing can be performed in the presence of a cryoprotectant, for example, dimethyl sulfoxide (DMSO), glycerol, or propanediol-sucrose. Tumor samples can be pooled, as appropriate, before or after storage for purposes of analysis. The tumor sample can be from a patient who has a liver cancer, for example, hepatocellular carcinoma.

Suitable assays that can be used to assess the presence or amount of a PLVAP in a sample (e.g., biological sample) are known to those of skill in the art. Methods to detect a PLVAP protein or peptide include immunological and immunochemical methods like flow cytometry (e.g., FACS analysis), enzyme-linked immunosorbent assays (ELISA), including chemiluminescence assays, radioimmunoassay, immunoblot (e.g., Western blot), immunohistochemistry (IHC), and other antibody-based quantitative methods (e.g., Luminex® beads-based assays). Other suitable methods include, for example, mass spectroscopy. For example, antibodies to PLVAP can be used to determine the presence and/or expression level of PLVAP in a sample directly or indirectly using, e.g., immunohistochemistry (IHC). For instance, paraffin sections can be taken from a biopsy, fixed to a slide and combined with one or more antibodies by suitable methods. In a particular embodiment, detection of PLVAP protein in vascular endothelial cells surrounding hepatocytes in a sample is indicative of HCC.

Methods to detect PLVAP gene expression include PLVAP nucleic acid amplification and/or visualization. To detect PLVAP gene expression, a nucleic acid can be isolated from an individual by suitable methods which are routine in the art (see, e.g., Sambrook et al., 1989). Isolated nucleic acid can then be amplified (by e.g., polymerase chain reaction (PCR) (e.g., direct PCR, quantitative real time PCR, reverse transcriptase PCR), ligase chain reaction, self sustained sequence replication, transcriptional amplification system, Q-Beta Replicase, or the like) and visualized (by, e.g., labeling of the nucleic acid during amplification, exposure to intercalating compounds/dyes, probes). PLVAP RNA (e.g., mRNA) or expression thereof can also be detected using a nucleic acid probe, for example, a labeled nucleic acid probe (e.g., fluorescence in situ hybridization (FISH)) directly in a paraffin section of a tissue sample taken from, e.g., a tumor biopsy, or using other suitable methods. PLVAP gene expression thereof can also be assessed by Southern blot or in solution (e.g., dyes, probes). Further, a gene chip, microarray, probe (e.g., quantum dots) or other such device (e.g., sensor, nanonsensor/detector) can be used to detect expression and/or differential expression of a PLVAP gene.

In one embodiment, a hepatocellular carcinoma can be diagnosed by detecting expression of a PLVAP gene product (e.g., PLVAP mRNA, PLVAP protein) in a sample from a patient. Thus, the method does not require that PLVAP expression in the sample from the patient be compared to the expression of PLVAP in a control. The presence or absence of PLVAP can be ascertained by the methods described herein or other suitable assays. In another embodiment, an increase in expression of PLVAP can be determined by comparison of PLVAP expression in the sample to that of a suitable control. Suitable controls include, for instance, a non-neoplastic tissue sample from the individual, non-cancerous cells, non-metastatic cancer cells, non-malignant (benign) cells or the like, or a suitable known or determined reference standard. The reference standard can be a typical, normal or normalized range or level of expression of a PLVAP protein or RNA (e.g., an expression standard). Thus, the method does not require that expression of the gene/protein be assessed in a suitable control.

In another embodiment, a hepatocellular carcinoma can be diagnosed by detecting the PLVAP gene copy number in a sample from a patient. For example, in some embodiments, a PLVAP gene copy number that is greater than two (e.g., a gene copy number of 3 or 4) can be diagnostic of HCC. Typically, a normal human cell will have a PLVAP gene copy number of two. Therefore, a method of diagnosis based on PLVAP gene copy number does not require detecting the PLVAP gene copy number in a control sample from the patient, although a control may be used. Suitable controls include, for instance, a non-neoplastic tissue sample from the individual, non-cancerous cells, non-metastatic cancer cells, non-malignant (benign) cells or the like, or a suitable known or determined reference standard (e.g., a PLVAP gene copy number of two). The copy number of the PLVAP gene in a sample from a patient can be ascertained by suitable techniques, such as, for example, fluorescence in situ hybridization (FISH).

PLVAP Antibodies

As described herein, antibodies that bind PLVAP have utility in the diagnosis and treatment of HCC in human subjects. For example, antibodies that specifically bind PLVAP can be used to detect the presence of PLVAP on capillary endothelial cells of hepatocellular carcinoma in specimens of liver core biopsies or needle aspirates by immunohistochemical staining (IHC). In addition, antibodies (e.g., humanized antibodies, chimeric antibodies) to PLVAP can be labeled with a proper tracer (e.g., radioisotope) for immuno-positron emission tomography (immuno-PET) (Clin Cancer Res 12:1958-1960, 2006; Clin Cancer Res 12:2133-2140, 2006) to determine whether a space occupying lesion(s) in the liver of a subject is hepatocellular carcinoma. Anti-PLVAP antibodies (e.g., humanized antibodies) can also be labeled with a cytotoxic agent (radioactive or non-radioactive) for therapeutic purposes (Weiner L M, Adams G P, Von Mehren M. Therapeutic monoclonal antibodies: General principles. In: Cancer: Principles & Practice of Oncology. $6^{th}$ ed. DeVita V T, Hellman S, Rosenberg S A, eds. Philadelphia: Lippincott Williams & Wilkins; 2001:495-508; Levinson W, Jawetz E. Medical Microbiology & Immunology. $4^{th}$ ed. Stamford: Appleton & Lange; 1996:307-47; Scheinberg D A, Sgouros G, Junghans R P. Antibody-based immunotherapies for cancer. In: Cancer Chemotherapy & Biotherapy: Principles and Practice. $3^{rd}$ ed. Chabner B A, Longo D L, eds. Philadelphia: Lippincott Williams & Wilkins; 2001:850-82).

Accordingly, in one embodiment, the invention provides an antibody that binds (e.g., specifically binds) a PLVAP protein (e.g., a human PLVAP protein (SEQ ID NO:23)). Antibodies that specifically bind to a PLVAP protein can be polyclonal, monoclonal, human, chimeric, humanized, primatized, veneered, and single chain antibodies, as well as fragments of antibodies (e.g., Fv, Fc, Fd, Fab, Fab', F(ab'), scFv, scFab, dAb), among others. (See, e.g., Harlow et al., *Antibodies A Laboratory Manual*, Cold Spring Harbor Laboratory, 1988). Antibodies that specifically bind to a PLVAP protein can be produced, constructed, engineered and/or isolated by conventional methods or other suitable techniques. For example, antibodies which are specific for a PLVAP protein can be raised against an appropriate immunogen, such as a recombinant mammalian (e.g., human) PLVAP protein (e.g., SEQ ID NO:23) or a portion thereof (e.g., SEQ ID NO:2) (including synthetic molecules, e.g., synthetic peptides). A variety of such immunization methods have been described (see, e.g., Kohler et al., *Nature,* 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Antibodies can also be raised by immunizing a suitable host (e.g., mouse) with cells that express PLVAP (e.g., cancer cells/cell lines) or cells engineered to express PLVAP (e.g., transfected cells). (See, e.g., Chuntharapai et al., *J. Immunol.,* 152:1783-1789 (1994); Chuntharapai et al. U.S. Pat. No. 5,440,021).

At an appropriate time after immunization, e.g., when the antibody titers are highest, antibody-producing cells can be obtained from the immunized animal and used to prepare monoclonal antibodies by standard techniques, such as the hybridoma technique originally described by Kohler and Milstein (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985) or trioma techniques. The technology for producing hybridomas is well known (see generally Current Protocols in Immunology, Coligan et al., (eds.) John Wiley & Sons, Inc., New York, N.Y., 1994). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide described herein.

Any of the many well known protocols used for fusing lymphocytes and immortalized cell lines can be applied for the purpose of generating a monoclonal antibody to a polypeptide of the invention (see, e.g., Current Protocols in Immunology, supra; Galfre et al., Nature, 266:55052, 1977; R. H. Kenneth, in Monoclonal Antibodies: A New Dimension In Biological Analyses, Plenum Publishing Corp., New York, N.Y., 1980; and Lerner, Yale J. Biol. Med. 54:387-402, 1981). Moreover, the ordinarily skilled worker will appreciate that there are many variations of such methods that also would be useful.

In one alternative to preparing monoclonal antibody-secreting hybridomas, a monoclonal antibody to a PLVAP protein can be identified and isolated by screening a recombinant combinatorial immunoglobulin library (e.g., an antibody phage display library) with the target polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display libraries can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology 9:1370-1372, 1991; Hay et al., Hum. Antibodies Hybridomas 3:81-85, 1992; Huse et al., Science 246:1275-1281, 1989; and Griffiths et al., EMBO J. 12:725-734, 1993.

Antibody fragments (e.g., antigen-binding fragments) can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments.

Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the $CH_1$ domain and hinge region of the heavy chain.

Single chain, human, chimeric, humanized, primatized (CDR-grafted), or veneered antibodies comprising portions derived from different species are also encompassed by the present invention and by the term "antibody." The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also Newman, R. et al., BioTechnology, 10: 1455-1460 (1992) regarding primatized antibody, and Ladner et al., U.S. Pat. No. 4,946,778 and Bird, R. E. et al., Science, 242: 423-426 (1988)) regarding single chain antibodies.

In a particular embodiment, the invention relates to chimeric antibodies that specifically bind to PLVAP (e.g., a human PLVAP protein comprising SEQ ID NO:23). In one embodiment, chimeric antibody of the invention comprises at least one heavy chain and at least one light chain (e.g., kappa light chain) of human IgG4.

In another embodiment, the invention relates to humanized antibodies that specifically bind to PLVAP (e.g., a human PLVAP protein comprising SEQ ID NO:23). Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see, e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions (e.g., dAbs) can be mutated, and sequences encoding variants with the desired specificity can be selected (e.g., from a phage library; see, e.g., Krebber et al., U.S. Pat. No. 5,514,548; Hoogenboom et al., WO 93/06213, published Apr. 1, 1993). Humanized antibodies can also be produced by and/or obtained from commercial sources, including, for example, Antitope Limited (Cambridge, UK).

Other suitable methods of producing or isolating antibodies of the requisite specificity can be used, including, for example, methods which select a recombinant antibody or antibody-binding fragment (e.g., dAbs) from a library (e.g., a phage display library), or which rely upon immunization of transgenic animals (e.g., mice). Transgenic animals capable of producing a repertoire of human antibodies are well-known in the art (e.g., Xenomouse® (Abgenix, Fremont, Calif.)) and can be produced using suitable methods (see, e.g., Jakobovits et al., Proc. Natl. Acad. Sci. USA, 90: 2551-2555 (1993); Jakobovits et al., Nature, 362: 255-258 (1993); Lonberg et al., U.S. Pat. No. 5,545,806; Surani et al., U.S. Pat. No. 5,545,807; Lonberg et al., WO 97/13852).

Once produced, an antibody specific for PLVAP can be readily identified using methods for screening and isolating specific antibodies that are well known in the art. See, for example, Paul (ed.), Fundamental Immunology, Raven Press, 1993; Getzoff et al., Adv. in Immunol. 43:1-98, 1988; Goding (ed.), Monoclonal Antibodies: Principles and Practice, Academic Press Ltd., 1996; Benjamin et al., Ann. Rev. Immunol. 2:67-101, 1984. A variety of assays can be utilized to detect antibodies that specifically bind to PLVAP proteins. Exemplary assays are described in detail in Antibodies: A Laboratory Manual, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assays, inhibition or competition assays, and sandwich assays.

In certain embodiments, the antibodies of the invention have a high binding affinity for PLVAP. Such antibodies will preferably have an affinity (e.g., binding affinity) for PLVAP, expressed as $K_d$, of at least about $10^{-7}$ M (e.g., about $0.4 \times 10^{-7}$ M, about $0.6 \times 10^{-7}$ M, or higher, for example, at least about $10^{-8}$ M, at least about $10^{-9}$ M, or at least about $10^{-10}$ M). The binding affinity of an antibody can be readily determined by one of ordinary skill in the art, for example, by Scatchard analysis (Scatchard, G., Ann. NY Acad. Sci. 51: 660-672, 1949). Binding affinity can also be determined using a commercially available biosensor instrument (BIA-CORE, Pharmacia Biosensor, Piscataway, N.J.), wherein protein is immobilized onto the surface of a receptor chip. See Karlsson, J. Immunol. Methods 145:229-240, 1991 and Cunningham and Wells, J. Mol. Biol. 234:554-563, 1993. This system allows the determination of on- and off-rates, from which binding affinity can be calculated, and assessment of stoichiometry of binding.

The antibodies of the present invention can include a label, such as, for example, a detectable label that permits detection of the antibody, and proteins bound by the antibody (e.g., PLVAP), in a biological sample. A detectable label is particularly suitable for diagnostic applications. For example, a PLVAP antibody can be labeled with a radioactive isotope (radioisotope), which can be detected by one of skill in the art using a gamma counter, a scintillation counter or by autoradiography or other suitable means. Isotopes which are useful for the purpose of the present invention include, but are not limited to: $^3$H, $^{125}$I, $^{131}$I, $^{32}$P, $^{35}$S, $^{14}$C, $^{51}$Cr, $^{36}$Cl, $^{57}$Co, $^{58}$Co, $^{59}$Fe and $^{75}$Se.

Antibodies of the invention can also be labeled with a fluorescent compound (e.g., dyes). When the fluorescently labeled antibody is exposed to light of the proper wave length, its presence can then be detected due to the fluorescence of the compound. Among the most commonly used fluorescent labels are fluorescein isothiocyanate, rhodamine, phycoerytherin, phycocyanin, allophycocyanin, o-phthaldehyde and fluorescamine. The antibodies of the invention can also be labeled using fluorescence emitting metals such as $^{152}$Eu, or others of the lanthanide series. These metals can be attached to the antibody molecule using such metal chelating groups as diethylenetriaminepentaacetic acid (DTPA), tetraaza-cyclododecane-tetraacetic acid (DOTA) or ethylenediaminetetraacetic acid (EDTA).

The antibodies of the present invention also can be coupled to a chemiluminescent compound. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent compounds for purposes of labeling antibodies are luciferin, luciferase and aequorin.

Detection of the labeled antibodies can be accomplished by a scintillation counter, for example, if the detectable label is a radioactive gamma emitter, or by a fluorometer, for example, if the label is a fluorescent material. In the case of an enzyme label, the detection can be accomplished by colorimetric methods that employ a substrate for the enzyme. Detection may also be accomplished by visual comparison of the extent of the enzymatic reaction of a substrate to similarly prepared standards.

Accordingly, the antibodies of the present invention can also be used as a stain for tissue sections. For example, a labeled antibody that binds to PLVAP can be contacted with a tissue sample, e.g., a liver tissue biopsy or fine needle aspirate from a patient. This section may then be washed and the label detected using an appropriate means.

For the purpose of treating HCC, PLVAP antibodies of the invention may include a radiolabel or other therapeutic agent that enhances destruction of cells expressing PLVAP (e.g., vascular endothelial cells surrounding HCC cells). Examples of suitable radioisotope labels for use in HCC therapy include, but are not limited to, $^{125}$I, $^{131}$I, $^{90}$Y, $^{67}$Cu, $^{217}$Bi, $^{211}$At, $^{212}$Pb, $^{47}$Sc, $^{109}$Pd, $^{111}$In and $^{118}$Re. Optionally, a label that emits $\alpha$ and $\beta$ particles upon bombardment with neutron radiation, such as boron, can be used as a label for therapeutic PLVAP antibodies.

Therapeutic antibodies also may include a cytotoxic agent that is capable of selectively killing cells that express PLVAP. For example, bacterial toxins such as diphtheria toxin or ricin can be used. Methods for producing antibodies comprising fragment A of diphtheria toxin are taught in U.S. Pat. No. 4,675,382 (1987). Diphtheria toxin contains two polypeptide chains. The B chain binds the toxin to a receptor on a cell surface. The A chain actually enters the cytoplasm and inhibits protein synthesis by inactivating elongation factor 2, the factor that translocates ribosomes along mRNA concomitant with hydrolysis of ETP. See Darnell, J. et al., in Molecular Cell Biology, Scientific American Books, Inc., page 662 (1986). Alternatively, an antibody comprising ricin, a toxic lectin, may be prepared. Other suitable cytotoxic agents are known by those of skill in the art.

For in vivo detection, PLVAP antibodies of the invention may be conjugated to radionuclides either directly or by using an intermediary functional group. An intermediary group which is often used to bind radioisotopes, which exist as metallic cations, to antibodies is diethylenetriaminepentaacetic acid (DTPA) or tetraaza-cyclododecane-tetraacetic acid (DOTA). Typical examples of metallic cations which are bound in this manner are $^{99}$Tc, $^{123}$I, $^{111}$In, $^{131}$I, $^{97}$Ru, $^{67}$Cu, $^{67}$Ga, and $^{68}$Ga.

Moreover, the antibodies of the invention may be tagged with an NMR imaging agent that includes paramagnetic atoms. The use of an NMR imaging agent allows the in vivo diagnosis of the presence of and the extent of HCC in a patient using NMR techniques. Elements which are particularly useful in this manner are $^{157}$Gd, $^{55}$Mn, $^{162}$Dy, $^{52}$Cr, and $^{56}$Fe.

In one embodiment, the invention relates to a PLVAP antibody produced by hybridoma KFCC-GY4 (ATCC accession number PTA-9963), the hybridoma having been deposited on Apr. 8, 2009, at the American Type Culture Collection (ATCC), P.O. Box 1549, Manassas, Va. 20108, United States of America. In another embodiment, the invention provides a PLVAP antibody produced by hybridoma KFCC-GY5 (ATCC accession number PTA-9964), the hybridoma having been deposited on Apr. 8, 2009, at the American Type Culture Collection (ATCC), P.O. Box 1549, Manassas, Va. 20108, United States of America.

In another embodiment, the invention relates to hybridoma KFCC-GY4 (ATCC accession number PTA-9963). In a further embodiment, the invention provides hybridoma KFCC-GY5 (ATCC accession number PTA-9964).

PLVAP Antagonists

A PLVAP antagonist of the invention can be any agent that inhibits (e.g., reduces, prevents) an activity of a PLVAP gene product. PLVAP activities include, but are not limited to, formation, growth, vascularization or progression of an HCC tumor. In a particular embodiment, a PLVAP antagonist inhibits an activity of a PLVAP gene product (e.g., PLVAP RNA, PLVAP protein) by specifically binding to the PLVAP gene product. PLVAP antagonists also encompass agents that inhibit (reduce, decrease, prevent) the expression (e.g., transcription, mRNA processing, translation) of a PLVAP gene or gene product (e.g., PLVAP RNA, PLVAP protein). A PLVAP antagonist can be an antibody, a small molecule, a peptide, a peptidomimetic, or a nucleic acid, among others.

Antibody Antagonists

A PLVAP antagonist of the invention can be an antibody that specifically binds a PLVAP protein. Such antibodies include, but are not limited to, any of the PLVAP-specific antibodies described herein.

Small Molecule Antagonists

PLVAP antagonists can also be small molecules. Examples of small molecules include organic compounds, organometallic compounds, inorganic compounds, and salts of organic, organometallic or inorganic compounds. Atoms in a small molecule are typically linked together via covalent and/or ionic bonds. The arrangement of atoms in a small organic molecule may represent a chain (e.g., a carbon-carbon chain or a carbon-heteroatom chain), or may represent a ring containing carbon atoms, e.g., benzene or a policyclic system, or a combination of carbon and heteroatoms, i.e., heterocycles such as a pyrimidine or quinazoline. Although small molecules can have any molecular weight, they generally include molecules that are less than about 5,000 daltons. For example, such small molecules can be less than about 1000 daltons and, preferably, are less than about 750 daltons or, more preferably, are less than about 500 daltons. Small molecules and other non-peptidic PLVAP antagonists can be found in nature (e.g., identified, isolated, purified) and/or produced synthetically (e.g., by traditional organic synthesis, bio-mediated synthesis, or a combination thereof). See, e.g., Ganesan, Drug Discov. Today 7(1): 47-55 (January 2002); Lou, Drug Discov. Today, 6(24): 1288-1294 (December 2001). Examples of naturally occurring small molecules include, but are not limited to, hormones, neurotransmitters, nucleotides, amino acids, sugars, lipids, and their derivatives.

Peptide Antagonists

The PLVAP antagonist of the invention can also be a peptide that binds to a PLVAP protein. The peptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups and methods for adding or removing protecting groups are known in the art and are disclosed in, for example, Green and Wuts, "*Protecting Groups in Organic Synthesis*," John Wiley and Sons, 1991. The functional groups of a peptide can also be derivatized (e.g., alkylated) using art-known methods.

The peptide PLVAP antagonist can comprise one or more modifications (e.g., amino acid linkers, acylation, acetylation, amidation, methylation, terminal modifiers (e.g., cyclizing modifications)), if desired. The peptide can also contain chemical modifications (e.g., N-methyl-α-amino group substitution). In addition, the peptide antagonist can be an analog of a known and/or naturally-occurring peptide, for example, a peptide analog having conservative amino acid residue substitution(s). These modifications can improve various properties of the peptide (e.g., solubility, binding), including its PLVAP antagonist activity.

PLVAP antagonists that are peptides can be linear, branched or cyclic, e.g., a peptide having a heteroatom ring structure that includes several amide bonds. In a particular embodiment, the peptide is a cyclic peptide. Such peptides can be produced by one of skill in the art using standard techniques. For example, a peptide can be derived or removed from a native protein by enzymatic or chemical cleavage, or can be synthesized by suitable methods, for example, solid phase peptide synthesis (e.g., Merrifield-type synthesis) (see, e.g., Bodanszky et al. "*Peptide Synthesis*," John Wiley & Sons, Second Edition, 1976). Peptides that are PLVAP antagonists can also be produced, for example, using recombinant DNA methodologies or other suitable methods (see, e.g., Sambrook J. and Russell D. W., *Molecular Cloning: A Laboratory Manual*, $3^{rd}$ Edition, Cold Spring Harbor Laboratory Press, Cold Spring Harbor, N.Y., 2001).

Peptides can be synthesized and assembled into libraries comprising a few to many discrete molecular species. Such libraries can be prepared using methods of combinatorial chemistry, and can be screened using any suitable method to determine if the library comprises peptides with a desired biological activity. Such peptide antagonists can then be isolated using suitable methods known by those of skill in the art.

Peptidomimetic Antagonists

PLVAP antagonists can also be peptidomimetics. For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components: the binding moiety or moieties and the backbone or supporting structure.

The binding moieties are the chemical atoms or groups which will react or form a complex (e.g., through hydrophobic or ionic interactions) with a target molecule, for instance, human PLVAP. For example, the binding moieties in a peptidomimetic can be the same as those in a peptide or protein antagonist. The binding moieties can be an atom or chemical group which reacts with the receptor in the same or similar manner as the binding moiety in the peptide antagonist. For example, computational chemistry can be used to design peptide mimetics of peptides that bind PLVAP proteins. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more-CONH-groups for a-NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic antagonists can be isolated by suitable methods.

Nucleic Acid Antagonists

PLVAP antagonists also include various nucleic acids, including nucleic acid molecules that inhibit PLVAP gene expression (e.g., siRNA, antisense oligonucleotides, ribozymes). For example, small interfering ribonucleic acids (siRNAs) and, similarly, short hairpin ribonucleic acids (shRNAs), which are processed into short siRNA-like molecules in a cell, can prevent the expression (translation) of the PLVAP protein. siRNA molecules can be polynucleotides that are generally about 20 to about 25 nucleotides long and are designed to bind a specific RNA sequence (e.g., a PLVAP mRNA sequence). siRNAs silence gene expression in a sequence-specific manner, binding to a target RNA (e.g., an RNA having the complementary sequence) and causing the RNA to be degraded by endoribonucleases. siRNA molecules able to inhibit the expression of the PLVAP gene product can be produced by suitable methods. There are several algorithms that can be used to design siRNA molecules that bind the sequence of a gene of interest (see, e.g., Mateeva O. et al. *Nucleic Acids Res.* 35(8):Epub, 2007; Huesken D. et al., *Nat. Biotechnol.* 23:995-1001; Jagla B. et al., *RNA* 11:864-872, 2005; Shabalinea S. A. *BMC Bioinformatics* 7:65, 2005; Vert J. P. et al. *BMC Bioinformatics* 7:520, 2006). Expression vectors that can stably express siRNA or shRNA are available. (See, e.g., Brummelkamp, T. R., *Science* 296: 550-553, 2002, Lee, N S, et al., *Nature Biotechnol.* 20:500-505, 2002; Miyagishi, M., and Taira, K. *Nature Biotechnol.* 20:497-500, 2002; Paddison, P. J., et al., *Genes & Dev.* 16:948-958, 2002; Paul, C. P., et al., *Nature Biotechnol.* 20:505-508; 2002; Sui, G., et al., *Proc. Natl. Acad. Sci. USA* 99(6):5515-5520, 2002; Yu, J-Y, et al., *Proc. Natl. Acad. Sci. USA* 99(9):6047-6052, 2002; Elbashir, S M, et al., *Nature* 411:494-498, 2001). Stable expression of siRNA/shRNA molecules is advantageous in the treatment of cancer as it enables long-term expression of the molecules, potentially reducing and/or eliminating the need for repeated treatments.

Antisense oligonucleotides (e.g., DNA, riboprobes) can also be used as PLVAP antagonists to inhibit PLVAP expression. Antisense oligonucleotides are generally short (~13 to ~25 nucleotides) single-stranded nucleic acids that specifically hybridize to a target nucleic acid sequence (e.g., mRNA) and induce the degradation of the target nucleic acid (e.g., degradation of the RNA through RNase H-dependent mechanisms) or sterically hinder the progression of splicing or translational machinery. (See, e.g., Dias N. and Stein C. A., *Mol. Can. Ther.* 1:347-355, 2002). There are a number of different types of antisense oligonucleotides that can be used as PLVAP antagonists, including methylphosphonate oligonucleotides, phosphorothioate oligonucleotides, oligonucleotides having a hydrogen at the 2'-position of ribose replaced by an O-alkyl group (e.g., a methyl), polyamide nucleic acid (PNA), phosphorodiamidate morpholino oligomers (deoxyribose moiety replaced by a morpholine ring), PN (N3'→P5' replacement of the oxygen at the 3' position on ribose by an amine group) and chimeric oligonucleotides (e.g., 2'-O-Methyl/phosphorothioate). Antisense oligonucleotides can be designed to be specific for a protein using predictive algorithms. (See, e.g., Ding, Y., and Lawrence, C. E., *Nucleic Acids Res.*, 29:1034-1046, 2001; Sczakiel, G., *Front. Biosci.*, 5:D194-D201, 2000; Scherr, M., et al., *Nucleic Acids Res.*, 28:2455-2461, 2000; Patzel, V., et al. *Nucleic Acids Res.*, 27:4328-4334, 1999; Chiang, M. Y., et al., *J. Biol. Chem.*, 266:18162-18171, 1991; Stull, R. A., et al., *Nucleic Acids Res.*, 20:3501-3508, 1992; Ding, Y., and Lawrence, C. E., *Comput. Chem.*, 23:387-400, 1999; Lloyd, B. H., et al., *Nucleic Acids Res.*, 29:3664-3673, 2001; Mir, K. U., and Southern, E. M., *Nat. Biotechnol.*, 17:788-792, 1999; Sohail, M., et al., *Nucleic Acids Res.*, 29:2041-2051, 2001; Altman, R. K., et al., *J. Comb. Chem.*, 1:493-508, 1999). The antisense oligonucleotides can be produced by suitable methods; for example, nucleic acid (e.g., DNA, RNA, PNA) synthesis using an automated nucleic acid synthesizer (from, e.g., Applied Biosystems) (see also Martin, P., *Helv. Chim. Acta* 78:486-504, 1995). Antisense oligonucleotides can also be stably expressed in a cell containing an appropriate expression vector.

Antisense oligonucleotides can be taken up by target cells (e.g., tumor cells) via the process of adsorptive endocytosis. Thus, in the treatment of a subject (e.g., mammalian), antisense PLVAP oligonucleotides can be delivered to target cells (e.g., tumor cells) by, for example, injection or infusion. For instance, purified oligonucleotides or siRNA/shRNA can be administered alone or in a formulation with a suitable drug delivery vehicle (e.g., liposomes, cationic polymers, (e.g., poly-L-lysine' PAMAM dendrimers, polyalkylcyanoacrylate nanoparticles and polyethyleneimine)) or coupled to a suitable carrier peptide (e.g., homeotic transcription factor, the Antennapedia peptide, Tat protein of HIV-1, E5 CA peptide).

Ribozymes can also be used as PLVAP antagonists to inhibit PLVAP expression. Ribozymes are RNA molecules possessing enzymatic activity. One class of ribozymes is capable of repeatedly cleaving other separate RNA molecules into two or more pieces in a nucleotide base sequence specific manner. See Kim et al., *Proc Natl Acad Sci USA*, 84:8788 (1987); Haseloff & Gerlach, *Nature*, 334:585 (1988); and Jefferies et al., *Nucleic Acid Res*, 17:1371 (1989). Such ribozymes typically have two functional domains: a catalytic domain and a binding sequence that guides the binding of ribozymes to a target RNA through complementary base-pairing. Once a specifically-designed ribozyme is bound to a target mRNA, it enzymatically cleaves the target mRNA, typically reducing its stability and destroying its ability to directly translate an encoded protein. After a ribozyme has cleaved its RNA target, it is released from that target RNA and thereafter can bind and cleave another target. That is, a single ribozyme molecule can repeatedly bind and cleave new targets.

In accordance with the present invention, a ribozyme may target any portion of the mRNA encoding PLVAP. Methods for selecting a ribozyme target sequence and designing and making ribozymes are generally known in the art. See, e.g., U.S. Pat. Nos. 4,987,071; 5,496,698; 5,525,468; 5,631,359; 5,646,020; 5,672,511; and 6,140,491, each of which is incorporated herein by reference in its entirety. For example, suitable ribozymes may be designed in various configurations such as hammerhead motifs, hairpin motifs, hepatitis delta virus motifs, group I intron motifs, or RNase P RNA motifs. See, e.g., U.S. Pat. Nos. 4,987,071; 5,496,698; 5,525,468; 5,631,359; 5,646,020; 5,672,511; and U.S. Pat. No. 6,140,491; Rossi et al., *AIDS Res Human Retroviruses* 8:183 (1992); Hampel & Tritz, *Biochemistry* 28:4929 (1989); Hampel et al., *Nucleic Acids Res*, 18:299 (1990); Perrotta & Been, *Biochemistry* 31:16 (1992); and Guerrier-Takada et al., *Cell*, 35:849 (1983).

Ribozymes can be synthesized by the same methods used for normal RNA synthesis. For example, suitable methods are disclosed in Usman et al., *J Am Chem Soc*, 109:7845-7854 (1987) and Scaringe et al., *Nucleic Acids Res*, 18:5433-5441 (1990). Modified ribozymes may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature*, 344:565 (1990); Pieken et al., *Science*, 253:314 (1991); and Usman & Cedergren, *Trends Biochem Sci*, 17:334 (1992).

PLVAP antagonists of the invention can also be nucleic acid molecules (e.g., oligonucleotides) that bind to, and inhibit the activity of, a PLVAP protein. Suitable nucleic acid PLVAP antagonists include aptamers, which are capable of binding to a particular molecule of interest (e.g., human PLVAP) with high affinity and specificity through interactions other than classic Watson-Crick base pairing (Tuerk and Gold, Science 249:505 (1990); Ellington and Szostak, Nature 346:818 (1990)).

Aptamers, like peptides generated by phage display or monoclonal antibodies (MAbs), are capable of specifically binding to selected targets and, through binding, block their targets' ability to function. Created by an in vitro selection process from pools of random sequence oligonucleotides, aptamers have been generated for over 100 proteins, including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

An aptamer that binds to a target of interest (e.g., a human PLVAP protein) can be generated and identified using a standard process known as "Systematic Evolution of Ligands by Exponential Enrichment" (SELEX), described in, e.g., U.S. Pat. Nos. 5,475,096 and 5,270,163.

Identification of PLVAP Antagonists

Agents having binding specificity for PLVAP gene products can be identified in a screen, for example, a high-throughput screen of chemical compounds and/or libraries (e.g., chemical, peptide, nucleic acid libraries).

Antibodies that specifically bind human PLVAP can be identified, for example, by screening commercially available combinatorial antibody libraries (Dyax Corp., MorphoSys AG). Suitable combinatorial antibody libraries and standard methods of screening these libraries are described in Hoet et al., *Nature Biotechnology* 23(3):344-348 (2005) and Rauchenberger et al., *J. Biol. Chem.* 278(40):38194-38205 (2003), the contents of which are incorporated herein by reference. Such libraries or collections of molecules can also be prepared using well-known chemical methods.

Alternatively, murine antibodies that specifically bind human PLVAP can be identified, for example, by immunizing mice with PLVAP proteins, protein fragments or peptides along with an adjuvant to break tolerance to the antigen. These antibodies can be screened for the desired specificity and activity and then humanized using known techniques to create suitable agents for the treatment of human disease.

Compounds or small molecules can be identified from numerous available libraries of chemical compounds from, for example, the Chemical Repository of the National Cancer Institute and the Molecular Libraries Small Molecules Repository (PubChem), as well as libraries of the Institute of Chemistry and Cell Biology at Harvard University and other libraries that are available from commercial sources (e.g., Chembridge, Peakdale, CEREP, MayBridge, Bionet). Such libraries or collections of molecules can also be prepared using well-known chemical methods, such as well-known methods of combinatorial chemistry. The libraries can be screened to identify compounds that bind and inhibit PLVAP.

Identified compounds can serve as lead compounds for further diversification using well-known methods of medicinal chemistry. For example, a collection of compounds that are structural variants of the lead can be prepared and screened for PLVAP binding and/or inhibitory activity. This can result in the development of a structure activity relationship that links the structure of the compounds to biological activity. Compounds that have suitable binding and inhibitory activity can be developed further for in vivo use.

Agents that bind PLVAP can be evaluated further for PLVAP antagonist activity. For example, a composition comprising a PLVAP protein can be used in a screen or binding assay to detect and/or identify agents that bind and antagonize the PLVAP protein. Compositions suitable for use include, for example, cells that naturally express a PLVAP protein (e.g., liver vascular endothelial cells), extracts of such cells, and recombinant PLVAP protein.

An agent that binds a PLVAP protein can be identified in a competitive binding assay, for example, in which the ability of a test agent to inhibit the binding of PLVAP to a reference agent is assessed. The reference agent can be a full-length PLVAP protein or a portion thereof. The reference agent can be labeled with a suitable label (e.g., radioisotope, epitope label, affinity label (e.g., biotin and avidin or streptavadin), spin label, enzyme, fluorescent group, chemiluminescent group, dye, metal (e.g., gold, silver), magnetic bead) and the amount of labeled reference agent required to saturate the PLVAP protein in the assay can be determined. The specificity of the formation of the complex between the PLVAP protein and the test agent can be determined using a suitable control (e.g., unlabeled agent, label alone).

The capacity of a test agent to inhibit formation of a complex between the reference agent and a PLVAP protein can be determined as the concentration of test agent required for 50% inhibition ($IC_{50}$ value) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents suitable for use in the method include molecules and compounds which specifically bind to PLVAP, e.g., an antibody that binds PLVAP.

An agent that antagonizes a PLVAP protein can be identified by screening for agents that have an ability to antagonize (reduce, prevent, inhibit) one or more activities of PLVAP, such as, for example, tumor vascularization. Such activities can be assessed by one of skill in the art using any appropriate in vitro or in vivo assay.

Pharmaceutical Compositions

A PLVAP antagonist of the invention can be administered to a mammalian subject as part of a pharmaceutical or physiological composition, for example, as part of a pharmaceutical composition comprising a PLVAP antagonist and a pharmaceutically acceptable carrier. Formulations or compositions comprising a PLVAP antagonist (e.g., an antibody that specifically binds PLVAP) or compositions comprising a PLVAP antagonist and one or more other therapeutic agents (e.g., a chemotherapeutic agent, for example, doxorubicin, 5-fluorouracil, tamoxifen, octreotide) will vary according to the route of administration selected (e.g., solution, emulsion or capsule). Suitable pharmaceutical carriers can contain inert ingredients which do not interact with the PLVAP antagonist. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

Diagnostic Kits

The invention also provides diagnostic kits for detecting the presence of a hepatocellular carcinoma in a subject. Such kits comprise at least one agent (e.g., a nucleic acid probe, an antibody) for detecting PLVAP gene expression in a sample (e.g., a biological sample from a mammalian subject). PLVAP gene expression can be detected, for example, by detecting a PLVAP gene product, such as a PLVAP mRNA or a PLVAP protein, in the sample.

Accordingly, in one embodiment, the kit comprises at least one nucleic acid probe (e.g., an oligonucleotide probe) that specifically hybridizes to a PLVAP RNA (e.g., mRNA, hnRNA) transcript. Such probes are capable of hybridizing to PLVAP RNA under conditions of high stringency.

In another embodiment, the kit includes a pair of oligonucleotide primers that are capable of specifically hybridizing to a PLVAP gene product (e.g., mRNA, cDNA) in a sample. Such primers can be used in any standard nucleic acid amplification procedure (e.g., polymerase chain reaction (PCR), for example, RT-PCR, quantitative real time PCR) to determine the level of the PLVAP gene product in the sample.

In another embodiment, the kits of the invention include an antibody that specifically binds a PLVAP protein (e.g., a human PLVAP protein). Such antibodies include any of the PLVAP antibodies of the invention described herein. In one embodiment, the antibody comprises a $V_H$ domain having the amino acid sequence of SEQ ID NO:4 and a $V_L$ domain having the amino acid sequence of SEQ ID NO:9. In another embodiment, the antibody comprises a $V_H$ domain having the amino acid sequence of SEQ ID NO:14 and a $V_L$ domain having the amino acid sequence of SEQ ID NO:19.

The diagnostic agents in the kits of the invention can include one or more labels (e.g., detectable labels). Numerous suitable labels for diagnostic agents are known in the art and include, but are not limited to, any of the labels described herein. In a particular embodiment, the diagnostic agent (e.g., antibody) includes a radioisotope, such that agent can be used for immuno-positron emission tomography (immuno-PET).

The present invention will now be illustrated by the following Examples, which are not intended to be limiting in any way.

EXEMPLIFICATION

Example 1: PLVAP Expression is Elevated in HCC Liver Tissues Relative to Non-HCC Liver Tissues Materials and Methods:
Tissue Samples Tissues of HCC and adjacent non-tumorous liver were collected from fresh specimens surgically removed from human patients for therapeutic purpose. These specimens were collected under direct supervision of attending pathologists. The collected tissues were immediately stored in liquid nitrogen at the Tumor Bank of the Koo Foundation Sun Yat-Sen Cancer Center (KF-SYSCC). Paired tissue samples from eighteen HCC patients were available for the study. The study was approved by the Institutional Review Board and written informed consent was obtained from all patients. The clinical characteristics of the eighteen HCC patients from this study are summarized in Table 1.

TABLE 1

Clinical data for eighteen HCC patients from which paired HCC and adjacent non-tumorous liver tissue samples were obtained

| Case No | Sex | Age | HBsAg | HBsAb | HCV IgG | TNM Stage | AFP (ng/ml) | Differentiation |
|---|---|---|---|---|---|---|---|---|
| 1 | M | 70 | + |   | − | 2 | 2 | Moderate |
| 2 | M | 75 | − | + | + | 4A | 5 | Well |
| 3 | M | 59 | + |   | − | 4A | 1232 | Moderate |
| 4 | F | 53 | + |   | + | 1 | 261 | Moderate |
| 5 | M | 45 | + |   | − | 2 | 103 | Moderate |
| 6 | M | 57 | + | + | − | 2 | 5 | Moderate |
| 7 | M | 53 | + | + | − | 3A | 19647 | Moderate |
| 8 | M | 54 | − | − | + | 3A | 7 | Moderate |
| 9 | M | 44 | + |   | − | 4A | 306 | Moderate |

TABLE 1-continued

Clinical data for eighteen HCC patients from which paired HCC
and adjacent non-tumorous liver tissue samples were obtained

| Case No | Sex | Age | HBsAg | HBsAb | HCV IgG | TNM Stage | AFP (ng/ml) | Differentiation |
|---|---|---|---|---|---|---|---|---|
| 10 | M | 76 | − | − | + | 3A | 371 | Moderate |
| 11 | F | 62 | + | − | − | 3A | 302 | Moderate |
| 12 | F | 73 | − | − | + | 2 | 42 | Moderate |
| 13 | M | 46 | + | − | − | 4A | 563 | Moderate |
| 14 | M | 45 | − | − | − | 3A | 64435 | Moderate |
| 15 | M | 41 | + | − | − | 2 | 33.9 | Well |
| 16 | M | 44 | + | + | − | 2 | 350 | Moderate |
| 17 | M | 67 | + | − | − | 3A | 51073 | Moderate |
| 18 | M | 34 | + | − | − | 4A | 2331 | Moderate | mRNA Transcript Profiling

Total RNA was isolated from tissues frozen in liquid nitrogen using Trizol® reagents (Invitrogen, Carlsbad, Calif.). The isolated RNA was further purified using RNAEasy® Mini kit (Qiagen, Valencia, Calif.) and its quality assessed using the RNA 6000 Nano assay in an Agilent 2100 Bioanalyzer (Agilent Technologies, Waldbronn, Germany). All RNA samples used for the study had an RNA Integrity Number (RIN) greater than 5.7 (8.2±1.0, mean±SD). Hybridization targets were prepared from 8 total RNA according to Affymetrix® protocols and hybridized to an Affymetrix® U133A GeneChip®, which contains 22,238 probe-sets for approximately 13,000 human genes. Immediately following hybridization, the hybridized array underwent automated washing and staining using an Affymetrix® GeneChip® fluidics station 400 and the EukGE WS2v4 protocol. Thereafter, U133A GeneChip® microarray chips were scanned in an Affymetrix® GeneArray scanner 2500.

Determination of Present and Absent Call of Microarray Data

Affymetrix® Microarray Analysis Suite (MAS) 5.0 software was used to generate present calls for the microarray data for all 18 pairs of HCC and adjacent non-tumor liver tissues. All parameters for present call determination were default values. Each probe-set was determined as "present," "absent" or "marginal" by MAS 5.0. Similarly, the same microarray data were processed using dChip version-2004 software to determine "present," "absent" or "marginal" status for each probe-set on the microarrays.

Identification of Probe-Sets with Extreme Differential Expression

For identification of genes with extreme differential expression between HCC and adjacent non-tumor liver tissue, software written using Practical Extraction and Report Language (PERL) was used according to the following rules: "Tumor-specific genes" were defined as probe-sets that were called "present" in HCC and "absent" or "marginal" in the adjacent non-tumor liver tissue by both MAS 5.0 and dChip. "Non-tumor liver tissue-specific genes" were defined as probe-sets called "absent" or "marginal" in HCC and "present" in the paired adjacent non-tumor liver tissue by both MAS 5.0 and dChip. A flowchart diagram depicting the identification algorithm is shown in FIG. 1.

Real-Time Quantitative Reverse-Transcriptase Polymerase Chain Reaction (RT-PCR)

TaqMan™ real-time quantitative reverse transcriptase-PCR (qRT-PCR) was used to quantify mRNA. cDNA was synthesized from 8 µg of total RNA for each sample using 1500 ng oligo(dT) primer and 600 units SuperScript™ II Reverse Transcriptase from Invitrogen (Carlsbad, Calif.) in a final volume of 60 µl according to the manufacturer's instructions. For each RT-PCR reaction, 0.5 µl cDNA was used as template in a final volume of 25 µl following the manufacturers' instructions (ABI and Roche). The PCR reactions were carried out using an Applied Biosystems 7900HT Real-Time PCR system. Probes and reagents required for the experiments were obtained from Applied Biosystems (ABI) (Foster City, Calif.). The sequences of primers and the probes used for real-time quantitative RT-PCR of PLVAP are 5'-CCTGCAGGCATCCCTGTA-3' (forward primer) (SEQ ID NO:25); 5'-CGGGCCATCCCT-TGGT-3' (reverse primer) (SEQ ID NO:26); and 5'-CCCCATCCAGTGGCTG-3' (probe) (SEQ ID NO:27). Hypoxanthine-guanine phosphoribosyltransferase (HPRT) housekeeping gene was used as an endogenous reference for normalization. All samples were run in duplicate on the same PCR plate for the same target mRNA and the endogenous reference HPRT mRNA. The relative quantities of target mRNAs were calculated by comparative Ct method according to manufacturer's instructions (User Bulletin #2, ABI Prism® 7700 Sequence Detection System). A non-tumorous liver sample was chosen as the relative calibrator for calculation.

Figure 2:
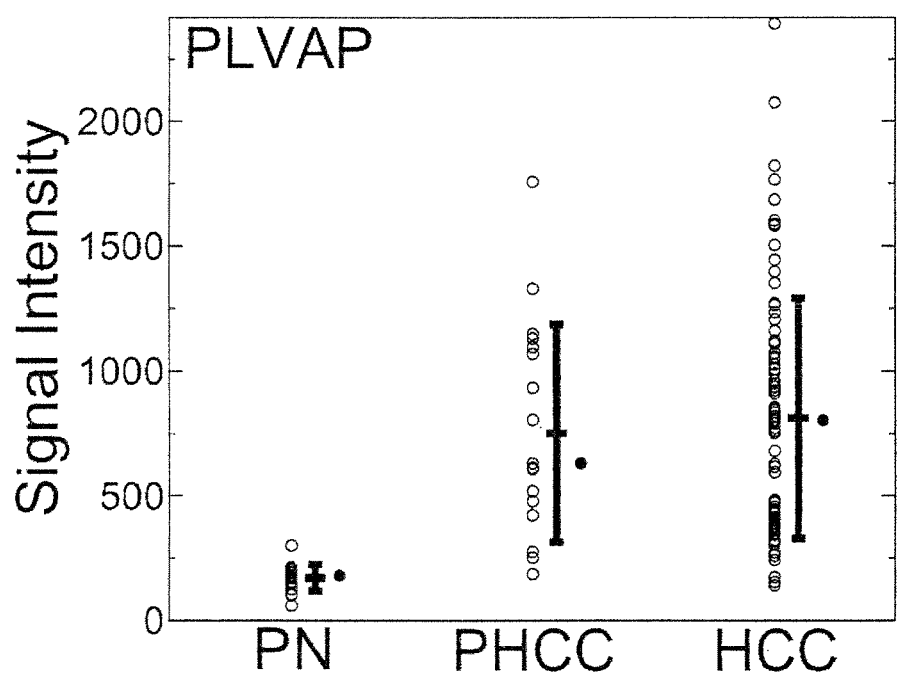
FIG. 2 is a graph depicting PLVAP gene expression intensities in paired HCC (PHCC) and adjacent non-tumorous liver tissue (PN) samples (n=18), as well as unpaired HCC samples (n=82), as determined by mRNA transcript profiling using Affymetrix gene chips.

Results:

The PLVAP gene expression intensities in 18 pairs of HCC and adjacent non-tumorous liver tissues are shown in FIG. 2. The average gene expression intensities were 759.8±436.5 and 170.6±53.4 (mean±SD) for paired HCC and adjacent non-tumorous liver tissue, respectively. The p value of paired t-test between the two groups was $2.8 \times 10^{-5}$. These results indicate that PLVAP is expressed in HCC and not in non-tumorous liver tissue. This elevated expression of PLVAP in HCC was further confirmed when 82 unpaired HCC samples showed an average expression intensity of 810.4±482.0 (mean±SD), which is essentially the same as the finding from the 18 paired HCC samples (p=0.62 by t-test) (FIG. 2).

Figure 3A:
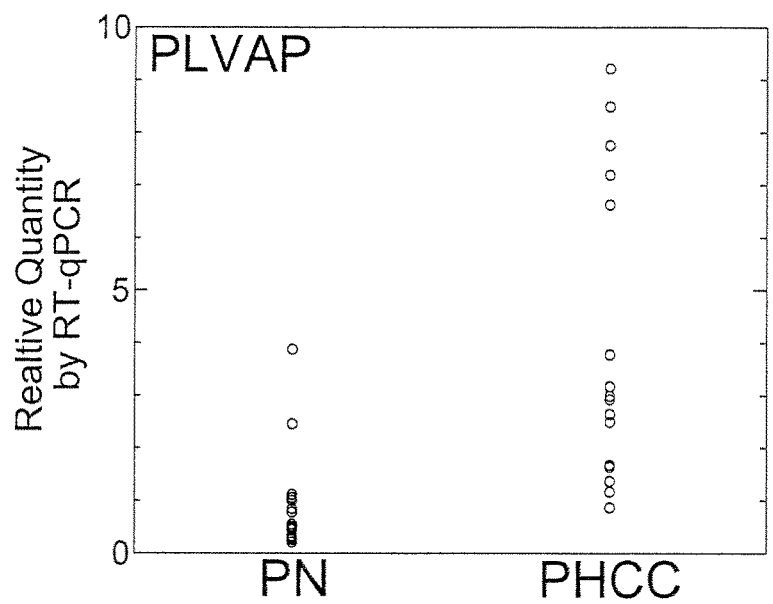
FIG. 3A is a graph depicting relative PLVAP expression quantities in paired HCC (PHCC) and adjacent non-tumorous liver tissue (PN) samples as determined by Taqman quantitative RT-PCR. PLVAP mRNA levels are significantly higher in HCC relative to non-tumorous liver tissues.
Figure 3B:
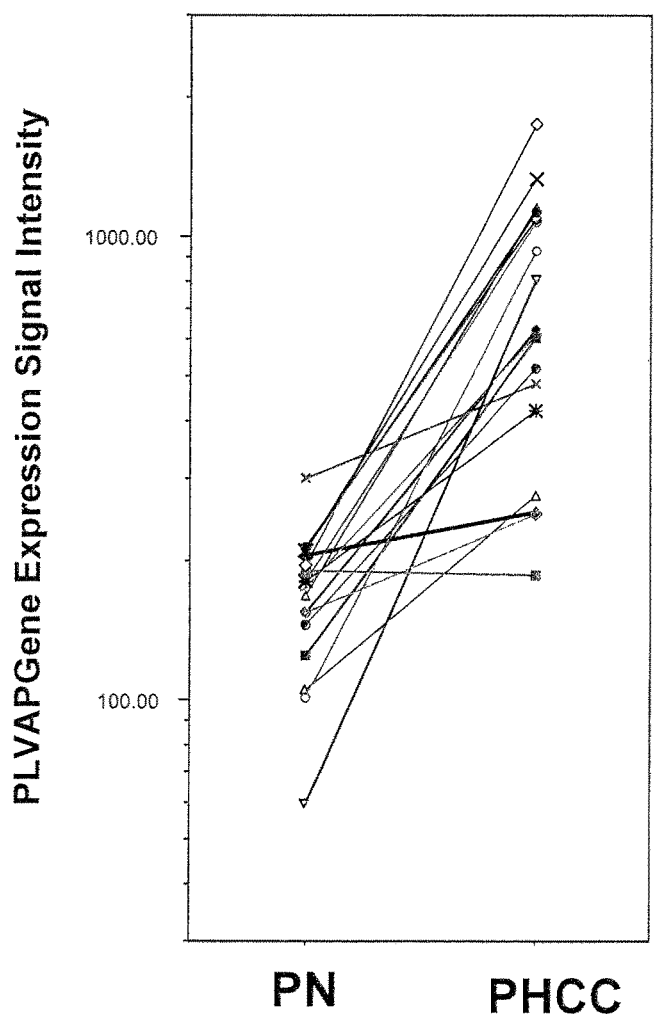
FIG. 3B is a graph depicting PLVAP gene expression intensities in 18 paired HCC (PHCC) and adjacent non-tumorous liver tissue (PN) samples as determined by microarray analysis. PLVAP transcript levels were higher in HCC than in adjacent non-tumorous liver tissue from each individual for all individuals tested except one.

In order to confirm that PLVAP is significantly expressed in HCC liver tissue and not in non-tumorous liver tissue, real-time quantitative RT-PCR was performed on RNA samples from 18 pairs of HCC and adjacent non-tumorous liver tissue. Quantities of PLVAP mRNA were significantly higher in HCC relative to non-tumorous liver tissues (see FIG. 3A and Table 2). Although the results showed some overlap between two groups, PLVAP transcripts were higher in HCC than in adjacent non-tumorous liver tissue within the same individual for all individuals tested except one (FIG. 3B). This exception was likely associated with uneven degrees of RNA degradation during storage process of tissues.

TABLE 2

PLVAP gene expression intensities for 18 pairs of HCC and adjacent non-tumorous liver tissue

| Sample Number | Expression Intensity* HCC | Adjacent non-tumorous liver tissue |
|---|---|---|
| 1 | 1757 | 195 |
| 2 | 1329 | 210 |
| 3 | 1148 | 168 |
| 4 | 1130 | 211 |
| 5 | 1096 | 213 |
| 6 | 1068 | 181 |
| 7 | 932 | 101 |
| 8 | 804 | 60 |
| 9 | 630 | 155 |
| 10 | 612 | 175 |
| 11 | 607 | 125 |
| 12 | 519 | 146 |
| 13 | 478 | 300 |
| 14 | 422 | 180 |
| 15 | 275 | 105 |
| 16 | 251 | 204 |
| 17 | 251 | 155 |
| 18 | 186 | 184 |

Example 2: PLVAP is Specifically Expressed by HCC Vascular Endothelial Cells Materials and Methods:
Laser Capture Microdissection (LCM) of Formalin-Fixed Paraffin Embedded Tissues LCM of formalin fixed tissue from paraffin blocks was carried out using Arcturus PixCell® IIe system, CapSure™ HS LCM caps, and Paradise™ reagent system from Arcturus Bioscience, Inc. (Mountain View, Calif.). Seven micrometer thick tissue sections were cut, deparaffinized, rehydrated, stained and dehydrated for LCM according to manufacturer's instructions. Target cells were captured onto CapSure™ HS LCM caps using 7.5 μm laser spot size at 50 mW power and 1.3 ms duration. Approximately 5000 to 6000 cells were captured on each cap. However, only 1000 to 2000 hepatocellular carcinoma vascular endothelial cells were captured onto each cap due to paucity of cells.

RNA Extraction from LCM Tissue Sections for Quantitative RT-PCR

Cells captured onto the CapSure™ HS LCM caps as described above were processed for RNA extraction, cDNA synthesis, in vitro transcription and antisense RNA amplification using the Paradise™ reagent system according to manufacturer's instructions. The synthesized anti-sense RNA was then used as a template for two-step TaqMan® real time quantitative RT-PCR for quantitation of PLVAP and beta-actin mRNA in the cells captured by LCM. The first step (i.e., reverse transcription) was carried out using 4.5 μl anti-sense RNA and TaqMan® Reverse Transcription Reagents (ABI) in a final volume of 10 μl following the manufacturer's protocol. The second step (i.e., real-time PCR) was performed using 2.4 μl of cDNA template, the primers/probe mix and the TaqMan® universal PCR Master Mix from Applied Biosystems in a final volume of 25 μl. Real-time PCR was carried out in a Smart Cycler® II machine (Cephid, Inc., Sunnyvale, Calif.). The reactions were initially incubated at 50° C. for 2 minutes and then at 95° C. for 10 minutes. Thereafter, 45 cycles of denaturation at 95° C. for 15 seconds and annealing/extension at 60° C. for 40 seconds were performed. The sequences of the primers and the probes are listed in Table 3.

TABLE 3

Primer and probe sequences for real-time quantitative RT-PCR for PLVAP and beta-actin levels in samples prepared by laser-captured microdissection

| | PLVAP gene | beta-Actin gene |
|---|---|---|
| forward primer | 5'-CCTTGAGCGTGAG TGTTTCCA-3' (SEQ ID NO: 28) | 5' GTCCCCCAACTTGAGATGTATGAA G-3' (SEQ ID NO: 29) |
| reverse primer | 5'-GGCAGGGCTGGG AGTTG-3' (SEQ ID NO: 30) | 5'- GTCTCAAGTCAGTGTACAGGTAAG C-3' (SEQ ID NO: 31) |
| Taqman probe | 5'-CTCCCAGGGAG ACCAA-3' (SEQ ID NO: 32) | 5'-AAGGAGTGGCTCCCCTCC-3' (SEQ ID NO: 33) |

Preparation of Expression Vector for Recombinant Fusion PLVAP$_{51\text{-}442}$ Protein Plasmid pGEM®-T Easy-PLVAP$_{51\text{-}442}$ was generated by inserting a PCR fragment encoding amino acid residues 51 to 442 of PLVAP into the pGEM®-T Easy Vector (Promega, Inc., Madison, Wis.). The PCR fragment was amplified from a cDNA clone of PLVAP from OriGene (Rockville, Md.) by using the primer set of 5'-CATATG AACGTGCACGTGAG-CACAGAGTCC-3' (SEQ ID NO:34) and 5'-GGATCC TGAG-CATATCCCTGCATCCTCC-3' (SEQ ID NO:35). For construction of plasmid pET-15b-PLVAP$_{51\text{-}442}$, a cDNA fragment encoding amino acid residues 51 to 442 of PLVAP with NdeI and BamHI recognition sequences at each respective end was excised from pGEM®-T Easy-PLVAP$_{51\text{-}442}$ and inserted into pET-15b (Novagen, Inc., San Diego, Calif.). The expression construct described above was verified by DNA sequencing.

Figure 5:
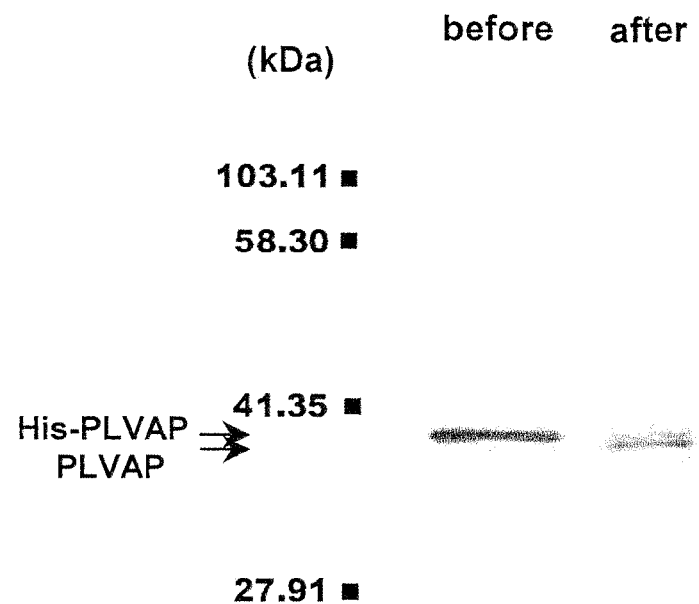
FIG. 5 is an image of a Western blot depicting the detection of recombinant PLVAP protein before and after thrombin digestion to remove the His tag. Arrows to the left of the blot indicate the locations of His-PLVAP and PLVAP on the blot. The numbers to the left of the blot indicate the positions of molecular weight standards.

Expression and Purification of Recombinant Fusion PLVAP$_{51\text{-}442}$ Protein For production of recombinant His-tagged PLVAP$_{51\text{-}442}$ protein (SEQ ID NO:2) (FIG. 4), *Escherichia coli* (Rosetta-Gami™2(DE3)pLysS cells) (Novagen) was transformed by incubating competent cells with pET-15b-PLVAP$_{51\text{-}442}$ plasmid DNA on ice for 5 min, followed by incubation in a 42° C. water bath for 30 s and then again on ice for 2 min. Prior to plating on selective medium, the transformants were incubated at 37° C. while shaking at 250 rpm with SOC medium (0.5% Yeast Extract; 2% Tryptone; 10 mM NaCl; 2.5 mM KCl; 10 mM MgCl$_2$; 10 mM MgSO$_4$; 20 mM Glucose) for 60 min. Expression of His-tagged fusion protein in Rosetta-Gami™2(DE3)pLysS *Escherichia coli* was induced with 1 mM isopropyl-β-D-thiogalactopyranoside for 16 hours at 30° C. Following the induction, the bacterial cells were subjected to lysis by sonication in equilibration buffer (50 mM sodium phosphate, 300 mM NaCl, pH 7) supplemented with 8 M urea and separated into soluble and insoluble fractions by centrifugation at 5,600×g for 30 minutes. For further purification of the His-PLVAP$_{51}$-442 protein, soluble fraction was loaded on a TALON® Metal Affinity Resin (Clontech, Inc., Palo Alto, Calif.), washed with equilibration buffer and eluted with elution buffer (50 mM sodium phosphate, 300 mM NaCl, pH 7, 250 mM imidazole). The His-tag of the purified fusion protein was removed by thrombin cleavage (Novagen) according to manufacturer's instructions (see FIG. 5). The resulting PLVAP$_{51\text{-}442}$ protein was recovered by extensive dialysis against PBS. To verify the identity of the recombinant PLVAP protein, a small quantity of mouse antiserum against GST-PLVAP$_{331-430}$ fusion protein was purchased from the Biodesign Institute (Tempe, Ariz.). The recombinant PLVAP$_{51-442}$ protein without the His-tag was detected by Western blot analysis using this antibody, but did not react with antibodies to the His-tag. These results confirm the identity of the recombinant PLVAP protein.

Generation of Mouse Anti Human PLVAP Serum

Purified PLVAP$_{51-442}$ recombinant protein in PBS was used to immunize 6 weeks old Balb/cByj mice. Each mouse was initially immunized with subcutaneous injection at multiple sites with a total of 14 μg PLVAP$_{51-442}$ protein in complete Freund's adjuvant (Sigma, Inc., St Louis, Mo.). Thereafter, immunization was boosted with 7 μg PLVAP$_{51-442}$ recombinant protein in incomplete Freund's adjuvant once every two weeks for three times. A week after the last boosting immunization, mice were bled for preparation of antiserum.

Enzyme-Linked Immunosorbent Assay (ELISA)

Reagents and Solutions:
1. Recombinant PLVAP protein
2. Anti-mouse IgG-alkaline phosphatase conjugate (Cat. #: AP124A, CHEMICON)
3. Coating buffer (0.137 M Sodium Chloride, 0.01 M Sodium Phosphate Dibasic Heptahydrate, 2 mM Potassium Phosphate Monobasic, 0.002% (0.3 mM) Sodium azide, pH 7.2-7.4)
4. Washing buffer (0.137 M Sodium Chloride, 0.01 M Sodium Phosphate Dibasic Heptahydrate, 2 mM Potassium Phosphate Monobasic, 0.2% Tween20 (Cat. P1379, SIGMA, pH 7.2-7.4)
5. Blocking buffer (0.137 M Sodium Chloride, 0.01 M Sodium Phosphate Dibasic Heptahydrate, 2 mM Potassium Phosphate Monobasic, 2% Bovine Serum Albumin (Cat. 82-045, PENTEX), 0.05% Tween20 (Cat. P1379, SIGMA), pH 7.2-7.4)
6. Carbonate buffer (0.016 M Sodium Bicarbonate, 0.014 M Sodium Carbonate, 2 mM Magnesium Chloride, 0.002% (0.3 mM) Sodium Azide, pH 9.6)
7. Akaline Phosphatase substrate: One 40 mg phosphatase substrate tablet (Cat. P5994, SIGMA) dissolved in 40 ml carbonate buffer Procedure:

The titers of antibodies in the anti-PLVAP sera were determined using ELISA. First, the 96 well ELISA plate was coated with 50 μl of PLVAP protein dissolved in Phosphate buffered saline (PBS) containing 0.002% sodium azide (i.e., coating buffer) at a concentration in the range of 2.5 μg/ml overnight at 4° C. After three washes with 200 μl of washing buffer (PBS containing 0.05% Tween-20), each well of the coated plate was blocked with 150 μl blocking buffer (i.e., washing buffer containing 2% bovine serum albumin) at room temperature for 30 minutes. After three further washes, each well was incubated with 50 μl of diluted antiserum (serial two fold dilution from 1,000× to 128,000×) prepared in the dilution buffer for 45 minutes at room temperature. Thereafter, each well was incubated with anti-mouse IgG alkaline phosphatase conjugate at 5,000× dilution (Chemico, Inc., Temecula, Calif.) for 30 minutes at room temperature. After three washes, the bound antibodies were quantified with 100 μl alkaline phosphatase substrate (Sigma, Inc., St Louis, Mo.) and measurement of absorbance was performed at 405 nm after an incubation period of 25 to 40 min. using an ELISA plate reader.

Immunohistochemical (IHC) Detection of PLVAP in Formalin Fixed Tissues

Six micrometer sections were cut from paraffin blocks of formalin-fixed tissues. The sections were mounted on Super-Frost™ plus adhesion glass slides (Menzel Glaser GmbH, Braunschweig, Germany). The sections then were processed for immunostaining of PLVAP in a Benchmark XT automated staining instrument (Ventana Medical Systems, Inc., Tucson, Ariz.) using XT-iView-DAB-V.1 protocol with mild CCI conditioning for 30 minutes and sections were incubated with 400× diluted anti-human PLVAP serum at 37° C. for 36 minutes. The second antibody and the reagents used to detect binding of mouse anti-human PLVAP antibodies were from the iView™ DAB Detection Kit from Ventana Medical Systems, Inc. (Tucson, Ariz.). All reagents and buffers were purchased from Ventana Medical Systems.

Results:

To determine the cellular source of PLVAP in HCC samples, HCC vascular endothelial cells, tumor cells of hepatocellular carcinoma and non-tumorous hepatocytes, including lining sinusoidal endothelial cells, were dissected out of the samples using laser capture microdissection (LCM). Due to close apposition between hepatoma cells and capillary-lining endothelial cells, effort was made to avoid inclusion of capillary-lining endothelial cells during dissection. The RNAs extracted from the dissected cells were used for two-step real time quantitative RT-PCR to determine the relative quantities of PLVAP mRNA. Specimens from two different patients were studied. The results shown in Table 4 and FIGS. 6A-6C indicate that PLVAP is expressed by HCC vascular endothelial cells (FIG. 6A), while no detectable PLVAP transcript was detected in adjacent non-tumorous liver tissues (FIG. 6B).

TABLE 4

Determination of PLVAP mRNA relative quantities in two HCC samples by Taqman real time quantitative RT-PCR in cells dissected by laser-capturing microdissection

| | Relative Quantity of PLVAP mRNA | | |
| --- | --- | --- | --- |
| HCC Sample | HCC Endothelial Cells | Adjacent Non-tumorous Liver Tissue | HCC Tumor Cells |
| A | 1 | 0 | 0.002 |
| B | 1 | 0.001 | 0.057 |

Figure 7:
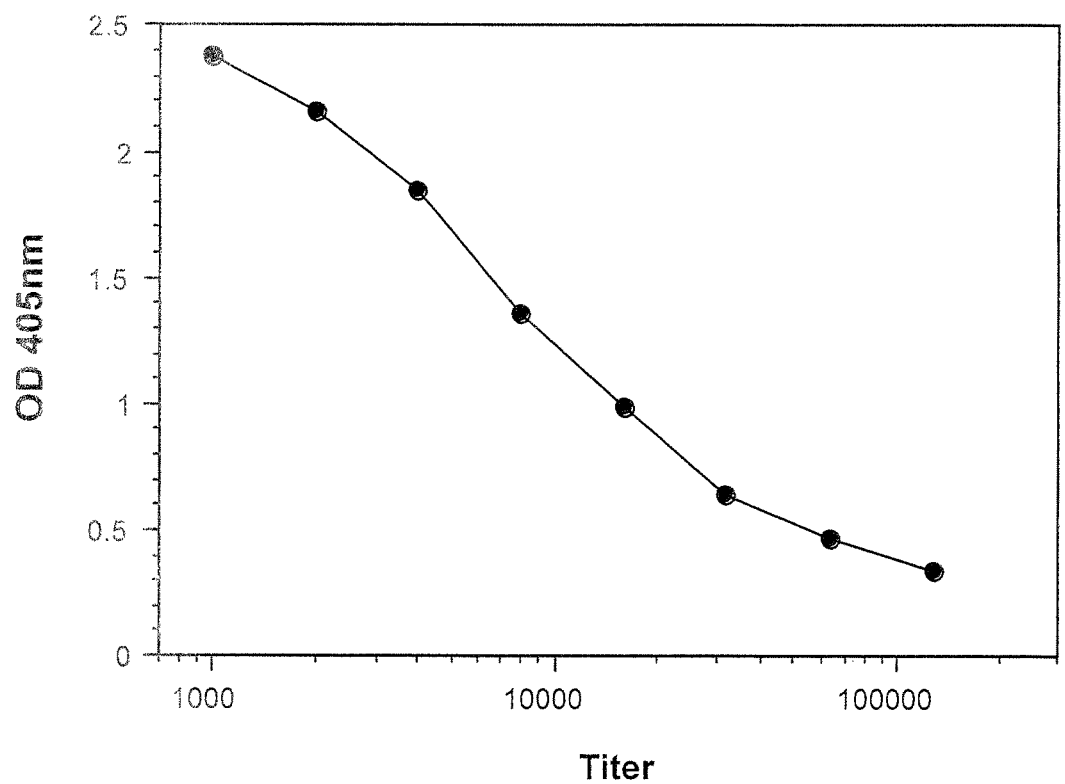
FIG. 7 is a graph depicting anti-PLVAP antibody titer in mouse antiserum raised against recombinant PLVAP$_{51-442}$ protein as determined by ELISA.
Figure 8B:
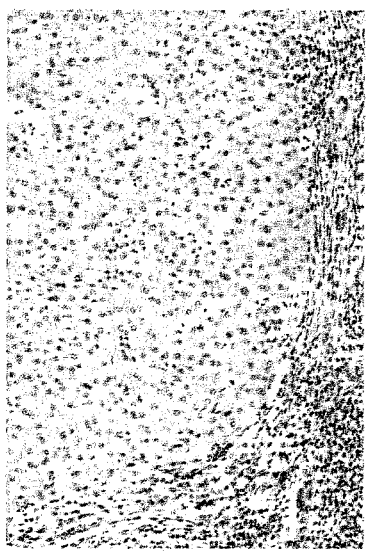
FIGS. 8A-8F are images showing sections of formalin-fixed paired HCC (FIGS. 8A, 8C, 8E) and adjacent non-tumorous liver tissues (FIGS. 8B, 8D, 8F) from three patients with hepatocellular carcinoma that were stained immunohistochemically using anti-PLVAP polyclonal antisera to detect localization of PLVAP protein. Paired tissues are shown in FIGS. 8A, 8B.
Figure 8D:
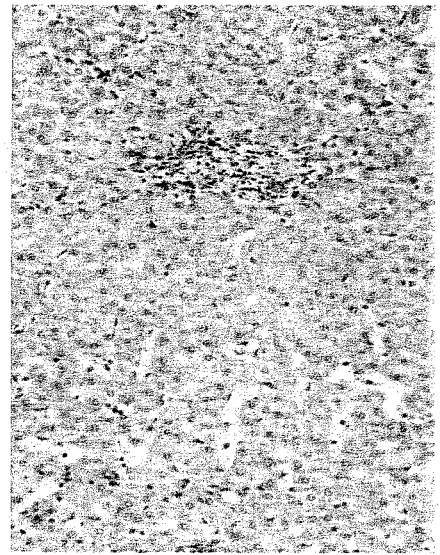
Figure 8F:
Figure 8A:
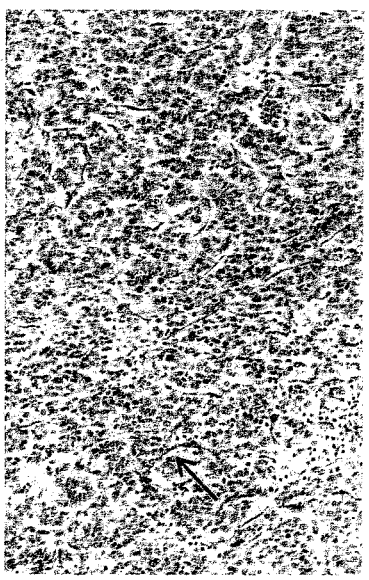
Figure 8C:
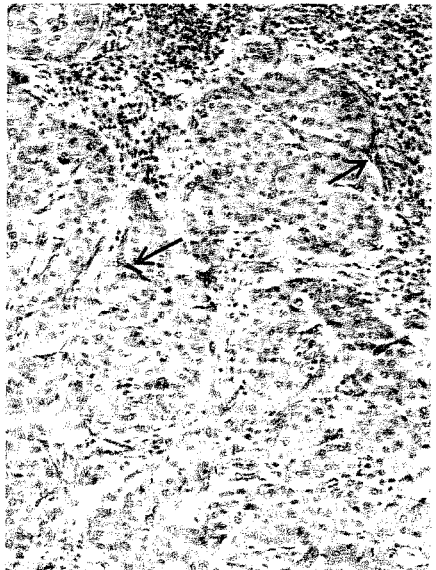
Figure 8E:
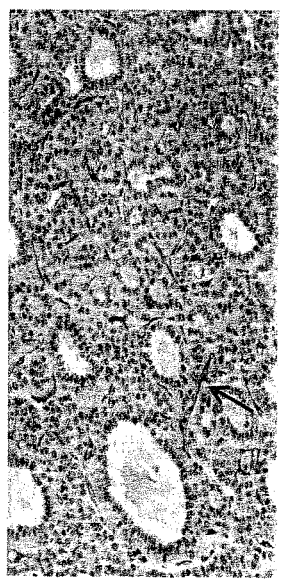
Figure 9A:
FIGS. 9A-9F are images showing sections of formalin-fixed HCC (FIGS. 9A, 9C, 9E, 9F) and non-tumorous liver tissues (FIGS. 9B, 9D) from three additional patients with hepatocellular carcinoma that were stained immunohistochemically using anti-PLVAP polyclonal antisera to detect localization of PLVAP protein.
Figure 9C:
Figure 9E:
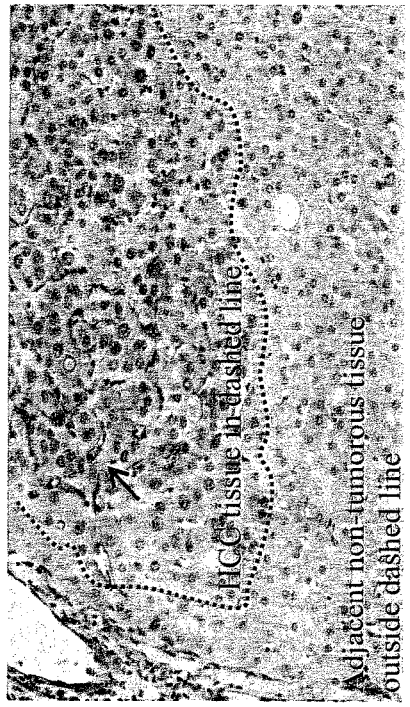
Figure 9B:
Figure 9D:
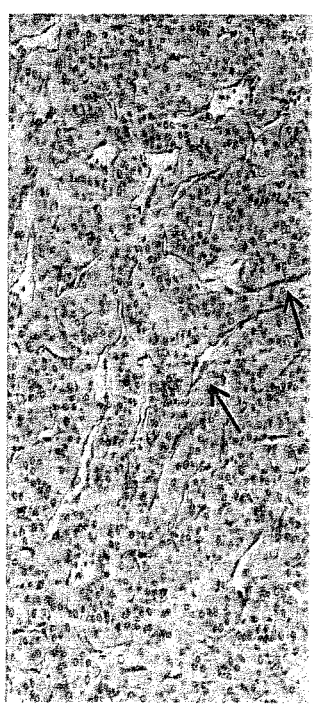
Figure 9F:
Figure 10C:
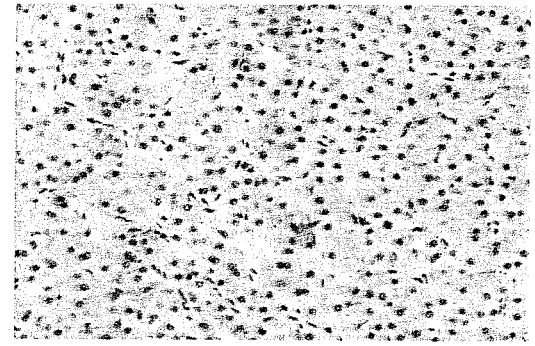
FIGS. 10A-10F are images showing sections of formalin-fixed focal nodular hyperplasia tissues from six different patients that were stained immunohistochemically using anti-PLVAP polyclonal antisera to detect localization of PLVAP protein. PLVAP protein was not detected in endothelial cells lining the vascular sinusoids/capillary of non-tumorous liver tissues of focal nodular hyperplasia. Some positive staining (brown) was noted in epithelial cells of bile ducts (FIGS. 10A, 10D and 10F) and vessels of portal tracts (FIGS. 10D and 10F), but not in the endothelial cells of liver parenchyma. The positive staining of bile duct epithelial cells was due to binding of non-specific antibodies in the PLVAP antiserum.
Figure 10F:
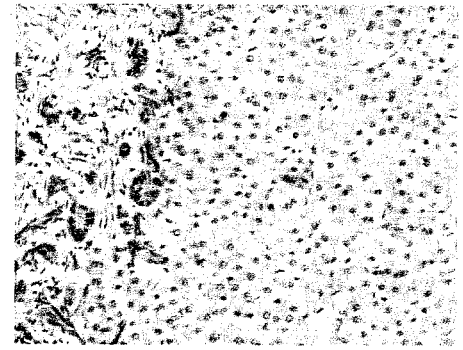
Figure 10B:
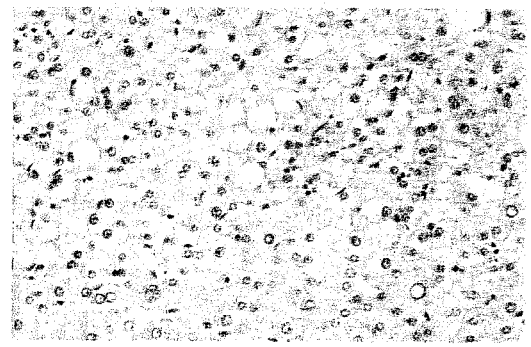
Figure 10E:
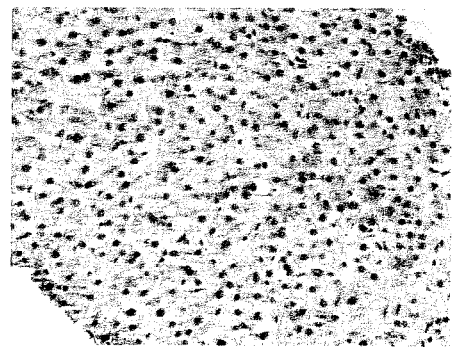
Figure 10A:
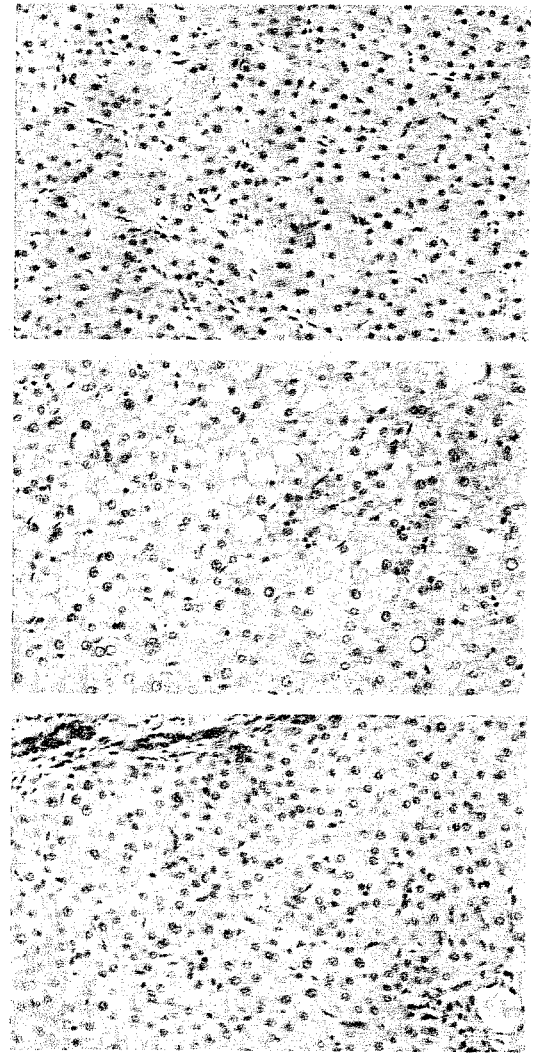
Figure 10D:
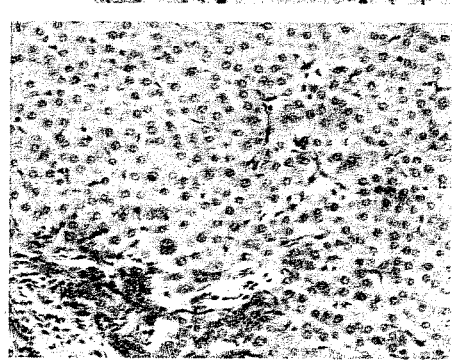

In order to further investigate the tissue and disease specificity of PLVAP expression, polyclonal antibodies for use in immunohistochemistry (IHC) studies were generated against the extracellular domain of human PLVAP (amino acids 51 to 442). As shown in FIG. 7, antiserum obtained from Balb/c mice that were immunized with recombinant PLVAP$_{51-442}$ protein contained a high titer of anti-PLVAP antibodies.

Figure 11B:
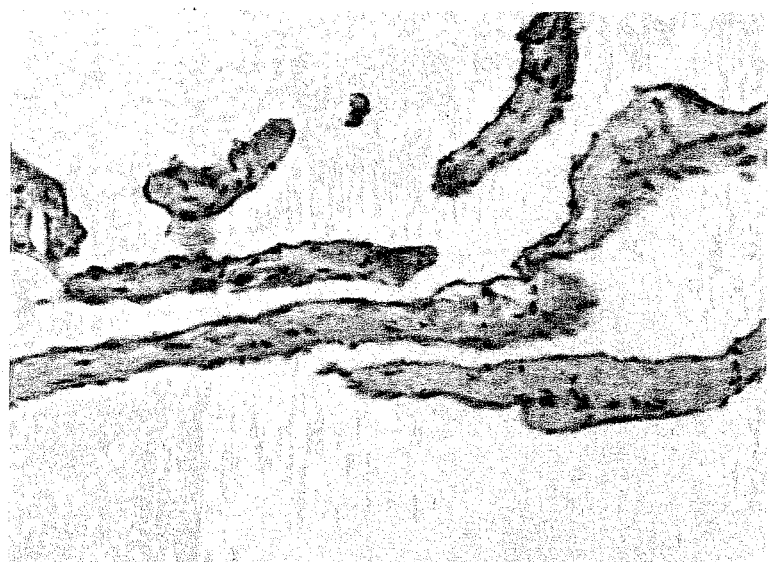
FIGS. 11A and 11B are images showing sections of formalin-fixed tissue from two patients with hepatic hemangioma that were stained immunohistochemically with anti-PLVAP polyclonal antiserum. Endothelial lining cells of hepatic hemangioma did not show significant expression of PLVAP protein.
Figure 11A:
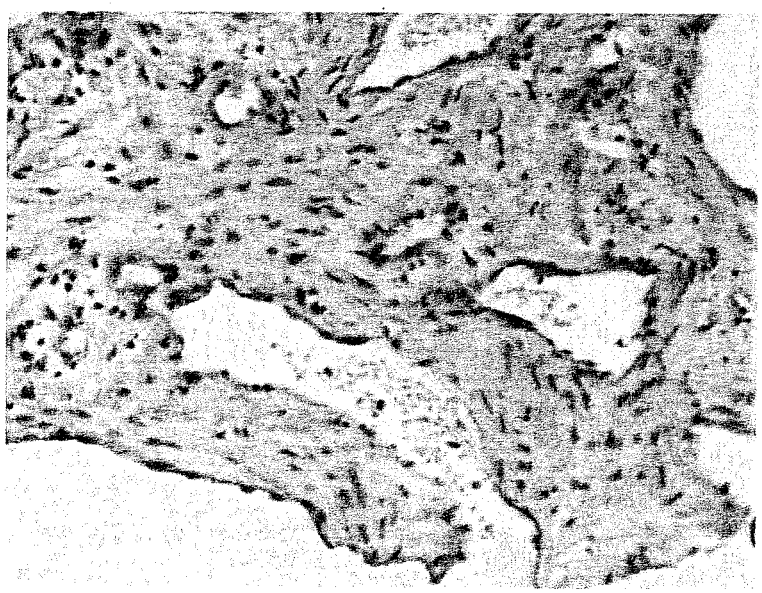
Figure 12A:
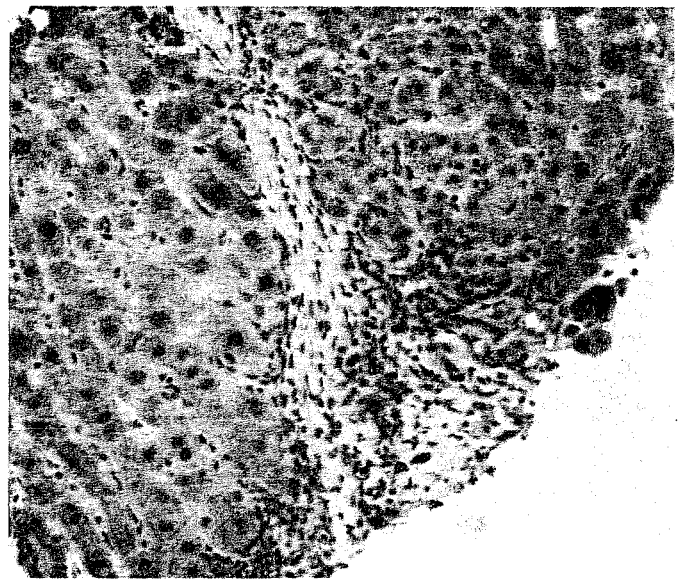
FIGS. 12A and 12B are images showing sections of formalin-fixed tissue from two patients with chronic active hepatitis B that were stained immunohistochemically with anti-PLVAP polyclonal antiserum. PLVAP protein was not detected in endothelial cells lining the vascular sinusoids/capillary of non-tumorous liver tissues from chronic hepatitis B patients.
Figure 12B:
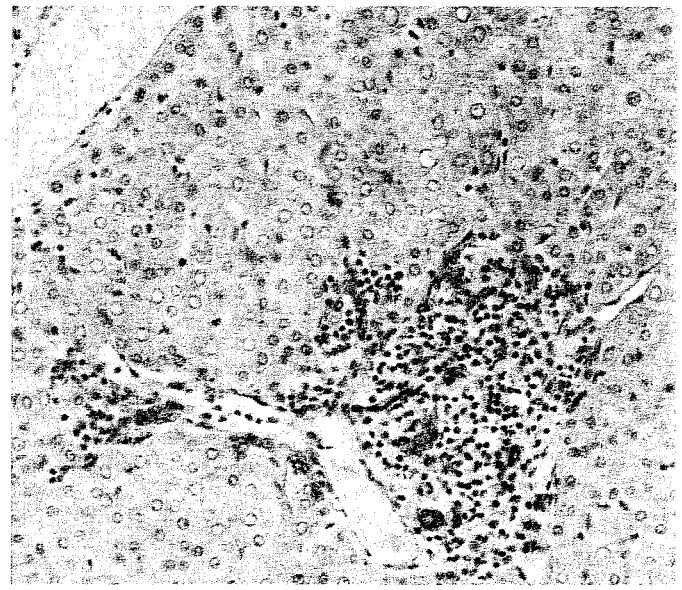
Figure 13A:
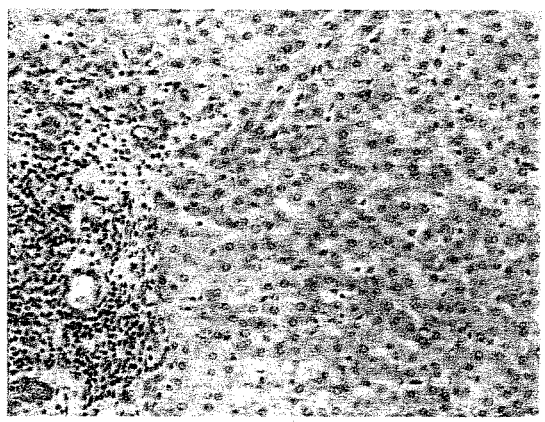
FIGS. 13A-13D are images showing sections of formalin-fixed tissue from three different patients with chronic active hepatitis C that were stained immunohistochemically with anti-PLVAP polyclonal antiserum. The tissue sections shown in FIGS. 13B and 13D are from the same patient. PLVAP protein was not detected in endothelial cells lining the vascular sinusoids/capillary of non-tumorous liver tissues from chronic hepatitis C patients.
Figure 13B:
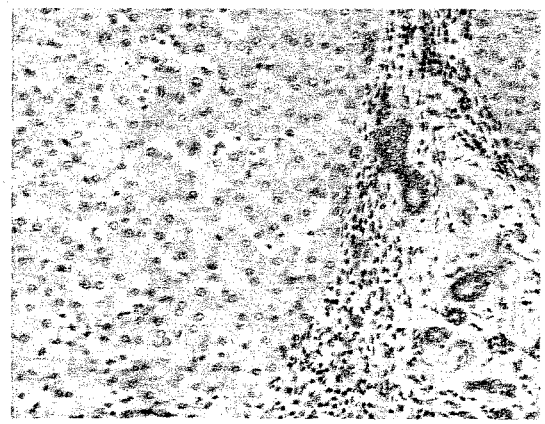
Figure 13C:
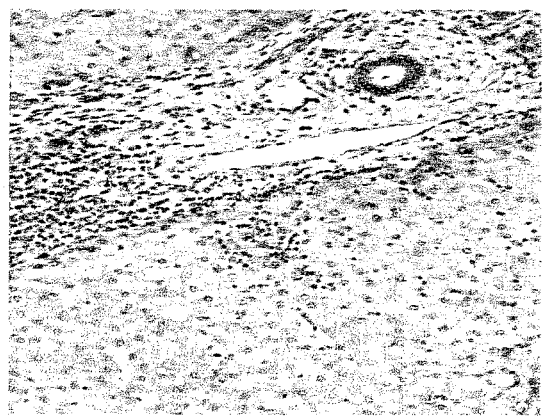
Figure 13D:
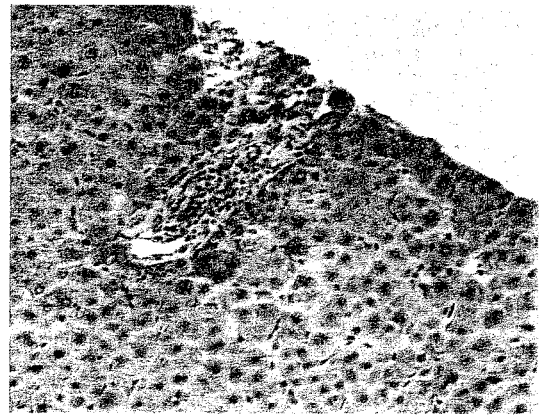

The anti-PLVAP antiserum was then used to determine the localization of PLVAP expression in tissue sections from patients with hepatocellular carcinoma (n=7) (FIGS. 8A-F and 9A-F), focal nodular hyperplasia (n=4) (FIGS. 10A-10F), hepatic hemangioma (n=2) (FIGS. 11A and 11B), chronic active hepatitis B (n=2) (FIGS. 12A and 12B) or C (n=4) (FIGS. 13A-13D), and metastatic cancer (n=4) (i.e., intrahepatic cholangiocarcinoma, metastatic colorectal adenocarcinoma, or metastatic ovarian carcinoma) (FIGS. 14A-14D). The results showed that only capillary endothelial cells of hepatocellular carcinomas expressed PLVAP protein (FIGS. 8A, 8C, 8E, 9A, 9C, 9E and 9F). PLVAP protein was not expressed by endothelial cells lining the vascular sinusoids/capillary of non-tumorous liver tissues, including cirrhotic liver, liver of focal nodular hyperplasia (FIGS. 10A-10F), and chronic hepatitis (FIGS. 12A, 12B, and 13A-13D). Endothelial lining cells of hepatic hemagioma did not show significant expression of PLVAP, either (FIGS. 11A and 11B). These results demonstrate that PLVAP is a vascular endothelial biomarker that is specific for hepatocellular carcinoma, but not for other diseases of liver. Therefore, PLVAP can be used as a diagnostic marker and therapeutic target for HCC.

Example 3: Production and Characterization of Mouse Monoclonal Antibodies that Specifically Bind PLVAP Materials and Methods:
Immunization Procedures Five six-week-old female Balb/cByJ mice were immunized initially with 20 μg of purified recombinant PLVAP protein dissolved in 0.125 mL phosphate buffered saline (PBS) and emulsified in an equal volume of complete Freund's adjuvant. The PLVAP-adjuvant mixture was injected in 0.05 mL volumes into each of four separate subcutaneous sites on the ventral side of the mice near the axillary and inguinal lymphatics, as well as a fifth subcutaneous site, which was located between the scapulae. All mice received a booster immunization of 20 μg of recombinant PLVAP protein injected intraperitoneally three times every two weeks. One week after the last booster immunization, test bleedings were taken to measure whether mice were producing sufficiently high titers of anti-PLVAP antibodies (>10,000×). A solid-phase enzyme-linked immunosorbent assay (ELISA) was used for this purpose. The mouse that produced the highest titer of PLVAP antibody was selected for the production of hybridomas.
Development of Murine Monoclonal Anti PLVAP Antibodies Three days before the scheduled fusion experiment to produce hybridomas, the mouse that produced the highest titer of PLVAP antibody was injected intravenously with 20 μg of recombinant PLVAP. Hybridomas producing monoclonal antibodies (MAbs) against PLVAP were produced according to a previously described protocol (see Unit 2.5 Production of Monoclonal Antibodies, in Current Protocols in Immunology, editors: Coligan J E, Kruisbeek A M, Margulies D H, Shevach E M, and Strober W. Published by John Wiley & Sons, Inc., New York, 2001) with minor modification. Specifically, spleen cells harvested from the immunized mouse were fused with SP2/0 myeloma cells at a ratio of 7.5:1 (spleen cell:myeloma cells) using 50% polyethylene glycol 1540. The fusion products were seeded into 96-well flat-bottom tissue culture plates, and hypoxanthine-aminopterin-thymidine (HAT) selective medium was added the next day. Seven to ten days later, the supernatants of growth-positive wells were screened for production of anti-PLVAP antibodies by ELISA. Hybridomas initially producing anti-PLVAP MAbs were expanded and re-screened. Hybridomas that showed continued production of antibodies were cloned by the limiting dilution method. MAb isotypes were determined using an ELISA. Monoclonal antibodies were purified from ascites or culture media by Protein G affinity column chromatography (Unit 2.7 Purification and Fragmentation of Antibodies, in Current Protocols in Immunology, editors: Coligan J E, Kruisbeek A M, Margulies D H, Shevach E M, and Strober W. Published by John Wiley & Sons, Inc., New York, 2001).

ELISA Assay

ELISA assays were performed as described herein (see Example 2).
Determination of Binding Affinities Binding affinities of KFCC-GY4 and KFCC-GY5 anti-PLVAP monoclonal antibodies were measured at the ANT Technology Co., Ltd. (Taipei, Taiwan) using ANTQ300 quartz crystal microbalance technology (Lin S., et al. *J Immunol Methods* 239:121-124 (2000)).
Isolation and Culture of Human Umbilical Vascular Endothelial Cells (HUVEC)

Isolation and culture of HUVEC were carried out according to the established protocol described in Baudin B, Brunee A, Bosselut N and Vaubourdolle M. *Nature Protocols* 2:481-485 (2007). During the maintenance of endothelial cell culture, 1% gelatin (DIFCO, Corp.) dissolved in phosphate buffered saline was used to replace collagen solution for coating culture plates or coverslips.
Extraction of Hydrophobic Membrane Proteins of HUVEC by Triton X-114 (TX-114) Containing Buffer Five hundred thousand HUVEC were seeded in a 10 cm culture dish for 24 hours. The cells were then stimulated with human VEGF at 40 ng/ml for an additional 72 hours. The cultured cells were washed with 5 ml phosphate buffered saline (PBS) twice. The cells then were detached and lifted from the dish by incubation with 1 ml PBS containing 2 mM EDTA, were placed into a centrifuge tube, and were collected by centrifugation at 300×g for 5 minutes. There were approximately 2 million cells in the pellet produced by centrifugation. The cell pellets were re-suspended in 200 μl ice cold 0.05 M Tris buffer containing 5 mM EDTA and 0.5% (v/v) Triton™ X-114 (TX-114) detergent, pH 7.4. The solubilized cell suspension was incubated on ice with occasional gentle vortexing. Thereafter, the cells suspension was centrifuged at 10,000×g for 10 minutes at 4° C. to remove insoluble cellular debris. The supernatant was transferred to a clean microfuge tube and incubated at 37° C. for 5 minutes. During the incubation, TX-114 became separated from the aqueous phase. The microfuge tube was then centrifuged at 1000×g for 10 minutes at room temperature, such that the TX-114 was centrifuged to the bottom of the tube. The aqueous phase at the top of the tube was removed and the TX-114 pellet containing hydrophobic cellular proteins was dissolved in 2×SDS acrylamide gel sample buffer in a final volume of 50 μl. Fifteen μl of sample was used for SDS acrylamide gel electrophoresis.
SDS Acrylamide Gel Electrophoresis, Preparation of Western Blot and Immunoblotting The procedures are the same as previously described by Kao K J, Scornik J C and McQueen C F. *Human Immunol* 27:285-297 (1990), with slight modification. Detection of antibody binding on Western blots was carried out using alkaline phosphatase chemiluminescent substrate and an LAS-4000 Luminescent Image Analyzer (Fujifilm Corp.).
Immunofluorescent Microscopy
Materials:
  1) Primary antibodies:
    a) Normal mouse IgG (Sigma Corp., catalog #: I-5381) dissolved in phosphate buffered saline (PBS) to 1 mg/mL as a stock solution, diluted with PBS-0.5% BSA to a concentration of 5 μg/mL before use;
    b) Monoclonal mouse anti-human von Willebrand factor (vWF) (DakoCytomation Corp., catalog #: M0616) diluted 50× with PBS containing 0.5% BSA before use;
    c) Purified KFCC-GY4 and KFCC-GY5 anti-PLVAP monoclonal antibodies were diluted to 5 μg/ml with PBS containing 0.5% BSA before use;

2) Secondary antibody: FITC-conjugated Goat F(ab')$_2$ anti-mouse IgG (H&L) (Serotec Corp., catalog #: Star105F);
3) VectaShield® Mounting Medium with DAPI (Vector Labs Corp., catalog #: H-1200);
4) 100% Methanol (Merck Corp., catalog #: 1.06009); and
5) Hank's Balanced Salt Solution (HBSS) (Gibco, Corp., catalog #: 12065-056) diluted to 1× before use.

Procedure:

To prepare human umbilical cord vascular endothelial cells for immunofluorescent study, fifty thousand cells were placed in each well of a 24-well culture plate with a 1.5 cm sterile round coverslip placed at the bottom of each well. Each well contained 0.5 ml M199 culture media that was supplemented with 20% fetal calf serum, 1% L-glutamine, 1% antibiotic/antimycotic solution, 50 µg/ml heparin and 75 µg/ml endothelial cell growth supplement (Sigma Corp. E0760). Each coverslip was pre-coated with 200 µl of 0.4 mg/ml calf skin collagen (Sigma Corp. C9791) in 0.04% acetic acid (v/v) overnight. The coverslips were then washed with sterile 1× phosphate buffered saline (PBS), and subsequently air-dried for use. Cells were cultured overnight and then stimulated with 40 ng/ml vascular endothelial growth factor (VEGF) for an additional 72 hours. The cells on the coverslips were used for the immunofluorescent procedure.

To stain the cells for immunofluorescent microscopy, the cells grown on the coverslip in each well were washed with 0.5 ml 1×HBSS. The cells were then fixed and permeabilized in 0.5 ml ice cold methanol for 5 minutes. The fixed cells were washed 3 times with 0.5 ml 1×PBS for 5 minutes per wash. The fixed cells were then blocked with 0.5 ml 1×PBS containing 0.5% BSA for 1 hour at room temperature. The coverslip containing the fixed cells was removed and placed on top of 0.2 ml diluted primary antibody solution, which contained 5 µg/ml normal IgG, KFCC-GY4 or KFCC-GY5 anti-PLVAP monoclonal antibody, or a 50× dilution of anti-human vWF monoclonal antibody, with the fixed cells facing down and in contact with antibody solution. The antibody solution was placed on a piece of parafilm in a small covered plastic container. The humidity inside was maintained by placing a small piece of filter paper wetted with water.

After incubation at 37° C. for one hour in a humidified container, the coverslip was removed and the cells on the coverslip were washed 3 times with 0.5 ml PBS for 5 minutes each time. The fixed cells were then incubated with 0.2 ml 200×-diluted FITC-conjugated Goat F(ab')$_2$ anti-mouse IgG secondary antibody for 50 minutes at 37° C. as described for incubation with primary antibody solution. Thereafter, the cells were washed 3 times with PBS as described above. The stained cells were mounted on a glass slide using VectaShield® anti-fade solution. Excess mounting media was removed from the edge of the coverslip and the edge was sealed with nail polish. The stained cells were examined using a fluorescent microscope.

Results:

Immunization of Balb/cByJ mice with recombinant human PLVAP protein led to the development of hybridomas producing monoclonal antibodies (mAbs) that recognized human PLVAP protein. Two hybridomas were selected for further study. The antibodies produced by these hybridomas were named KFCC-GY4 and KFCC-GY5. The sequences of the $V_H$ and $V_L$ domains of monoclonal antibodies KFCC-GY4 and KFCC-GY5, and the CDRs of these domains, are shown in FIGS. 15A and 15B and 16A and 16B, respectively.

Figure 17:
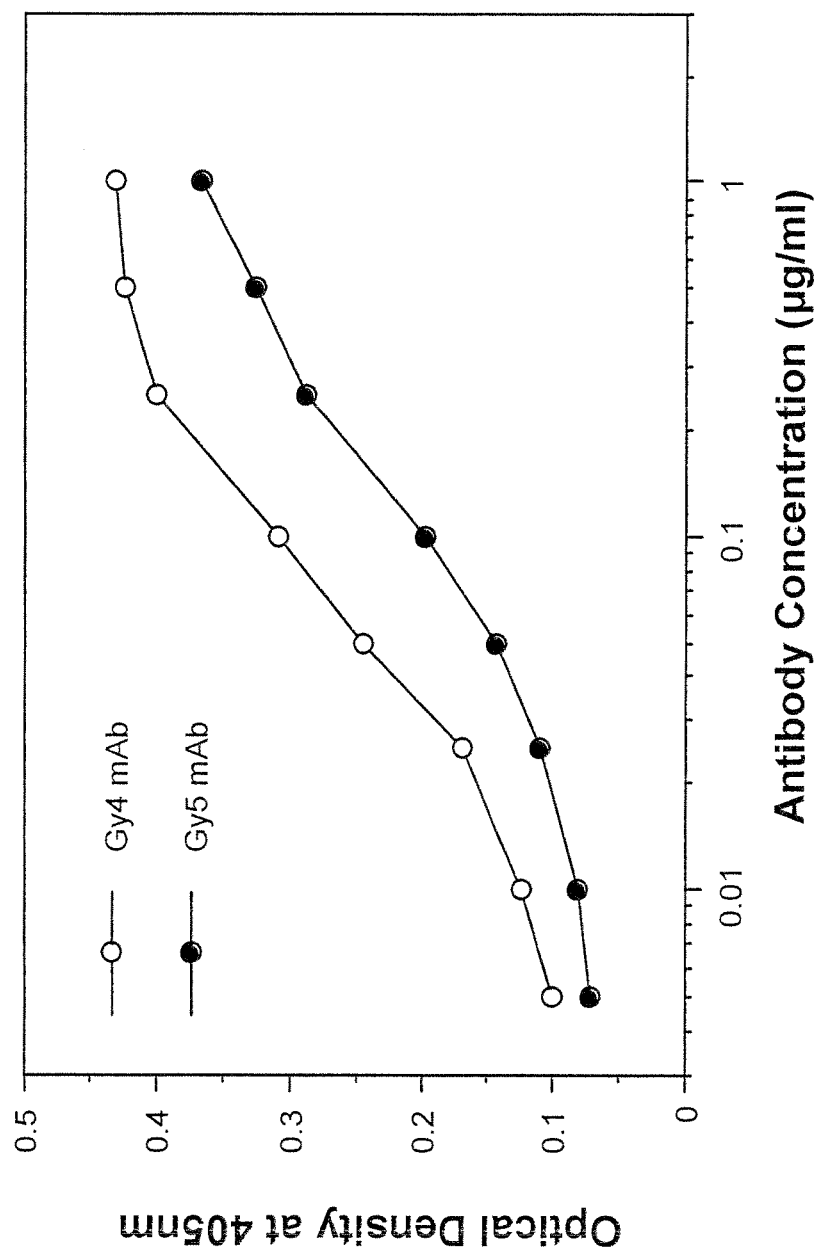
FIG. 17 is a graph depicting the binding of KFCC-GY4 (open circles) and KFCC-GY5 (filled circles) monoclonal antibodies to recombinant PLVAP protein at various antibody concentrations, as determined by ELISA.
Figure 18:
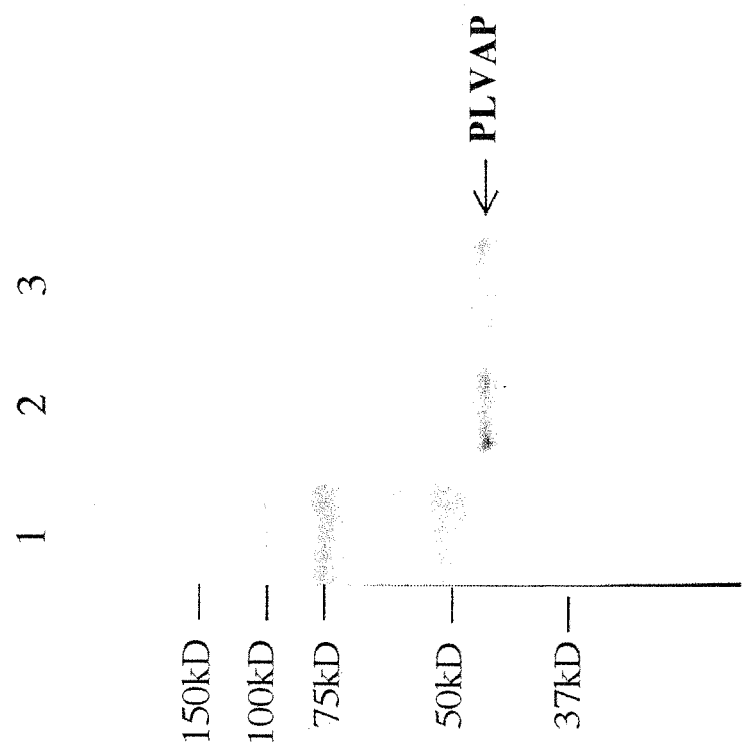
FIG. 18 is an immunoblot showing that KFCC-GY4 and KFCC-GY5 monoclonal antibodies can detect 5 ng of recombinant PLVAP protein. Lane 1: molecular weight standard; Lane 2: immunoblot with KFCC-GY4 monoclonal antibody; Lane 3: immunoblot with KFCC-GY5 monoclonal antibody. The molecular weight of recombinant PLVAP protein is 45 kD.

Both KFCC-GY4 and KFCC-GY5 monoclonal antibodies bound recombinant PLVAP protein in ELISA (FIG. 17) and immunoblot (FIGS. 18C and 18D) assays.

These antibodies also specifically reacted with PLVAP protein in extracts from human umbilical cord vascular endothelial cells in an immunoblot assay (FIGS. 19B and 19D). In addition, immunofluorescence staining experiments showed binding of KFCC-GY4 and KFCC-GY5 monoclonal antibodies to PLVAP-expressing human vascular endothelial cells (FIGS. 20C and 20D).

Binding affinities ($K_d$) of the monoclonal antibodies for recombinant PLVAP protein were determined to be 0.41× $10^{-7}$ M for KFCC-GY5 mAb and 0.6×$10^{-7}$ M for KFCC-GY4 mAb using ANTQ300 quartz crystal microbalance (Lin, et al. *J. Immunol. Methods* 239:121-124, 2000).

Figure 21A:
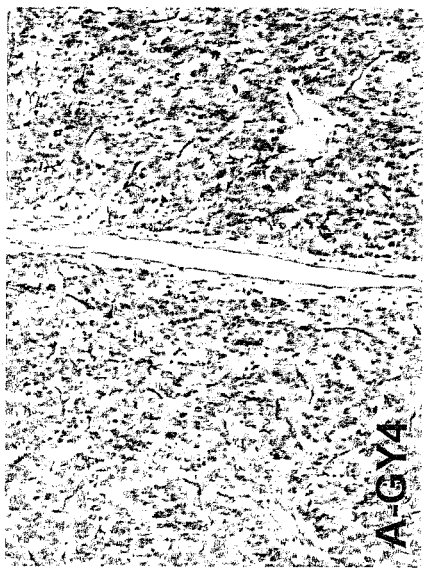
FIG. 21A is a light micrograph of a section of formalin-fixed hepatoma tissue embedded in a paraffin block that was stained with KFCC-GY5 monoclonal anti-PLVAP antibodies. A strong PLVAP signal (dark gray stain) was detected in vascular endothelial cells of hepatoma. Magnification is 100×.
Figure 21B:
FIG. 21B is a light micrograph of a section of formalin-fixed hepatoma tissue from the same patient as the sample shown in FIG. 21A that was stained with KFCC-GY4 monoclonal anti-PLVAP antibodies. A moderate PLVAP signal (light gray stain) was detected in vascular endothelial cells of hepatoma. Magnification is 100×.
Figure 21C:
FIG. 21C is a light micrograph of a section of formalin-fixed hepatoma tissue from a different patient than the samples shown in FIGS. 21A and 21B that was stained with KFCC-GY5 monoclonal anti-PLVAP antibodies. A strong PLVAP signal (dark gray stain) was detected in vascular endothelial cells. Magnification is 100×.
Figure 21D:
FIG. 21D is a light micrograph of a section of formalin-fixed hepatoma tissue from the same patient as the sample shown in FIG. 21C embedded in a paraffin block that was stained with KFCC-GY4 monoclonal anti-PLVAP antibodies. A moderate PLVAP signal (light gray stain) was detected in vascular endothelial cells, indicating that KFCC-GY4 monoclonal antibodies bind the PLVAP antigen less well than KFCC-GY5 antibodies. Magnification is 100×.
Figure 22A:
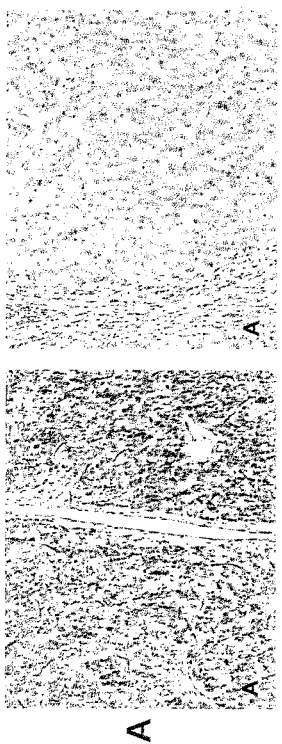
FIGS. 22A-H are light micrographs of sections of hepatoma tissues (FIGS. 22A, 22C, 22E, and 22G) and adjacent non-tumorous liver tissues (FIGS. 22B, 22D, 22F, and 22H) from four different randomly selected hepatoma patients. The sections were stained with KFCC-GY5 monoclonal anti-PLVAP antibodies. PLVAP signal (gray stain) was detected in vascular endothelial cells of hepatoma tissue, but not in vascular endothelial cells non-tumorous liver tissue. Magnification is 100×.
Figure 22B:
Figure 22C:
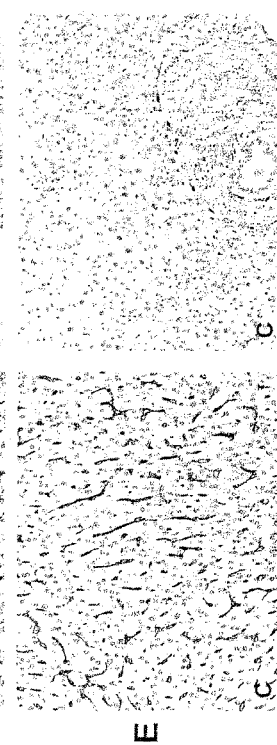
Figure 22D:
Figure 22E:
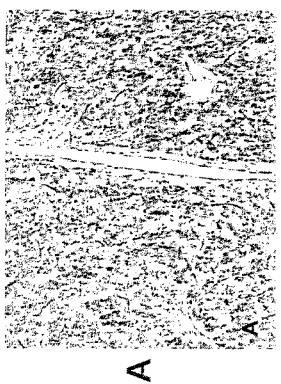
Figure 22F:
Figure 22G:
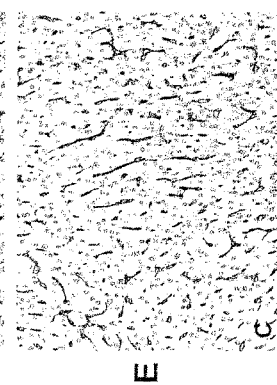
Figure 22H:
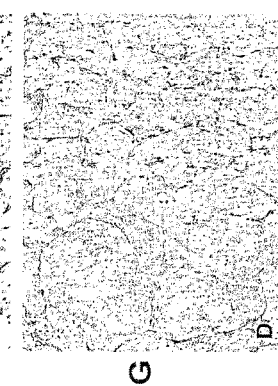

Immunohistochemistry experiments performed on hepatoma sections from the liver of two different hepatoma patients using KFCC-GY4 or KFCC-GY5 monoclonal anti-PLVAP antibodies showed that the KFCC-GY5 monoclonal antibody produced a stronger signal in vascular endothelial cells (FIGS. 21A and 21C) than the KFCC-GY4 monoclonal antibody (FIGS. 21B and 21D).

Immunohistochemistry experiments performed on adjacent hepatoma and non-tumorous liver tissue sections from the liver of the same patient were performed on samples from four different randomly selected hepatoma patients using the KFCC-GY4 monoclonal anti-PLVAP antibody. PLVAP expression was detected in vascular endothelial cells of hepatoma tissues (FIGS. 22A, 22C, 22E and 22G), but not adjacent non-tumorous liver tissues (FIGS. 22B, 22D, 22F and 22H).

Example 4: PLVAP Protein is Expressed on the Surfaces of Vascular Endothelial Cells Materials and Methods:
Immunofluorescent Microscopy
Reagents:

The reagents used for the following procedure are as described in Example 3, with the following modifications:
The 1×HBSS wash buffer contained 0.1% sodium azide, which was used to prevent endocytosis of antibodies bound to the cell surface.
The KFCC-GY4 and KFCC-GY5 monoclonal anti-PLVAP antibodies were diluted in the 1×HBSS wash buffer with 0.1% sodium azide.

Procedure:

Immunofluorescent staining of human umbilical cord vascular endothelial cells (HUVECs) was performed as described in Example 3, except that the cells were not fixed and permeabilized with methanol. Instead, after incubation with anti-PLVAP monoclonal antibodies, the cells were washed and fixed with 4% paraformaldehyde at room temperature for 10 minutes. Following this incubation, the cells were washed 3 times, then were incubated with FITC-conjugated Goat F(ab')$_2$ anti-mouse IgG. After three additional washes, the cells were processed for immunofluorescent microscopy as described in Example 3.

Figure 23A:
FIG. 23A is a fluorescence micrograph depicting human vascular endothelial cells (HUVECs) that were stained with control mouse IgG. Nuclei were stained with 4',6-diamidino-2-phenylindole (DAPI).
Figure 23B:
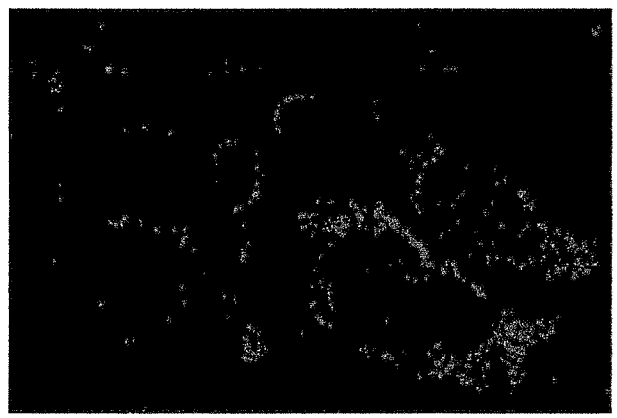
FIG. 23B is a fluorescence micrograph depicting human vascular endothelial cells (HUVECs) that were stained with KFCC-GY4 monoclonal antibody to PLVAP. KFCC-GY4 monoclonal anti-PLVAP antibodies reacted positively with the surfaces of the human vascular endothelial cells. Nuclei were stained with 4',6-diamidino-2-phenylindole (DAPI).
Figure 23C:
FIG. 23C is a fluorescence micrograph depicting human vascular endothelial cells (HUVECs) that were stained with KFCC-GY5 monoclonal antibody to PLVAP. KFCC-GY5 monoclonal anti-PLVAP antibodies reacted positively with the surfaces of the human vascular endothelial cells. Nuclei were stained with 4',6-diamidino-2-phenylindole (DAPI).

Results:

Using the approach described above, only PLVAP protein expressed on the cell surface could be detected. The results of these experiments revealed that both KFCC-GY4 and KFCC-GY5 anti-PLVAP monoclonal antibodies bound to the surface of HCC vascular endothelial cells (FIGS. 23B and 23C), indicating that PLVAP protein is expressed on the surfaces of these cells. These findings suggest that antibodies that specifically bind PLVAP with high affinity will be able to bind to the surface of HCC vascular endothelial cells upon injection into the blood vessels of a hepatocellular carcinoma tumor.

What is claimed is:

1. A method of diagnosing hepatocellular carcinoma (HCC) in a human subject, comprising:
   I) detecting the level of PLVAP protein in an isolated biological sample from the subject using an isolated polypeptide that specifically binds SEQ ID NO: 23; and
   II) determining that the level of the PLVAP gene product in the sample is increased relative to a control, wherein an increased level of the PLVAP protein in the sample relative to the control is indicative of HCC in the subject, thereby diagnosing HCC in the subject,
   wherein the isolated polypeptide is selected from:
   i) an isolated polypeptide comprising:
      1) an antibody variable domain that comprises:
         a) a CDR1 consisting of SEQ ID NO:5;
         b) a CDR2 consisting of SEQ ID NO:6; and
         c) a CDR3 consisting of SEQ ID NO:7; and
      2) an antibody variable domain that comprises:
         d) a CDR1 consisting of SEQ ID NO:10;
         e) a CDR2 consisting of SEQ ID NO:11; and
         f) a CDR3 consisting of SEQ ID NO:12; and
   ii) an isolated polypeptide comprising:
      1) an antibody variable domain that comprises:
         a) a CDR1 consisting of SEQ ID NO:15;
         b) a CDR2 consisting of SEQ ID NO:16; and
         c) a CDR3 consisting of SEQ ID NO:17; and
      2) an antibody variable domain that comprises:
         d) a CDR1 consisting of SEQ ID NO:20;
         e) a CDR2 consisting of SEQ ID NO:21; and
         f) a CDR3 consisting of SEQ ID NO:22.

2. The method of claim 1, wherein the level of the PLVAP gene product in the sample is determined using enzyme-linked immunosorbent assay (ELISA) or immunohistochemical staining (IHC).

3. The method of claim 1, wherein the sample is a liver tissue sample.

4. The method of claim 3, wherein the liver tissue sample is selected from the group consisting of a biopsy and a fine needle aspiration sample.

5. The method of claim 4, wherein the control is selected from the group consisting of a reference standard, the level of the PLVAP gene product in a normal liver sample from the same subject, and the level of the PLVAP gene product in a normal liver sample from another subject.

6. The method of claim 1, wherein the isolated polypeptide of subpart i) is the monoclonal antibody KFCC-GY4.

7. The method of claim 1, wherein the isolated polypeptide of subpart ii) is the monoclonal antibody KFCC-GY5.

8. The method of claim 1, wherein the isolated polypeptide of subpart i) comprises a $V_H$ domain having the amino acid sequence set forth in SEQ ID NO: 4 and a $V_L$ domain having the amino acid sequence set forth in SEQ ID NO: 9.

9. The method of claim 1, wherein the isolated polypeptide of subpart ii) comprises a $V_H$ domain having the amino acid sequence set forth in SEQ ID NO: 14 and a $V_L$ domain having the amino acid sequence set forth in SEQ ID NO: 19.

10. An in vivo method of detecting hepatocellular carcinoma (HCC) in a subject, comprising:
   I) administering an isolated polypeptide that specifically binds SEQ ID NO: 23 to the subject by intra-arterial injection, wherein the isolated polypeptide comprises a radioisotope;
   II) obtaining an image of the liver of the subject; and
   III) detecting accumulation of the antibody in the liver of the subject, thereby detecting HCC in the subject,
   wherein the isolated polypeptide is selected from:
   i) an isolated polypeptide comprising:
      1) an antibody variable domain that comprises:
         a) a CDR1 consisting of SEQ ID NO:5;
         b) a CDR2 consisting of SEQ ID NO:6; and
         c) a CDR3 consisting of SEQ ID NO:7; and
      2) an antibody variable domain that comprises:
         d) a CDR1 consisting of SEQ ID NO:10;
         e) a CDR2 consisting of SEQ ID NO:11; and
         f) a CDR3 consisting of SEQ ID NO:12; and
   ii) an isolated polypeptide comprising:
      1) an antibody variable domain that comprises:
         a) a CDR1 consisting of SEQ ID NO:15;
         b) a CDR2 consisting of SEQ ID NO:16; and
         c) a CDR3 consisting of SEQ ID NO:17; and
      2) an antibody variable domain that comprises:
         d) a CDR1 consisting of SEQ ID NO:20;
         e) a CDR2 consisting of SEQ ID NO:21; and
         f) a CDR3 consisting of SEQ ID NO:22.

11. The method of claim 10, wherein the isolated polypeptide of subpart i) is the monoclonal antibody KFCC-GY4.

12. The method of claim 10, wherein the isolated polypeptide of subpart ii) is the monoclonal antibody KFCC-GY5.

13. The method of claim 10, wherein the isolated polypeptide of subpart i) comprises a $V_H$ domain having the amino acid sequence set forth in SEQ ID NO: 4 and a $V_L$ domain having the amino acid sequence set forth in SEQ ID NO: 9.

14. The method of claim 10, wherein the isolated polypeptide of subpart ii) comprises a $V_H$ domain having the amino acid sequence set forth in SEQ ID NO: 14 and a $V_L$ domain having the amino acid sequence set forth in SEQ ID NO: 19.

* * * * *

UNITED STATES PATENT AND TRADEMARK OFFICE
CERTIFICATE OF CORRECTION

PATENT NO. : 10,370,445 B2
APPLICATION NO. : 15/370711
DATED : August 6, 2019
INVENTOR(S) : Kao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

Signed and Sealed this
Second Day of June, 2020

Andrei Iancu
*Director of the United States Patent and Trademark Office*

SEQUENCE LISTING

<160> NUMBER OF SEQ ID NOS: 35

<210> SEQ ID NO 1
<211> LENGTH: 1322
<212> TYPE: DNA
<213> ORGANISM: Artificial Sequence
<220> FEATURE:
<223> OTHER INFORMATION: Coding sequence for recombinant His-tagged
      human PLVAP amino acid residues 51-442

<400> SEQUENCE: 1

| | | | | | |
|---|---|---|---|---|---|
| atgggcagca | gccatcatca | tcatcatcac | agcagcggcc | tggtgccgcg | cggcagccat | 60 |
| atgaacgtgc | acgtgagcac | agagtccaac | ctgcaggcca | ccgagcgccg | agccgagggc | 120 |
| ctatacagtc | agctcctagg | gctcacggcc | tcccagtcca | acttgaccaa | ggagctcaac | 180 |
| ttcaccaccc | gcgccaagga | tgccatcatg | cagatgtggc | tgaatgctcg | ccgcgacctg | 240 |
| gaccgcatca | atgccagctt | ccgccagtgc | cagggtgacc | gggtcatcta | cacgaacaat | 300 |
| cagaggtaca | tggctgccat | catcttgagt | gagaagcaat | gcagagatca | attcaaggac | 360 |
| atgaacaaga | gctgcgatgc | cttgctcttc | atgctgaatc | agaaggtgaa | gacgctggag | 420 |
| gtggagatag | ccaaggagaa | gaccatttgc | actaaggata | ggaaagcgt | gctgctgaac | 480 |
| aaacgcgtgg | cggaggaaca | gctggttgaa | tgcgtgaaaa | cccgggagct | gcagcaccaa | 540 |
| gagcgccagc | tggccaagga | gcaactgcaa | aaggtgcaag | ccctctgcct | gcccctggac | 600 |
| aaggacaagt | ttgagatgga | ccttcgtaac | ctgtggaggg | actccattat | cccacgcagc | 660 |
| ctggacaacc | tgggttacaa | cctctaccat | cccctgggct | cggaattggc | ctccatccgc | 720 |
| agagcctgcg | accacatgcc | cagcctcatg | agctccaagg | tggaggagct | ggcccggagc | 780 |
| ctccgggcgg | atatcgaacg | cgtggcccgc | gagaactcag | acctccaacg | ccagaagctg | 840 |
| gaagcccagc | agggcctgcg | ggccagtcag | gaggcgaaac | agaaggtgga | aaggaggct | 900 |
| caggcccggg | aggccaagct | ccaagctgaa | tgctcccggc | agacccagct | agcgctggag | 960 |
| gagaaggcgg | tgctgcggaa | ggaacgagac | aacctggcca | aggagctgga | agagaagaag | 1020 |
| agggaggcgg | agcagctcag | gatggagctg | gccatcagaa | actcagccct | ggacacctgc | 1080 |
| atcaagacca | agtcgcagcc | gatgatgcca | gtgtcaaggc | ccatgggccc | tgtccccaac | 1140 |
| ccccagccca | tcgacccagc | tagcctggag | gagttcaaga | ggaagatcct | ggagtcccag | 1200 |
| aggccccctg | caggcatccc | tgtagcccca | tccagtggct | gaggaggctc | caggcctgag | 1260 |
| gaccaaggga | tggcccgact | cggcggtttg | cggaggatgc | agggatatgc | tcacagggat | 1320 |
| tc | | | | | | 1322 |

<210> SEQ ID NO 2
<211> LENGTH: 413
<212> TYPE: PRT
<213> ORGANISM: Artificial Sequence
<220> FEATURE:
<223> OTHER INFORMATION: Recombinant His-tagged human PLVAP amino acid
      residues 51-442

<400> SEQUENCE: 2

Met Gly Ser Ser His His His His His His Ser Ser Gly Leu Val Pro
1               5                   10                  15

Arg Gly Ser His Met Asn Val His Val Ser Thr Glu Ser Asn Leu Gln
            20                  25                  30

Ala Thr Glu Arg Arg Ala Glu Gly Leu Tyr Ser Gln Leu Leu Gly Leu
        35                  40                  45

```
Thr Ala Ser Gln Ser Asn Leu Thr Lys Glu Leu Asn Phe Thr Thr Arg
    50                  55                  60

Ala Lys Asp Ala Ile Met Gln Met Trp Leu Asn Ala Arg Arg Asp Leu
65              70                  75                  80

Asp Arg Ile Asn Ala Ser Phe Arg Gln Cys Gln Gly Asp Arg Val Ile
                85                  90                  95

Tyr Thr Asn Asn Gln Arg Tyr Met Ala Ala Ile Ile Leu Ser Glu Lys
            100                 105                 110

Gln Cys Arg Asp Gln Phe Lys Asp Met Asn Lys Ser Cys Asp Ala Leu
        115                 120                 125

Leu Phe Met Leu Asn Gln Lys Val Lys Thr Leu Glu Val Glu Ile Ala
    130                 135                 140

Lys Glu Lys Thr Ile Cys Lys Asp Lys Glu Ser Val Leu Leu Asn Lys
145                 150                 155                 160

Arg Val Ala Glu Thr Glu Gln Leu Val Glu Cys Val Lys Thr Arg Glu
                165                 170                 175

Leu Gln His Gln Glu Arg Gln Leu Ala Lys Glu Gln Leu Gln Lys Val
            180                 185                 190

Gln Ala Leu Cys Leu Pro Leu Asp Lys Asp Lys Phe Glu Met Asp Leu
        195                 200                 205

Arg Asn Leu Trp Arg Asp Ser Ile Ile Pro Arg Ser Leu Asp Asn Leu
    210                 215                 220

Gly Tyr Asn Leu Tyr His Pro Leu Gly Ser Glu Leu Ala Ser Ile Arg
225                 230                 235                 240

Arg Ala Cys Asp His Met Pro Ser Leu Met Ser Ser Lys Val Glu Glu
                245                 250                 255

Leu Ala Arg Ser Leu Arg Ala Asp Ile Glu Arg Val Ala Arg Glu Asn
            260                 265                 270

Ser Asp Leu Gln Arg Gln Lys Leu Glu Ala Gln Gln Gly Leu Arg Ala
        275                 280                 285

Ser Gln Glu Ala Lys Gln Lys Val Glu Lys Ala Gln Ala Arg Glu
    290                 295                 300

Ala Lys Leu Gln Ala Glu Cys Ser Arg Gln Thr Gln Leu Ala Leu Glu
305                 310                 315                 320

Glu Lys Ala Val Leu Arg Lys Glu Arg Asp Asn Leu Ala Lys Glu Leu
                325                 330                 335

Glu Glu Lys Lys Arg Glu Ala Glu Gln Leu Arg Met Glu Leu Ala Ile
            340                 345                 350

Arg Asn Ser Ala Leu Asp Thr Cys Ile Lys Thr Lys Ser Gln Pro Met
        355                 360                 365

Met Pro Val Ser Arg Pro Met Gly Pro Val Pro Asn Pro Gln Pro Ile
    370                 375                 380

Asp Pro Ala Ser Leu Glu Glu Phe Lys Arg Lys Ile Leu Glu Ser Gln
385                 390                 395                 400

Arg Pro Pro Ala Gly Ile Pro Val Ala Pro Ser Ser Gly
                405                 410

<210> SEQ ID NO 3
<211> LENGTH: 342
<212> TYPE: DNA
<213> ORGANISM: Artificial Sequence
<220> FEATURE:
<223> OTHER INFORMATION: KFCC-GY4 VH domain coding sequence

<400> SEQUENCE: 3
```

```
gaggttcagc tgcagcagtc tggggcagag tttgtgaggt caggggcctc agtcaagttg      60
tcctgcacag cttctggctt caacattaaa gactactata tacactgggt gaagcagagg     120
cctgaacagg gcctggagtg gattggatgg attgatcctg agaatggtga tattgaatat     180
gccccgaagt tccagggcaa ggccactatg actgcagaca catcctccaa tacagcctac     240
ctgcagttca gcagcctgac atctgaggac actgccgtct attactgtct ctaccaagaa     300
ggctcctggg gccaaggcac cactctcaca gtctcctcag cc                        342
```

```
<210> SEQ ID NO 4
<211> LENGTH: 114
<212> TYPE: PRT
<213> ORGANISM: Artificial Sequence
<220> FEATURE:
<223> OTHER INFORMATION: KFCC-GY4 VH domain

<400> SEQUENCE: 4

Glu Val Gln Leu Gln Gln Ser Gly Ala Glu Phe Val Arg Ser Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asp Ile Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Leu Tyr Gln Glu Gly Ser Trp Gly Gln Gly Thr Thr Leu Thr Val Ser
            100                 105                 110

Ser Ala
```

```
<210> SEQ ID NO 5
<211> LENGTH: 5
<212> TYPE: PRT
<213> ORGANISM: Artificial Sequence
<220> FEATURE:
<223> OTHER INFORMATION: CDR1 sequence

<400> SEQUENCE: 5

Asp Tyr Tyr Ile His
1               5
```

```
<210> SEQ ID NO 6
<211> LENGTH: 17
<212> TYPE: PRT
<213> ORGANISM: Artificial Sequence
<220> FEATURE:
<223> OTHER INFORMATION: CDR2 sequence

<400> SEQUENCE: 6

Trp Ile Asp Pro Glu Asn Gly Asp Ile Glu Tyr Ala Pro Lys Phe Gln
1               5                   10                  15

Gly
```

```
<210> SEQ ID NO 7
<211> LENGTH: 4
<212> TYPE: PRT
<213> ORGANISM: Artificial Sequence
<220> FEATURE:
```

<223> OTHER INFORMATION: CDR3 sequence

<400> SEQUENCE: 7

Gln Glu Gly Ser
1

<210> SEQ ID NO 8
<211> LENGTH: 336
<212> TYPE: DNA
<213> ORGANISM: Artificial Sequence
<220> FEATURE:
<223> OTHER INFORMATION: KFCC-GY4 VL domain coding sequence

<400> SEQUENCE: 8

```
gatgttgtga tgacccagac tccactcact ttgtcggtta ccattggaca accagcctcc    60
atctcttgca agtcaagtca gagcctctta aatagtgatg aaagacata tttgaattgg    120
ttgttacaga ggccaggcca gtctccaaag cgcctaatct atctggtgtc taaattggac    180
tctggagtcc ctgacaggtt cactggcagt ggatcaggga cagatttcac actgaaaatc    240
agcagagtgg aggctgagga tttgggagtt tattattgct ggcaaggtac acattttccg    300
ttcacgttcg gaggggggac caagctggaa ataaaa                              336
```

<210> SEQ ID NO 9
<211> LENGTH: 111
<212> TYPE: PRT
<213> ORGANISM: Artificial Sequence
<220> FEATURE:
<223> OTHER INFORMATION: KFCC-GY4 VL domain

<400> SEQUENCE: 9

Asp Val Val Met Thr Gln Pro Leu Thr Leu Ser Val Thr Ile Gly Gln
1               5                   10                  15

Pro Ala Ser Ile Ser Cys Lys Ser Ser Gln Ser Leu Leu Asn Ser Asp
            20                  25                  30

Gly Lys Thr Tyr Leu Asn Trp Leu Leu Gln Arg Pro Gly Gln Ser Pro
        35                  40                  45

Lys Arg Leu Ile Tyr Leu Val Ser Lys Leu Asp Ser Gly Val Pro Asp
    50                  55                  60

Arg Phe Thr Gly Ser Gly Ser Gly Thr Asp Phe Thr Leu Lys Ile Ser
65                  70                  75                  80

Arg Val Glu Ala Glu Asp Leu Gly Val Tyr Tyr Cys Trp Gln Gly Thr
                85                  90                  95

His Phe Pro Phe Thr Phe Gly Gly Gly Thr Lys Leu Glu Ile Lys
            100                 105                 110

<210> SEQ ID NO 10
<211> LENGTH: 16
<212> TYPE: PRT
<213> ORGANISM: Artificial Sequence
<220> FEATURE:
<223> OTHER INFORMATION: CDR1 sequence

<400> SEQUENCE: 10

Lys Ser Ser Gln Ser Leu Leu Asn Ser Asp Gly Lys Thr Tyr Leu Asn
1               5                   10                  15

<210> SEQ ID NO 11
<211> LENGTH: 7
<212> TYPE: PRT
<213> ORGANISM: Artificial Sequence
<220> FEATURE:

<223> OTHER INFORMATION: CDR2 sequence

<400> SEQUENCE: 11

Leu Val Ser Lys Leu Asp Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: CDR3 sequence

<400> SEQUENCE: 12

Trp Gln Gly Thr His Phe Pro Phe Thr
 1               5

<210> SEQ ID NO 13
<211> LENGTH: 342
<212> TYPE: DNA
<213> ORGANISM: Artificial Sequence
<220> FEATURE:
<223> OTHER INFORMATION: KFCC-GY-5-VH domain coding sequence

<400> SEQUENCE: 13
caggtccaac tgcagcagcc tggggctgag ctggtgaggc ctggggcttc agtgaagctg     60
tcctgcaagg cttctggcta caccttcacc agcaactaca taaactgggt gaaacagagg    120
cctggacagg gccttgagtg gatcggaaat atttatcctt ctgatggttt tactaactac    180
aatcaaaagt tcaaggacag ggccacattg actgtagaca atcctccag cacagcctac    240 atgcagctca gcagcccgac atctgaggac tctgcggtct attactgtac aagaaacttc    300
gatgtctggg gcgcagggac cacggtcacc gtctcctcag cc                       342

<210> SEQ ID NO 14
<211> LENGTH: 114
<212> TYPE: PRT
<213> ORGANISM: Artificial Sequence
<220> FEATURE:
<223> OTHER INFORMATION: KFCC-GY5 VH domain

<400> SEQUENCE: 14

Gln Val Gln Leu Gln Gln Pro Gly Ala Glu Leu Val Arg Pro Gly Ala
 1               5                  10                  15

Ser Val Lys Leu Ser Cys Lys Ala Ser Gly Tyr Thr Phe Thr Ser Asn
             20                  25                  30

Tyr Ile Asn Trp Val Lys Gln Arg Pro Gly Gln Gly Leu Glu Trp Ile
         35                  40                  45

Gly Asn Ile Tyr Pro Ser Asp Gly Phe Thr Asn Tyr Asn Gln Lys Phe
     50                  55                  60

Lys Asp Arg Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
                 85                  90                  95

Thr Arg Asn Phe Asp Val Trp Gly Ala Gly Thr Thr Val Thr Val Ser
            100                 105                 110

Ser Ala

<210> SEQ ID NO 15
<211> LENGTH: 5
<212> TYPE: PRT

<210> SEQ ID NO 15
<211> LENGTH: 5
<212> TYPE: PRT
<213> ORGANISM: Artificial Sequence
<220> FEATURE:
<223> OTHER INFORMATION: CDR1 sequence

<400> SEQUENCE: 15

Ser Asn Tyr Ile Asn
1               5

<210> SEQ ID NO 16
<211> LENGTH: 17
<212> TYPE: PRT
<213> ORGANISM: Artificial Sequence
<220> FEATURE:
<223> OTHER INFORMATION: CDR2 sequence

<400> SEQUENCE: 16

Asn Ile Tyr Pro Ser Asp Gly Phe Thr Asn Tyr Asn Gln Lys Phe Lys
1               5                   10                  15

Asp

<210> SEQ ID NO 17
<211> LENGTH: 4
<212> TYPE: PRT
<213> ORGANISM: Artificial Sequence
<220> FEATURE:
<223> OTHER INFORMATION: CDR3 sequence

<400> SEQUENCE: 17

Asn Phe Asp Val
1

<210> SEQ ID NO 18
<211> LENGTH: 336
<212> TYPE: DNA
<213> ORGANISM: Artificial Sequence
<220> FEATURE:
<223> OTHER INFORMATION: KFCC-GY5 VL domain coding sequence

<400> SEQUENCE: 18
gatgttgtga tgacccaaac tccactctcc ctgcctgtca gtcttggaga tcaagcctcc      60
atctcttgca gatctagtca gagccttgtc cacagtaatg gaaacaccta tttacagtgg     120
tacctgcaga agccaggcca gtctccaaag ctcctgatct acacagtttc aaccgatttt     180
tctggggtcc cagacaggtt cagtggcagt ggatcagggc cagatttcac actcaagatc     240
agcagagtgg aggctgagga tctgggagtt tatttctgct ctcaaagtac acatgttcct     300
ttcacgttcg gctcggggac aaagttggaa ataaaa                               336

<210> SEQ ID NO 19
<211> LENGTH: 112
<212> TYPE: PRT
<213> ORGANISM: Artificial Sequence
<220> FEATURE:
<223> OTHER INFORMATION: KFCC-GY5 VL domain

<400> SEQUENCE: 19

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu Gln Trp Tyr Leu Gln Lys Pro Gly Gln Ser
            35                  40                  45

Pro Lys Leu Leu Ile Tyr Thr Val Ser Asn Arg Phe Ser Gly Val Pro

```
                50                  55                  60
Asp Arg Phe Ser Gly Ser Gly Ser Gly Pro Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
                100                 105                 110

<210> SEQ ID NO 20
<211> LENGTH: 16
<212> TYPE: PRT
<213> ORGANISM: Artificial Sequence
<220> FEATURE:
<223> OTHER INFORMATION: CDR1 sequence

<400> SEQUENCE: 20

Arg Ser Ser Gln Ser Leu Val His Ser Asn Gly Asn Thr Tyr Leu Gln
  1               5                  10                  15

<210> SEQ ID NO 21
<211> LENGTH: 7
<212> TYPE: PRT
<213> ORGANISM: Artificial Sequence
<220> FEATURE:
<223> OTHER INFORMATION: CDR2 sequence

<400> SEQUENCE: 21

Thr Val Ser Asn Arg Phe Ser
  1               5

<210> SEQ ID NO 22
<211> LENGTH: 9
<212> TYPE: PRT
<213> ORGANISM: Artificial Sequence
<220> FEATURE:
<223> OTHER INFORMATION: CDR3 sequence

<400> SEQUENCE: 22

Ser Gln Ser Thr His Val Pro Phe Thr
  1               5

<210> SEQ ID NO 23
<211> LENGTH: 442
<212> TYPE: PRT
<213> ORGANISM: Homo sapiens

<400> SEQUENCE: 23

Met Gly Leu Ala Met Glu His Gly Gly Ser Tyr Ala Arg Ala Gly Gly
  1               5                  10                  15

Ser Ser Arg Gly Cys Trp Tyr Tyr Leu Arg Tyr Phe Leu Phe Val
                 20                  25                  30

Ser Leu Ile Gln Phe Leu Ile Ile Leu Gly Leu Val Leu Phe Met Val
             35                  40                  45

Tyr Gly Asn Val His Val Ser Thr Glu Ser Asn Leu Gln Ala Thr Glu
         50                  55                  60

Arg Arg Ala Glu Gly Leu Tyr Ser Gln Leu Leu Gly Leu Thr Ala Ser
 65                  70                  75                  80

Gln Ser Asn Leu Thr Lys Glu Leu Asn Phe Thr Thr Arg Ala Lys Asp
                 85                  90                  95

Ala Ile Met Gln Met Trp Leu Asn Ala Arg Arg Asp Leu Asp Arg Ile
                100                 105                 110
```

| | | | | | | | | | | | | |
|---|---|---|---|---|---|---|---|---|---|---|---|---|
|Asn|Ala|Ser|Phe|Arg|Gln|Cys|Gln|Gly|Asp|Arg|Val|Ile|Tyr|Thr|Asn|
| | |115| | | |120| | | |125| | | | | |

Asn Ala Ser Phe Arg Gln Cys Gln Gly Asp Arg Val Ile Tyr Thr Asn
          115                 120                 125

Asn Gln Arg Tyr Met Ala Ala Ile Ile Leu Ser Glu Lys Gln Cys Arg
130                 135                 140

Asp Gln Phe Lys Asp Met Asn Lys Ser Cys Asp Ala Leu Leu Phe Met
145                 150                 155                 160

Leu Asn Gln Lys Val Lys Thr Leu Glu Val Glu Ile Ala Lys Glu Lys
                165                 170                 175

Thr Ile Cys Thr Lys Asp Lys Glu Ser Val Leu Leu Asn Lys Arg Val
            180                 185                 190

Ala Glu Glu Gln Leu Val Glu Cys Val Lys Thr Arg Glu Leu Gln His
        195                 200                 205

Gln Glu Arg Gln Leu Ala Lys Glu Gln Leu Gln Lys Val Gln Ala Leu
210                 215                 220

Cys Leu Pro Leu Asp Lys Asp Lys Phe Glu Met Asp Leu Arg Asn Leu
225                 230                 235                 240

Trp Arg Asp Ser Ile Ile Pro Arg Ser Leu Asp Asn Leu Gly Tyr Asn
                245                 250                 255

Leu Tyr His Pro Leu Gly Ser Glu Leu Ala Ser Ile Arg Arg Ala Cys
            260                 265                 270

Asp His Met Pro Ser Leu Met Ser Ser Lys Val Glu Glu Leu Ala Arg
        275                 280                 285

Ser Leu Arg Ala Asp Ile Glu Arg Val Ala Arg Glu Asn Ser Asp Leu
        290                 295                 300

Gln Arg Gln Lys Leu Glu Ala Gln Gln Gly Leu Arg Ala Ser Gln Glu
305                 310                 315                 320

Ala Lys Gln Lys Val Glu Lys Glu Ala Gln Ala Arg Glu Ala Lys Leu
                325                 330                 335

Gln Ala Glu Cys Ser Arg Gln Thr Gln Leu Ala Leu Glu Glu Lys Ala
            340                 345                 350

Val Leu Arg Lys Glu Arg Asp Asn Leu Ala Lys Glu Leu Glu Glu Lys
        355                 360                 365

Lys Arg Glu Ala Glu Gln Leu Arg Met Glu Leu Ala Ile Arg Asn Ser
370                 375                 380

Ala Leu Asp Thr Cys Ile Lys Thr Lys Ser Gln Pro Met Met Pro Val
385                 390                 395                 400

Ser Arg Pro Met Gly Pro Val Pro Asn Pro Gln Pro Ile Asp Pro Ala
                405                 410                 415

Ser Leu Glu Glu Phe Lys Arg Lys Ile Leu Glu Ser Gln Arg Pro Pro
            420                 425                 430

Ala Gly Ile Pro Val Ala Pro Ser Ser Gly
        435                 440

<210> SEQ ID NO 24
<211> LENGTH: 2317
<212> TYPE: DNA
<213> ORGANISM: Homo sapiens

<400> SEQUENCE: 24
cggacgcgtg ggtgagcagg gacggtgcac cggacggcgg gatcgagcaa atgggtctgg    60
ccatggagca cggagggtcc tacgctcggg cgggggggcag ctctcggggc tgctggtatt   120
acctgcgcta cttcttcctc ttcgtctccc tcatccaatt cctcatcatc ctggggctcg   180
tgctcttcat ggtctatggc aacgtgcacg tgagcacaga gtccaacctg caggccaccg   240

```
agcgccgagc cgagggccta tacagtcagc tcctagggct cacggcctcc cagtccaact    300
tgaccaagga gctcaacttc accacccgcg ccaaggatgc catcatgcag atgtggctga    360
atgctcgccg cgacctggac cgcatcaatg ccagcttccg ccagtgccag ggtgaccggg    420
tcatctacac gaacaatcag aggtacatgg ctgccatcat cttgagtgag aagcaatgca    480
gagatcaatt caaggacatg aacaagagct gcgatgcctt gctcttcatg ctgaatcaga    540
aggtgaagac gctggaggtg gagatagcca aggagaagac catttgcact aaggataagg    600
aaagcgtgct gctgaacaaa cgcgtggcgg aggaacagct ggttgaatgc gtgaaaaccc    660
gggagctgca gcaccaagag cgccagctgg ccaaggagca actgcaaaag gtgcaagccc    720
tctgcctgcc cctggacaag gacaagtttg agatggacct tcgtaacctg tggagggact    780
ccattatccc acgcagcctg dacaacctgg gttacaacct ctaccatccc ctgggctcgg    840
aattggcctc catccgcaga gcctgcgacc acatgcccag cctcatgagc tccaaggtgg    900
aggagctggc ccggagcctc cgggcggata tcgaacgcgt ggcccgcgag aactcagacc    960
tccaacgcca gaagctggaa gcccagcagg gcctgcgggc cagtcaggag gcgaaacaga   1020
aggtggagaa ggaggctcag gcccgggagg ccaagctcca agctgaatgc tcccggcaga   1080
cccagctagc gctggaggag aaggcggtgc tgcggaagga acgagacaac ctggccaagg   1140
agctggaaga gaagaagagg gaggcggagc agctcaggat ggagctggcc atcagaaact   1200
cagccctgga cacctgcatc aagaccaagt cgcagccgat gatgccagtg tcaaggccca   1260
tgggccctgt ccccaacccc cagcccatcg acccagctag cctggaggag ttcaagagga   1320
agatcctgga gtcccagagg cccctgcag gcatccctgt agccccatcc agtggctgag   1380
gaggctccag gcctgaggac caagggatgg cccgactcgg cggtttgcgg aggatgcagg   1440
gatatgctca cagcgcccga cacaaccccc tcccgccgcc cccaaccacc cagggccacc   1500
atcagacaac tccctgcatg caaacccta gtaccctctc acaccccgcac ccgcgcctca   1560
cgatccctca cccagagcac acggccgcgg agatgacgtc acgcaagcaa cggcgctgac   1620
gtcacatatc accgtggtga tggcgtcacg tggccatgta dacgtcacga agagatatag   1680
cgatggcgtc gtgcagatgc agcacgtcgc acacagacat ggggaacttg gcatgacgtc   1740
acaccgagat gcagcaacga cgtcacgggc catgtcgacg tcacacatat taatgtcaca   1800
cagacgcggc gatggcatca cacagacggt gatgatgtca cacacagaca cagtgacaac   1860
acacaccatg acaacgacac ctatagatat ggcaccaaca tcacatgcac gcatgccctt   1920
tcacacacac tttctaccca attctcacct agtgtcacgt tcccccgacc ctggcacacg   1980
ggccaaggta cccacaggat cccatcccct cccgcacagc cctgggcccc agcacctccc   2040
ctcctccagc ttcctggcct cccagccact tcctcacccc cagtgcctgg acccggaggt   2100
gagaacagga agccattcac ctccgctcct tgagcgtgag tgtttccagg accccctcgg   2160
ggccctgagc cggggtgag ggtcacctgt tgtcggagg ggagccactc cttctccccc   2220
aactcccagc cctgcctgtg gcccgttgaa atgttggtgg cacttaataa atattagtaa   2280
atccttaaaa aaaaaaaaa aaaaaaaaa aaaaaaa                               2317
```

<210> SEQ ID NO 25
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 25
cctgcaggca tccctgta                                              18

<210> SEQ ID NO 26
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 26
cgggccatcc cttggt                                                16

<210> SEQ ID NO 27
<211> LENGTH: 16
<212> TYPE: DNA
<213> ORGANISM: Artificial Sequence
<220> FEATURE:
<223> OTHER INFORMATION: oligonucleotide probe

<400> SEQUENCE: 27
ccccatccag tggctg                                                16

<210> SEQ ID NO 28
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 28
ccttgagcgt gagtgtttcc a                                          21

<210> SEQ ID NO 29
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 29
gtcccccaac ttgagatgta tgaag                                      25

<210> SEQ ID NO 30
<211> LENGTH: 17
<212> TYPE: DNA
<213> ORGANISM: Artificial Sequence
<220> FEATURE:
<223> OTHER INFORMATION: oligonucleotide primer

<400> SEQUENCE: 30
ggcagggctg ggagttg                                               17

<210> SEQ ID NO 31
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 31
gtctcaagtc agtgtacagg taagc                                      25

<210> SEQ ID NO 32
<211> LENGTH: 16
<212> TYPE: DNA

```
<213> ORGANISM: Artificial Sequence
<220> FEATURE:
<223> OTHER INFORMATION: oligonucleotide probe

<400> SEQUENCE: 32
ctcccaggga gaccaa                                              16

<210> SEQ ID NO 33
<211> LENGTH: 18
<212> TYPE: DNA
<213> ORGANISM: Artificial Sequence
<220> FEATURE:
<223> OTHER INFORMATION: oligonucleotide probe

<400> SEQUENCE: 33
aaggagtggc tcccctcc                                            18

<210> SEQ ID NO 34
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 34
catatgaacg tgcacgtgag cacagagtcc                               30

<210> SEQ ID NO 35
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 35
ggatcctgag catatccctg catcctcc                                 28
```